(12) United States Patent
Pan et al.

(10) Patent No.: US 11,278,254 B2
(45) Date of Patent: Mar. 22, 2022

(54) SYSTEM AND METHOD FOR LOW-DOSE MULTI-SPECTRAL X-RAY TOMOGRAPHY

(71) Applicant: The University of Chicago, Chicago, IL (US)

(72) Inventors: Xiaochuan Pan, Chicago, IL (US); Buxin Chen, Chicago, IL (US); Zheng Zhang, Chicago, IL (US); Emil Sidky, Chicago, IL (US); Dan Xia, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 95 days.

(21) Appl. No.: 16/648,375

(22) PCT Filed: Sep. 21, 2018

(86) PCT No.: PCT/US2018/052175
§ 371 (c)(1),
(2) Date: Mar. 18, 2020

(87) PCT Pub. No.: WO2019/060688
PCT Pub. Date: Mar. 28, 2019

(65) Prior Publication Data
US 2020/0222016 A1    Jul. 16, 2020

Related U.S. Application Data

(60) Provisional application No. 62/562,138, filed on Sep. 22, 2017.

(51) Int. Cl.
*A61B 6/00* (2006.01)
*A61B 6/03* (2006.01)
*A61B 6/08* (2006.01)

(52) U.S. Cl.
CPC .............. *A61B 6/469* (2013.01); *A61B 6/032* (2013.01); *A61B 6/08* (2013.01); *A61B 6/4064* (2013.01); *A61B 6/482* (2013.01); *A61B 6/5205* (2013.01)

(58) Field of Classification Search
CPC ..... G06T 15/08; G06T 11/003; G06T 7/0012; G06T 2207/10081; G06T 2207/10116;
(Continued)

(56) References Cited

U.S. PATENT DOCUMENTS 7,245,755 B1    7/2007  Pan et al.
7,394,923 B2    7/2008  Zou et al.
(Continued)

FOREIGN PATENT DOCUMENTS

DE    10 2007 053390 A1    12/2008
JP    2008-054831 A        3/2008
(Continued)

OTHER PUBLICATIONS

The International Search Report and the Written Opinion issued for International Patent Application No. PCT/US18/52175 dated Jan. 17, 2019; pp. 1-11.
(Continued)

*Primary Examiner* — Don K Wong
(74) *Attorney, Agent, or Firm* — Bell & Manning, LLC

(57) ABSTRACT

A multi-spectral tomography imaging system includes one or more source devices configured to direct beams of radiation in multiple spectra to a region of interest (ROI), and one or more detectors configured to receive the beams of radiation. The system includes a processor configured to cause movement in at least one of the components such that a first beam of radiation with a first spectrum is directed to the ROI for less than 360 degrees of movement of the ROI. The processor is also configured to process data detected by
(Continued)

the one or more detectors, where the data results at least in part from the first beam of radiation with the first spectrum that is directed to the ROI for less than the 360 degrees of movement of the ROI. The processor is further configured to generate an image of the ROI based on the processed data.

13 Claims, 31 Drawing Sheets

(58) Field of Classification Search
CPC ....... G06T 2207/30004; G06T 2211/40; A61B 6/5205; A61B 6/035; A61B 6/4452; A61B 6/4007; A61B 6/032; A61B 6/4435; A61B 6/54; A61B 6/5235; A61B 6/5282; A61B 6/527
See application file for complete search history.

(56) References Cited

U.S. PATENT DOCUMENTS

| | | | |
|---|---|---|---|
| 7,444,011 | B2 | 10/2008 | Pan et al. |
| 8,121,245 | B2 | 2/2012 | Pan et al. |
| 8,605,975 | B2 | 12/2013 | Pan et al. |
| 8,923,587 | B2 | 12/2014 | Pan et al. |
| 9,613,442 | B2 | 4/2017 | Pan et al. |
| 2003/0156684 | A1 | 8/2003 | Fessler |
| 2004/0264628 | A1 | 12/2004 | Besson |
| 2013/0010917 | A1 | 1/2013 | Thibault et al. |
| 2013/0044861 | A1 | 2/2013 | Muller et al. |
| 2016/0123904 | A1 | 5/2016 | Masood et al. |
| 2016/0307340 | A1 | 10/2016 | Allmendinger et al. |
| 2016/0310086 | A1* | 10/2016 | Besson ............... A61B 6/5205 |
| 2017/0086775 | A1 | 3/2017 | Madhav et al. |

FOREIGN PATENT DOCUMENTS

| | | |
|---|---|---|
| JP | 2008-154784 A | 7/2008 |
| JP | 2010-284350 A | 12/2010 |
| JP | 2012-166026 A | 9/2012 |
| JP | 2016-516464 A | 9/2014 |
| WO | WO 2005/009206 A2 | 2/2005 |
| WO | WO 2012/009725 A1 | 1/2012 |
| WO | WO2014/141163 A3 | 9/2014 |

OTHER PUBLICATIONS

Emil Y. Sidky et al., "Optimization-based direct inversion of spectral CT data into a materials decomposition," The third international conference on image formation in X-ray computed tomography, pp. 1-4.

Xiaochuan Pan et al., "Optimization-based Reconstruction Exploiting Spectral Information in CT," The third international conference on image formation in x-ray computed tomography; pp. 228-232.

Buxin Chen et al., "Basis-image reconstruction directly from sparse-view data in spectral CT," *2014 IEEE Nuclear Science Symposium and Medical Imaging Conference (NSS/MIC)*, Seattle, WA, 2014, pp. 1-3, doi: 10.1109/NSSMIC.2014.7430810.

Buxin Chen et al., "Basis-Image Reconstruction Directly from Limited-Angle Data Sets in Spectral CT," In *The 13th International Meeting on Fully Three-Dimensional Image Reconstruction in Radiology and Nuclear Medicine*, pp. 495-498. 2015.

Buxin Chen et al., "An Investigation of Regularization for Basis Image Reconstruction in Spectral CT," In *2015 IEEE Nuclear Science Symposium and Medical Imaging Conference (NSS/MIC)*, pp. 1-3. IEEE, 2015.

Buxin Chen et al., "Algorithm-Enabled Half-Rotation Data Reconstruction in Spectral CT," pp. 1-4. The 4th International Conference on Image Formation in X-Ray Computed Tomography.

Buxin Chen et al., "Investigation of Non-Negativity Constraint on Basis Images in Half-Rotation Data Reconstruction in Spectral CT," In *2016 IEEE Nuclear Science Symposium, Medical Imaging Conference and Room-Temperature Semiconductor Detector Workshop (NSS/MIC/RTSD)*, pp. 1-3. IEEE, 2016.

Buxin Chen et al., "Algorithm-Enabled Varying Illumination Coverage Scan for Spectral Ct," AAPM 2017, Denver, CO, Aug. 3, 2017; pp. 1-10.

SPIE.Medical Imaging. Conferences & Courses Feb. 21-26, 2015, Renaissance Orlando at Sea World, Orlando, Florida, USA, pp. 1-84.

Cynthia H. McCollough et al., "Dual-and Multi-Energy CT: Principles, Technical Approaches, and Clinical Application," *Radiology*, Sep. 2015, vol. 276, No. 3; pp. 637-653.

Rina Foygel Barber et al., "An algorithm for constrained one-step inversion of spectral CT data," *Phys. Med. Biol.*, 2016, vol. 61; pp. 3784-3818.

The Extended European Search Report dated May 11, 2021 for European Patent Application No. 18858231.6; pp. 1-8.

The Japanese First Office Action (non-final Notice of Reasons for Rejection) dated Mar. 17, 2021 for Japanese Patent Application No. 2020-516528; pp. 1-5.

* cited by examiner

| phantom | DE-472 | | Lung | | | |
|---|---|---|---|---|---|---|
| material | iodine solution* | calcium solution* | lung tissue | adipose tissue | skeleton muscle | cortical bone |
| density (g/ml) | 0.002-0.02 | 0.05-0.6 | 0.1-0.6 | 0.88-0.95 | 1.11-1.21 | 1.53-2.05 |

FIG. 9

1: Initialize $b_k^{(0)} \leftarrow 0$, $\hat{g}^{(0)} \leftarrow g_M$
2: repeat iterations
3:   - POCS update -
4:   for $s = 1$ to $S$ do
5:     for $j = 0$ to $J^{(s)} - 1$ do
6:       for $k = 1$ to $K$ do
7:         $b_k^{(n+1)} = b_k^{(n)} + \gamma^{(n)} \mu_{jk}^{(s)} \tilde{\mu}_{jk}^{(s)} \dfrac{\hat{g}_j^{(s)}(n) - a_j^{(s)} \sum_k \mu_{jk}^{(s)} b_k^{(n)}}{\sum_k (\mu_{jk}^{(s)})^2 a_j^{(s)} \cdot a_j^{(s)T}} a_j^{(s)T}$
8:       end for
9:     end for
10:  end for
11:  - TV descent update -
12:  for $l = 1$ to $N_{TV}$ do
13:    for $k = 1$ to $K$ do
14:      $b_k^{(n+1)} \leftarrow b_k^{(n+1)} - \alpha_k^{(n+1)} \nabla_{b_k} \| b_k^{(n+1)} \|_{TV}$
15:    end for
16:  end for
17:  - NL term update step -
18:  for $s = 1$ to $S$ do
19:    for $j = 0$ to $J^{(s)} - 1$ do
20:      $\Delta g_j^{(s)(n+1)} = -\ln \sum_m \hat{g}_{jm}^{(s)} \exp\left(-\sum_k \Delta \mu_{jkm}^{(s)} a_j^{(s)} b_k^{(n+1)}\right)$
21:      $\hat{g}_j^{(s)(n+1)} \leftarrow g_{M_0}^{(s)} - \Delta g_j^{(s)(n+1)}$
22:    end for
23:  end for
24: until practical convergence conditions are satisfied

FIG. 25

SYSTEM AND METHOD FOR LOW-DOSE MULTI-SPECTRAL X-RAY TOMOGRAPHY

CROSS-REFERENCE TO RELATED APPLICATION

This application claims priority as a National Stage Application of International Application No. PCT/US18/52175, filed Sep. 21, 2018, which claims the priority benefit of U.S. Patent Application No. 62/562,138, filed Sep. 22, 2017, the contents of which are herein incorporated by reference in their entirety.

GOVERNMENT LICENSE RIGHTS

This invention was made with government support under CA182264, CA158446 and EB018102 awarded by the National Institutes of Health. The government has certain rights in the invention.

BACKGROUND

X-ray tomography, including computed tomography (CT), may be used for a variety of purposes, such as for screening, diagnosis, evaluation of diseases, analysis of materials, etc. In the screening, diagnosis, and evaluation cases, the X-ray tomographic images, including CT images, can measure quantities related to X-ray attenuation values at different X-ray energies in the imaged subject, such as a patient. One way to acquire additional information using X-rays is to measure the patient at multiple different energies, since the attenuation of all materials is energy dependent. This energy dependence is different for different materials. In dual-energy X-ray tomography, including dual-energy CT imaging, the subject is illuminated with two different X-ray spectra corresponding to two different energy distributions. In the medical X-ray imaging energy range, there are typically two dominant physical effects, i.e., the Compton and photoelectric effects.

SUMMARY

An illustrative multi-spectral tomography imaging system includes one or more source devices configured to direct beams of radiation in multiple spectra to a region of interest (ROI). The system also includes one or more detectors configured to receive at least a portion of the beams of radiation. The system further includes a processor in communication with the one or more source devices and the one or more detectors. The processor is configured to cause movement in at least one of the one or more source devices, the one or more detectors, and the ROI such that a first beam of radiation with a first spectrum is directed to the ROI for less than 360 degrees of movement of the ROI relative to the one or more source devices and the one or more detectors. The processor is also configured to process data detected by the one or more detectors, where the data results at least in part from the first beam of radiation with the first spectrum that is directed to the ROI for less than the 360 degrees of movement of the ROI. The processor is further configured to generate an image of the ROI based on the processed data.

An illustrative method of performing multi-spectral tomography includes directing, by one or more source devices, beams of radiation in multiple spectra to a region of interest (ROI). The method also includes receiving, by one or more detectors, at least a portion of the beams of radiation. The method also includes causing, by a processor in communication with the one or more source devices and the one or more detectors, movement in at least one of the one or more source devices, the one or more detectors, and the ROI. The method also includes processing, by the processor, data detected by the one or more detectors by solving an optimization problem based on the data, wherein the data results at least in part from a first beam of radiation with a first spectrum that is directed to the ROI. The method further includes generating, by the processor, an image of the ROI based on the processed data.

BRIEF DESCRIPTION OF THE DRAWINGS

The accompanying drawings, which are incorporated in and constitute a part of this specification, illustrate various aspects of the subject matter and together with the description, serve to explain its principles. Wherever convenient, the same reference numbers will be used throughout the drawings to refer to the same or like elements.

FIG. 9 is a table summarizing the materials used in the composition of the phantoms of FIG. 10 in accordance with an illustrative embodiment.

FIG. 25 depicts pseudo code used to implement non-convex-projection onto convex sets (NC-POCS) in accordance with an illustrative embodiment.

DETAILED DESCRIPTION

Multi-spectral X-ray tomography (MSXT) is an imaging technique that uses multiple different energy spectra to conduct tomography. One example of multi-spectral X-ray tomography is multi-spectral computed tomography (CT), in which various numbers of spectra may be used, such as two spectra, three spectra, four spectra, etc. As one example, dual-energy X-ray tomography acquisition is a technique that utilizes two different spectra to perform the imaging. In traditional X-ray imaging, a non-linear data model can be used to incorporate the product of an incident X-ray spectrum and a detector-energy response, which is referred to as the X-ray spectrum. In MSXT, multiple sets of data may be collected with different X-ray spectra. When seeking to determine basis images, the multiple sets of data can be used to form X-ray tomographic images, including CT images, at X-ray energies of interest.

There are four leading, distinctive methods currently used for dual-energy CT imaging. The first method, referred to as the single-kVp-switch method, uses a single X-ray source and a single detector array to collect dual-energy data sets by the performance of two full-rotation scans in which the source kVp is switched following the first full-rotation scan. The second method, referred to as the fast-kVp-switch method, also uses a single X-ray source and a single detector array for acquisition of dual-energy data sets in which the source invokes a fast kVp switch at each effective view in a full-rotation scan. The third method, referred to as the dual-source/detector method, employs two source-detector pairs of different effective X-ray spectra to collect dual-energy data sets within a full-rotation scan. The fourth method, referred to as the dual-layer-detector method, adopts a single X-ray source and a set of two-layer detectors with different energy responses for collecting dual-energy data sets within a full-rotation scan.

Figure 1A:
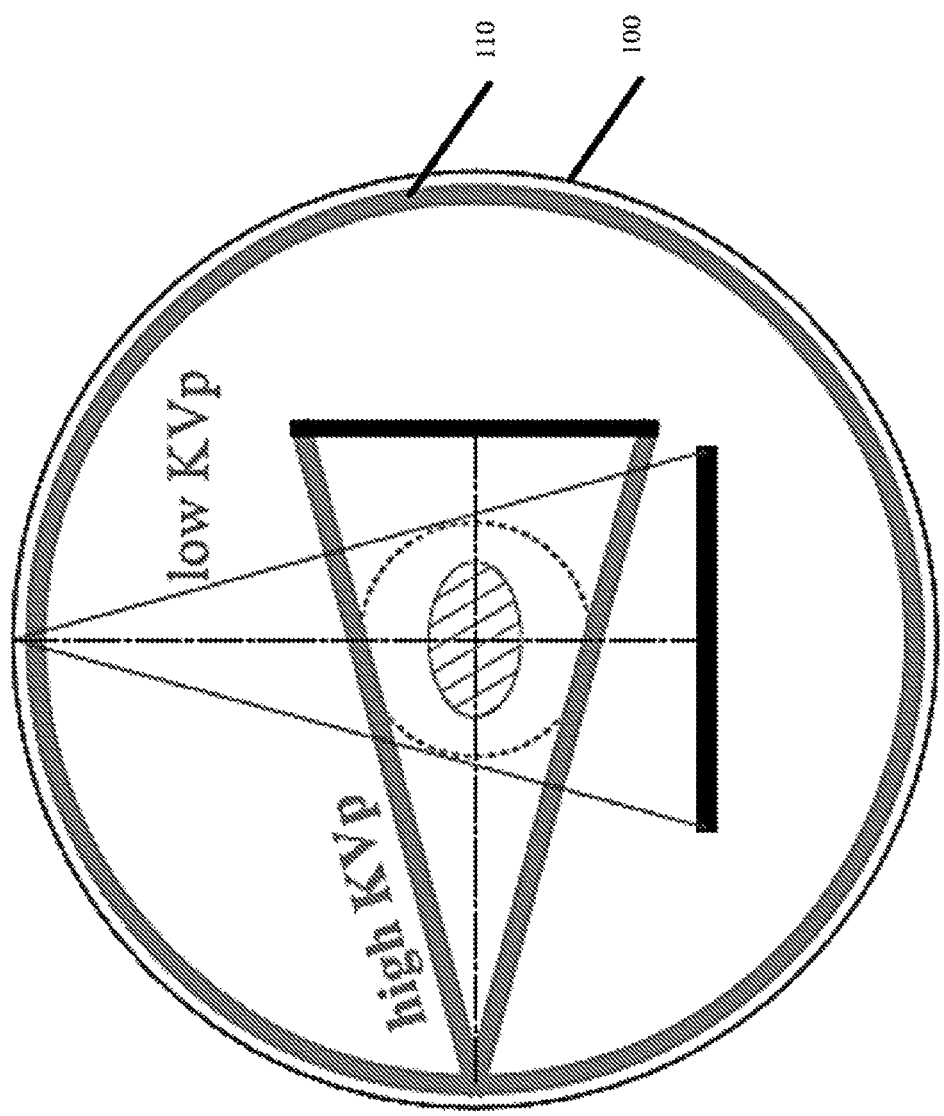
FIG. 1A depicts a single-kVp switch imaging technique in which there is one rotation for the low kVp and another rotation for the high kVp in accordance with an illustrative embodiment.

The four methods of performing dual-energy CT imaging involve the performance of two or one full-rotation scans. For example, the single-kVp-switch method, while simple to implement without the addition of hardware to a regular diagnostic CT system, doubles the imaging time and dose of a regular full-rotation scan because it carries out two full-rotation scans. As an example, FIG. 1A depicts a single-kVp switch imaging technique in which there is one rotation for the low kVp and another rotation for the high kVp in accordance with an illustrative embodiment. The fast-kVp-switch and dual-source/detector methods, while having half of the imaging time of the single-kVp-switch method, in essence also perform two scans within a single full rotation, and thus may also double imaging dose of a regular full-rotation scan. In addition, the fast-kVp-switch, dual-source/detector, and dual-layer-detector methods involve significant hardware additions as compared to a regular diagnostic CT. For example, the fast-kVp-switch method involves a unique, high performance X-ray source capable of rapid switching within a full rotation, the dual-source/detector method uses an additional pair of X-ray sources and detector arrays, and the dual-layer-detector method uses a highly specialized detector technology. This additional hardware considerably increases CT-system cost and complexity. The hardware cost and complexity of these techniques is one of the reasons for their lack of a wide adoption, particularly in non-diagnostic CT such as C-arm CT.

Described herein are optimization-based algorithms for image reconstruction in multispectral (or photon-counting) computed tomography. A challenge of optimization-based image reconstruction in MSXT stems from the inherently non-linear data model that can lead to a non-convex optimization program for which no mathematically exact solver appears to exist for achieving globally optimal solutions. As discussed in more detail below, a non-convex optimization program based on a non-linear data model is disclosed, with its first-order-optimality conditions derived. Further, a methodology is disclosed to solve the non-convex optimization program for image reconstruction in MSXT. In addition to consideration of image reconstruction for a standard scan configuration, the disclosed methodology may be applied to non-standard scan configurations with no or little hardware modification to existing CT systems, which can be of potential practical implications for lowered hardware cost, enhanced scanning flexibility, and reduced imaging dose/time in MSXT. Further, as discussed in more detail below, numerical studies are disclosed in support of the methodology and its implementation. These studies demonstrate and characterize the methodology in reconstructing images and in enabling non-standard configurations with variable scanning angular range and/or variable X-ray illumination coverage.

As discussed in more detail below, the proposed methodologies can be applied to a variety of scan configurations, and may affect one or more aspects of the systems such as hardware used, imaging dose, and scanning time. As a general matter, the methodology may be used for any multiple spectra X-ray tomography imaging system. More specifically, the method may be used in any type of X-ray tomography, such as CT. Further, the methodology may be used for any multiple numbers of spectra (such as two spectra, three spectra, etc.). In the case of the multiple spectra being limited to two spectra, the methodology may be used for any dual-energy X-ray tomography imaging system. Even more specifically, the proposed methodologies may be used for scan configurations for fast low-dose dual-energy CT imaging.

In an illustrative embodiment, a methodology is disclosed for a two spectra system that uses the scan configurations for reconstructing images from data containing rays that are measured only with one of the two spectra. The methodology thus enables the scan configurations disclosed herein, such as the short- and half-scan configurations, for realizing fast, low-dose dual-energy imaging on current conventional diagnostic and non-diagnostic CT systems. These enhancements are possible without hardware addition or modification to the current conventional diagnostic and non-diagnostic CT systems. The scan configurations, referred to as short-scan, partial-scan, and half-scan configurations, are enabled by the disclosed methodology developed for image reconstruction directly from dual-energy data. In this regard, the proposed methodologies may be used to reconstruct basis images from a variety of decomposition schemes, and monochromatic images may be reconstructed by use of the filtered back-projection algorithm from corrected data and used as benchmark references. Further, the proposed methodologies may be used in existing CT scanners, thus upgrading existing CT scanners to enable wide-spread application of dual-energy CT imaging. The techniques described herein are not limited to a particular type of tomography. For example, any discussion below regarding CT may be applied to other types of X-ray tomographic imaging known in the art. Likewise, any discussion below regarding X-ray tomographic imaging may likewise be applied to CT imaging.

In one implementation, the proposed methodologies use a limited data set for imaging. Though the discussion below focuses on two spectra, the MSXT imaging may be applied to any number of multiple spectra (such as three spectra, four spectra, etc.). In this regard, any discussion herein directed to two spectra may be applied to any number of multiple spectra. As discussed above, typically, the data set for each spectrum in the MSXT imaging is a full rotation (i.e., at least $2\pi$). In contrast, in a first implementation, the proposed methodology uses a data set that is less than $2\pi$ for at least one spectrum in the imaging process. Thus, in the instance that the MSXT imaging system uses two spectra for imaging, a data set for one spectrum is less than $2\pi$ and a data set for a second spectrum is $2\pi$ or greater. In a second specific implementation, the methodology uses a data set that is less than $2\pi$ for each spectrum used in the MSXT imaging. In the instance that the MSXT imaging system uses two spectra, a data set for a first spectrum is less that $2\pi$, and a data set for a second spectrum is also less than $2\pi$. In various embodiments, the data sets for a first spectrum and a second spectrum are both less than 360°; the data set for the first spectrum is less than 180° and the data set for the second spectrum is greater than 180° but less than 360°; the data sets for both the first spectrum and the second spectrum are less than 180°; the data set for the first spectrum is less than 90° and the data set for a second spectrum is greater than 90° but less than 180°; the data sets for both the first spectrum and the second spectrum are less than 90°; the data set for the first spectrum is less than 45° and the data set for a second spectrum is greater than 45° but less than 90°; the data sets for both the first spectrum and the second spectrum are less than 45°, etc. As another example, in the instance that the MSXT imaging system uses three spectra, the data sets for each of the first, second and third spectra are each less than $2\pi$.

The proposed MSXT imaging system may obtain the limited data set for the one or more spectra in one of several ways. In one embodiment, the MSXT imaging system may control the source in order for the MSXT imaging system to obtain the limited data set. The control of the source may include control of relative movement of the source and/or control of activation of the source (e.g., controlling the timing when the source outputs the different spectra). As one example, the MSXT imaging system may move the source/detectors relative to the object and during movement control the source (e.g., activate the source to generate light in the one or more spectra) to generate the limited data set. The MSXT imaging system may also move the source/detectors relative to the object in one of several embodiments. In one embodiment, the source/detectors may move and the object may be stationary in order for the source/detectors to move relative to the object. In another embodiment, the source/detectors may be stationary and the object may move in order for the source/detectors to move relative to the object. In still another embodiment, the source/detectors and the object may move in order for the source/detectors to move relative to the object. As another example, the MSXT imaging system may control the activation of the source so that the limited data set is obtained.

Thus, regardless of the relative movement, the MSXT imaging system can activate the source such that during the relative movement, the data generated comprises the limited data set. As one example, the MSXT imaging system may include a single source, with the MSXT imaging system controlling the single source such that light is output at the different spectra during the relative movement of less than $2\pi$.

In a first illustrative embodiment, the MSXT imaging system includes a single source with slow kVp switching, with the MSXT imaging system performing the slow kVp switching such that at each of the different spectra, the movement is less than $2\pi$. The movement can be of the source, detector, and/or the patient or other object being imaged. For example, the MSXT imaging system may activate the source to generate the first spectrum while generating relative movement greater than 180° but less than 360°, use the slow kVp switching to switch the source to the second spectrum, and thereafter activate the source to generate the second spectrum while generating relative movement greater than 180° but less than 360°. As another example, the MSXT imaging system may activate the source to generate the first spectrum while generating relative movement greater than 90° but less than 180°, use the slow kVp switching to switch the source to the second spectrum, and thereafter activate the source to generate the second spectrum while generating relative movement greater than 180° but less than 360°. As still another example, the MSXT imaging system may activate the source to generate the first spectrum while generating relative movement greater than 90° but less than 180°, use the slow kVp switching to switch the source to the second spectrum, and thereafter activate the source to generate the second spectrum while generating relative movement greater than 90° but less than 180°. As yet another example, the MSXT imaging system may activate the source to generate the first spectrum while generating relative movement greater than 45° but less than 90°, use the slow kVp switching to switch the source to the second spectrum, and thereafter activate the source to generate the second spectrum while generating relative movement greater than 45° but less than 180°. As still another example, the MSXT imaging system may activate the source to generate the first spectrum while generating relative movement greater than 45° but less than 90°, use the slow kVp switching to switch the source to the second spectrum, and thereafter activate the source to generate the second spectrum while generating relative movement greater than 45° but less than 90°.

In a second illustrative embodiment, the MSXT imaging system may include a single source with fast kVp switching, with the MSXT imaging system performing the fast kVp switching such that the total movement (e.g., the sum of the movement) at each of the different spectra is less than $2\pi$. Alternatively, the source of the MSXT imaging system may include a single source with fast kVp switching, with the MSXT imaging system performing the fast kVp switching such that the total movement (e.g., the sum of the movement) at each of the different spectra is less than $2\pi$. For example, the MSXT imaging system may perform the fast kVp switching (generating the source output at the first and second spectra) while generating relative movement greater than 180° but less than 360°. As another example, the MSXT imaging system may perform the fast kVp switching (generating the source output at the first and second spectra) while generating relative movement greater than 90° but less than 180°. As still another example, the MSXT imaging system may perform the fast kVp switching (generating the source output at the first and second spectra) while generating relative movement greater than 45° but less than 90°.

In a third illustrative embodiment, the source includes a filter in order to generate the light at the different spectra. The filter may be an active filter (e.g., controllable by a central processor of the MSXT imaging system) or may be a passive filter (e.g., not controllable by a central processor of the MSXT imaging system). Any type of filter known in the art may be used. Regardless of the filter type, the source in combination with the filter generates the output at the different spectra. Further, the MSXT imaging system may activate the source such that during the relative movement, the data generated comprises the limited data set, as discussed above.

As another example, the MSXT imaging system may include multiple sources (e.g., a first source configured to output light at the first spectra and a second source configured to output light at the second spectra), with the MSXT imaging system controlling the multiple sources such that light output is at the different spectra during the relative movement of less than $2\pi$. Thus, in one implementation, the MSXT imaging system may activate the multiple sources at least partly simultaneously. Alternatively, the MSXT imaging system may activate the multiple sources serially. Regardless, the activation of the multiple sources is such that the different spectra during the relative movement is each less than $2\pi$.

As discussed above, in the multiple source implementation, the activation of the source may be less than $2\pi$ for each spectra. However, the relative movement may be less than $2\pi$ or may be $2\pi$ or greater. In the example of relative movement which is less than $2\pi$, the source may likewise be activated for less than $2\pi$ (e.g., the activation of the source may be co-extensive with the relative movement or may be less than the relative movement). In the example of relative movement that is $2\pi$ or greater, the activation of the source is such that the data generated is for relative movement that is less than $2\pi$. In this regard, the relative movement may be more or less than $2\pi$. However, the activation of the source during the relative movement is such that the data collected is less than $2\pi$ of the relative movement. Further, various types of sources are contemplated, such as sources that generate a fan beam or sources that generate a cone beam. Thus, any discussion below directed to fan beams may equally be applied to cone beams or other source outputs.

In one embodiment, the MSXT imaging system may control the detectors in order for the MSXT imaging system to obtain the limited data set. As one example, activation of detectors and/or control of filters associated with the detectors may be used in order to obtain the limited data set. For example, with a source generating a fan beam, the detectors may be positioned in a curve along the fan beam. In this example, the MSXT imaging system may use a filter for one part of the output of the fan beam such that a first portion (e.g., a first ½) of the fan beam is at the first spectrum, and a second portion (e.g., a second ½) of the fan beam is at the second spectrum. At the detector, there is a detector response. If a change of the system is desired, the source may be changed (such as via filters), the detectors may be changed (e.g., change the range of the spectra sensed), or both. Alternatively, the MSXT imaging system may have multiple sets of detectors, which may be controlled in order to obtain the limited data set. The MSXT imaging system can also control relative movement of the source(s), detector(s), and/or patient in order for the MSXT imaging system to obtain the limited data set. Thus, the MSXT imaging system controls one or more of the source(s), detector(s), and relative movement of system components to obtain the limited data set.

In another implementation, the MSXT imaging system may use a methodology in order to generate an image with the limited data set. The methodology can include accessing a data model of multi-spectral imaging, performing a transformation on the model in order to apply a convex optimization program, and using a convex optimization program to solve the imaging problem. Various data models may be used. In one implementation, a non-linear data model is used. Various non-linear data models are contemplated, such as a continuous-to-discrete (CD)-data model or a discrete-to-discrete (DD)-data model. Other data models can be used in alternative embodiments. Further, a transformation may be performed. One example transformation involves linearization of the data model. In one particular implementation, the non-linear data model may be partly linear and partly non-linear. The transformation may involve linearizing the part of the data model that is non-linear. In addition, a correction is optionally applied to compensate for the transformation of the model. In the example of linearization, a compensation to linearization of the model may be applied, with the compensation being iteratively performed.

As discussed above, FIG. 1A depicts a single-kVp switch imaging technique in which there is one rotation for the low kVp and another rotation for the high kVp in accordance with an illustrative embodiment. The system utilized in FIG. 1A is a representation of a full-scan configuration. In particular, FIG. 1A illustrates a standard, full-scan configuration in which each data set is collected for spectrum s at views uniformly distributed over $2\pi$. As shown in FIG. 1A, reference numeral 100 indicates the thin line for the low-kVp scan and reference numeral 110 indicates the thick line for the high-kVp scan.

Figure 1B:
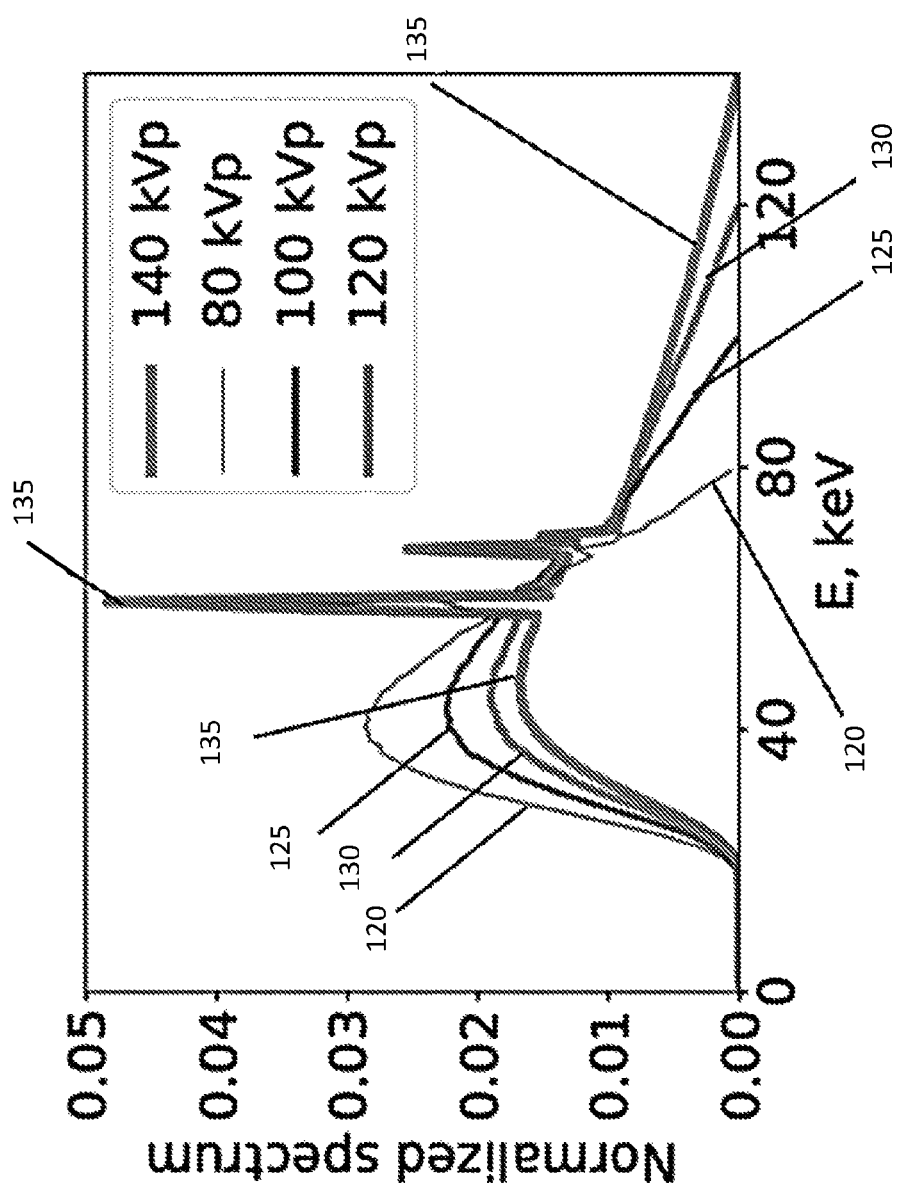
FIG. 1B is a graph showing multiple normalized spectral including 80 kVp (120), 100 kVp (125), 120 kVp (130), and 140 kVp (135) in accordance with an illustrative embodiment.

FIG. 1B is a graph showing multiple normalized spectral including 80 kVp (120), 100 kVp (125), 120 kVp (130), and 140 kVp (135) in accordance with an illustrative embodiment. Though 4 spectra are shown, fewer or greater numbers of spectra are contemplated, such as 2, 3, 5, 6, etc. As discussed below, various low-kVp spectrum (such as 80 kVp (120)) and high-kVp spectrum (such as 140 kVp (135)) may be used in the proposed system. As shown in the FIG. 1B, spectra 120, 125, 130, 135 are not delta functions. In one implementation, the methodology disclosed takes into consideration that the spectra are not delta functions, which contributes to the non-linearity of the data models, as discussed in more detail below.

Figure 26:
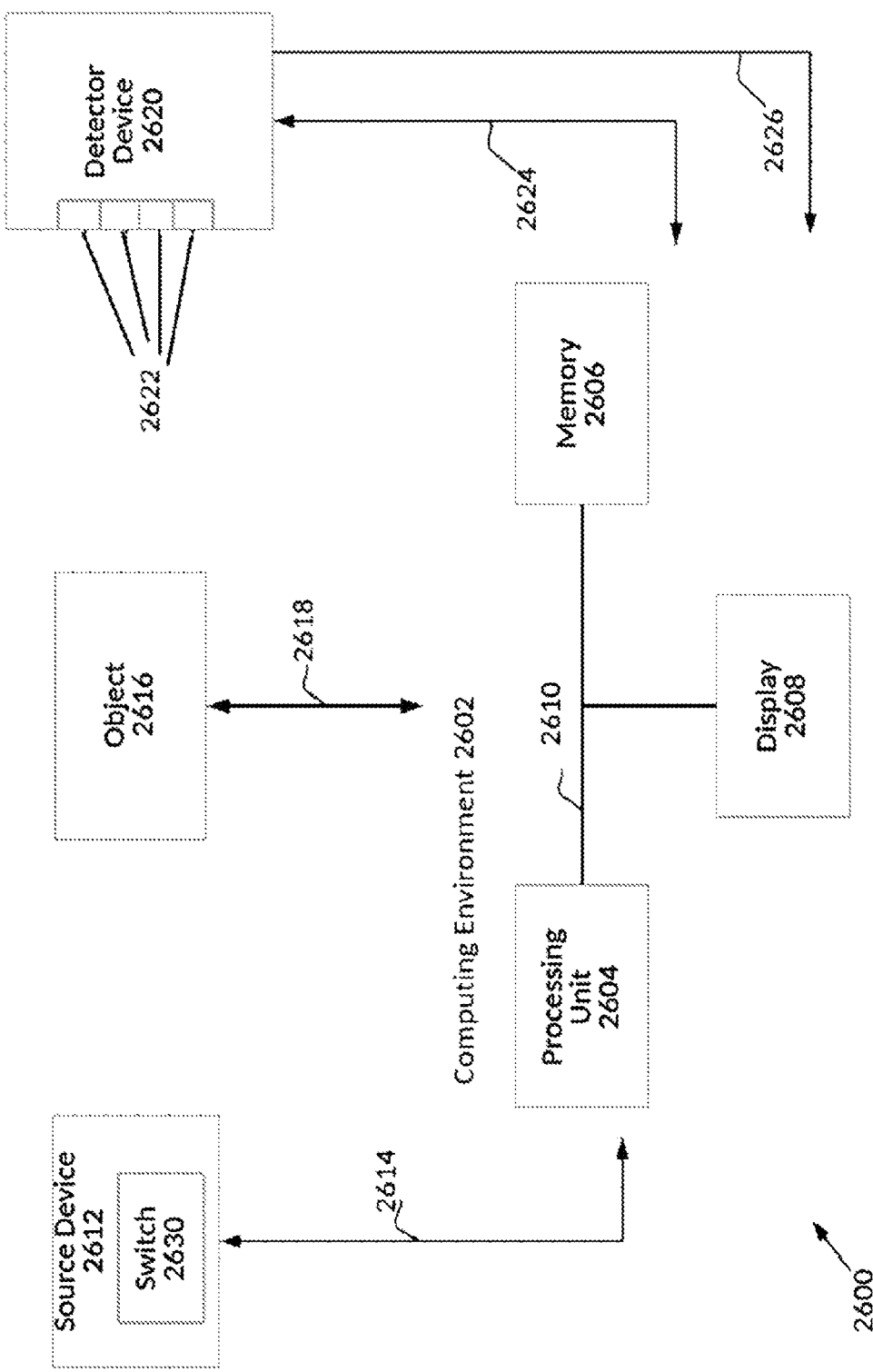
FIG. 26 depicts an MSXT imaging system in accordance with an illustrative embodiment.

FIG. 26 depicts an MSXT imaging system 2600 in accordance with an illustrative embodiment. In alternative embodiments, the MSXT imaging system 2600 may include fewer, additional, and/or different components. The MSXT imaging system 2600 includes a general purpose computing device in the form of a computing environment 2602, including a processing unit 2604, a system memory 2606, and display 2608. A system bus 2610 couples various system components of the computing environment 2602, including the processing unit, 2604, the system memory 2606, and the display 2608. The processing unit 2604 may perform arithmetic, logic, and/or control operations by accessing system memory 2606. For example, the processing unit 2604 may control the various system components to acquire data for imaging and may process the acquired data to generate an image. Specifically, the processing unit 2604 may control the source device 2612, the detector device 2620, and/or relative movement of the source device 2612, the detector device 2620, or the object 2626 through one or more motors (not shown). Alternatively, different system processors, or different devices may control the various system components to acquire data for imaging and may process the acquired data to generate an image. FIG. 26 illustrates one example of an MSXT imaging system. Other types of imaging systems are disclosed in: U.S. Pat. Nos. 7,394,923; 7,444,011; 8,121,245; 8,923,587; and 9,613,442. U.S. Pat. Nos. 7,394,923; 7,444,011; 8,121,245; 8,923,587; and 9,613,442, each of which are incorporated by reference herein in their entirety.

The system memory 2606 may store information and/or instructions for use in combination with processing unit 2604. For example, the system memory 2606 may store computer readable instructions, data structures, program modules or the like for operation of the imaging system 2600, including, for example, control of movement of any of the source, object, and detector and control of the functionality of the source and the detector. Further, the system memory 2606 may store data obtained from detector device 2620 and may process the data for presentation on the display 2608, as discussed in more detail below. The system memory 2606 may include volatile and non-volatile memory, such as random access memory (RAM) and read only memory (ROM). It should be appreciated by those skilled in the art that other types of computer readable media which can store data that is accessible by a computer, such as magnetic cassettes, flash memory cards, random access memories, read only memories, and the like, may also be used. A user may enter commands and/or information, as discussed below, into the computing environment 2602 through input devices such as a mouse and keyboard (not shown) that form a user interface. The commands and/or information may be used to control operation of the imaging system, including acquisition of data and processing of data.

FIG. 26 further depicts source device 2612 in communication with computing environment 2602 via line 2614. As discussed above, source device 2612 may be stationary or may move relative to any one, or both, of object 2616 and detector device 2620. Source device 2612 may also be configured to generate one or more spectra as discussed above. Further, source device 2612 includes a switch 2630. Switch 2630 is configured to perform the slow kVp switching or fast kVp switching under control by computing environment 2602. Further, source device 2612 may have associated therewith one or more filters (not shown), as discussed above. Line 2614 may also be used by processing unit 2604 to control movement of source device 2612, such as by sending commands to a motor (not shown) to move all or a part of source device 2612. For example, if the source device 2612 is an X-ray tube, the motor may move the entire X-ray tube relative to one, or both of, object 2616 and detector device 2620. Alternatively, the X-ray tube may remain stationary with a reflector revolving using the motor. In this manner, the beam emanating from the X-ray tube may be moved by bouncing the beam off the revolving reflector and toward object 2616. Although FIG. 26 illustrates a single source device, the MSXT imaging system 2600 may include one or more source devices, depending on the embodiment.

The source device 2612 may be any device which generates a signal that can be received by detector device 2620. The source device 2612 selected for imaging system 2600 may depend on the type of imaging performed by imaging system 2600. For example, source device 2612 may generate electromagnetic radiation in any frequency range, such as gamma rays, x-rays, visible light, microwaves, and radio/tv waves. In an illustrative embodiment, source device 2612 is an X-ray source that generates X-rays, or a radio frequency (RF) source that generates radio waves at one or more spectra. Source device 2612 may also generate other types of signals such as magnetic fields, mechanical waves (e.g., sound waves), heat, particles (e.g., electron, proton, neutron), or the like. Though a source device 2612 is depicted in imaging system 2600, it is noted that certain types of imaging systems do not utilize an external source, such as a positron emission tomography (PET) scanner.

FIG. 26 also depicts object 2616. Object 2616 may be any type of Region of Interest (ROI) or anything that is capable of being scanned, such as a living organism (e.g., human or animal) or a non-living object (e.g., a piece of luggage, a cargo container, food, an ocean, underground the earth, etc.). The position of the object may be stationary or may move relative to any one, or both, of source device 2612 and detector device 2620. Line 2618 can be a control line used to control movement of object 2616, such as by sending commands to a motor (not shown) to move object 2616. Any part, or all, of object 2616 may be imaged using imaging system 2600. Further, the object may ingest or be injected with a substance, such as a contrast agent, which may assist in imaging a part or all of object 2616. As shown in FIG. 26, source device 2612 is external to object 2616. Alternatively, source device 2612 may be internal to object 2616.

FIG. 26 further shows detector device 2620 communicating with computing environment 2602 via lines 2624 and 2626. Detector device 2620 may include a line of individual detectors 2622. Alternatively, multiple lines of detectors may be used to form detector device 2620. In this regard, the MSXT imaging system 2600 may include one or more detectors. Line 2624 represents a control line whereby the processing unit is able to control at least one characteristic of detector device 2620. As one example, line 2624 may control the activation of detector device 2620. Additionally, line 2624 may control one or more filters (not shown) associated with detector device 2620. Line 2626 may also be a data transmission line through which data sensed from the detectors 2622 is sent to computing environment 2602 for processing by processing unit 2604.

Detector device 2620 be any type of detector which senses any datum, such as electromagnetic radiation from any frequency range (such as X-rays in multiple spectra), magnetic fields, sound waves, heat, or the like. For example, for a 2-dimensional detector (flat-panel imager), detector device 2620 may include one row of detectors for fan beam geometry, four rows of detectors for quasi-fan-beam geometry, or more than four rows of detectors for cone-beam geometry. Detector device 2620 may be stationary or may move relative to any one, or both, of source device 2612 and object 2616. Line 2624 may also be used to control movement of detector device 2620, such as by sending commands to a motor (not shown) to move all or a part of detector device 2620. As shown in FIG. 26, detector device 2620 is external to object 2616. Alternatively, detector device 2620 may be internal to object 2616. Thus, both source device 2612 and detector device 2620 may be internal or external to the object, depending on the type of object being scanned. Moreover, source device 2612 may be internal and detector device 2620 may be external to object 2616, or source device 2612 may be external and detector device 2620 may be internal to object 2616. For example a dental image of a patient may be acquired with an external source and a detector held in the mouth of a patient.

In one example, the detector device 2620 may be modeled as a straight-line array of 512 detector bins, which may be large enough so that the field-of-view is the circle inscribed in a 256×256 imaging array. The MSXT measurements may be related to the path integral of the x-ray attenuation coefficient along the rays defined by the source spot and individual detector bins.

In one implementation, the computing environment 2602, such as processing unit 2604, may be in communication with the source device 2612, the object 2616 and/or the detector device 2620. The processing unit 2604 may be configured to control at least one of the one or more source devices, control the one or more detectors or the ROI such that the ROI moves relative to the one or more source devices and the one or more detectors, control the one or more source devices such that the one or more source devices output light at the first spectrum or the second spectrum for less than $2\pi$ of movement of the ROI relative to the one or more source devices and the one or more detectors, store ROI data generated from the one or more detectors sensing light from the first spectrum and the second spectrum (the ROI data being limited to less than $2\pi$ of movement of the ROI relative to the one or more source devices and the one or more detectors for at least one of the first spectrum and the second spectrum), and generate an estimated image of the ROI based on ROI data. The processing unit 2604 can take the form of processing circuitry, a microprocessor or processor, and a computer-readable medium that stores computer-readable program code (e.g., software or firmware) executable by the (micro)processor, logic gates, switches, an application specific integrated circuit (ASIC), a programmable logic controller, and an embedded microcontroller, for example. The processing unit 2604 can be configured with hardware and/or firmware to perform the various functions described below and shown in the pseudo code. Also, some of the components described as being internal to the processing unit 2604 can also be stored external to the processing unit 2604, and other components can be used.

As an example, the processing unit 2604 may control movement of any of the source device 2612, the detector device 2620, and/or the object 2616 in order to move the object 2616 relative to the source device 2612 and the detector device 2620. Further, the processing unit 2604 may control the source device 2612 such that the source device 2612 outputs light such as in the scan configurations illustrated in FIGS. 2-8, which results in light output by the source device 2612 at the first spectrum or the second spectrum for less than $2\pi$ of movement of the object 2616 relative to the source device 2612 and the detector device 2620. Responsive to the light generated by the source device 2612, the detector device 2620 may generate data, such as ROI data, for storage. Because the light output by the source device 2612 is limited (e.g., being less than $2\pi$ of movement of the object 2616 relative to the source device 2612 and the detector device 2620), the ROI data stored is limited to less than $2\pi$ of movement of the object 2616 relative to the source device 2612 and the detector device 2620 for the first spectrum and the second spectrum. Finally, the stored ROI data may be used to generate the estimated image of the object, as discussed in more detail below.

Figure 2:
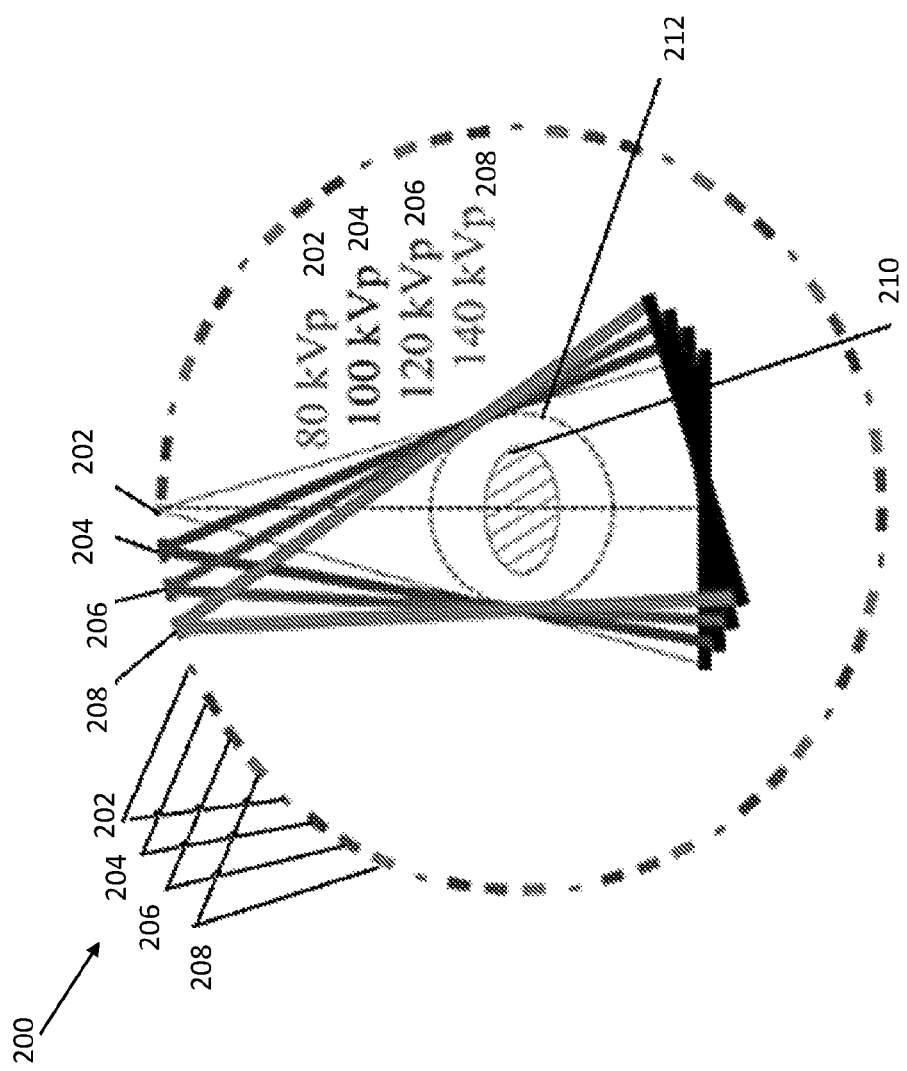
FIG. 2 illustrates an example of a sparse-view configuration in which multi-spectral data are collected at multi sets of interlaced sparse views over an angular range of any value between 180 degrees and 360 degrees in accordance with an illustrative embodiment.

FIGS. 2-8 illustrate representations of different limited data scans. As discussed above, the limited data scans may be based on control of one or more of the source(s), the detector(s), and the relative movement of the object. In particular, FIG. 2 illustrates an example of a sparse-view configuration 200 in which multi-spectral data are collected at multi sets of interlaced sparse views over an angular range of any value between 180 degrees and 360 degrees in accordance with an illustrative embodiment. In this regard, FIG. 2 illustrates an example of controlling the source in generating the limited data scan. The dashed circle 212 indicates the FOV of the scanner, in which the imaged object (elliptical region 210) is enclosed. As shown in FIG. 2, there are 4 sets of interlaced sparse views over an angular range of $2\pi$ (i.e., 360 degrees). For example, the source is configured to generate the different spectra for: 80 kVp (202);

100 kVp (204); 120 kVp (206); and 140 kVp (208). As shown in FIG. 2, the different spectra are generated in a sequence, such as 80 kVp (202), 120 kVp (206), 100 kVp (204), and 140 kVp (208), with the sequence repeating over the entire angular range of 2π.

In one implementation, there is no distance (e.g., 0°) between the different spectra. Alternatively, there may be a distance between the different spectra. For example, the degree distance may be 0.5°, 0.5°-1°, 1°, 1°-5°; 5°, 5°-10°, etc. Further, the distance (i.e., number of degrees) between increments of the different spectra may be uniform across all of the different spectra. Alternatively, the degree distance between the different spectra may be different. Fewer (such as 2 or 3) or greater (such as 5, 6 or more) interlaced sparse views are also contemplated in the embodiment of FIG. 2. Further, the angular range may be 2π, such as illustrated in FIG. 2. Alternatively, the angular range may be less than 2π, such as between 270° and 2π, such as between 180° and 2π, and such as between 180° and 270°. Further, the sequence may repeat in the different angular ranges less than 2π, such as between 270° and 2π, such as between 180° and 2π, such as between 180° and 270°, etc.

Figure 3:
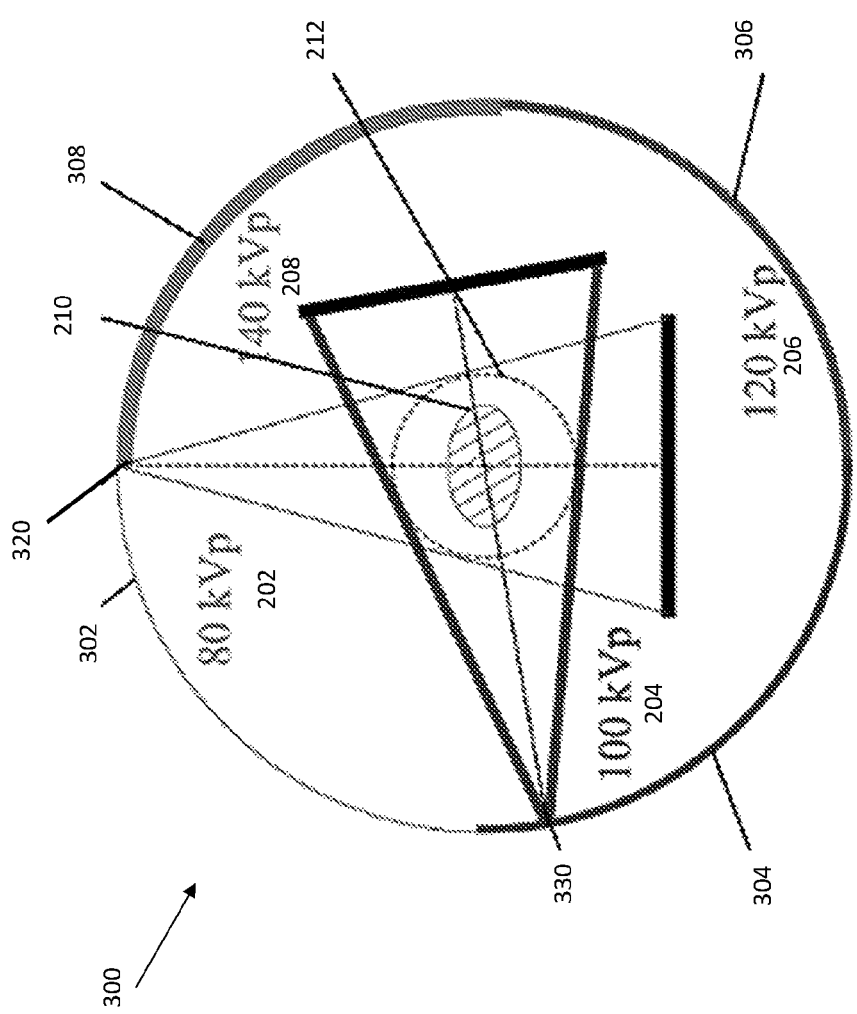
FIG. 3 illustrates a limited-angular-range configuration in which multi-spectral data are collected at multiple sets of limited-angular ranges over an angular range of any value between 180 degrees to 360 degrees in accordance with an illustrative embodiment.

FIG. 3 illustrates a limited-angular-range configuration 300 in which multi-spectral data are collected at multiple sets of limited-angular ranges over an angular range of any value between 180 degrees to 360 degrees in accordance with an illustrative embodiment. As shown in FIG. 3, there are 4 sets of sparse views over an angular range of 2π. For example, each of 80 kVp (302), 100 kVp (304), 120 kVp (306), and 140 kVp (308) includes an associated continuous angular range. Thus, FIG. 3 illustrates another example of controlling the source in generating the limited data scan. As shown in FIG. 3, the different spectra are equally divided across 2π, with 90° for each of the 4 spectra. In this regard, in one implementation, the angular range (e.g., 2π) may be divided equally across the different spectra. Alternatively, the angular range may be divided unequally across the different spectra. Fewer (such as 2 or 3) or greater (such as 5, 6 or more) interlaced sparse views are contemplated in other embodiments. Further, the angular range may be 2π, or alternatively less than 2π, such as between 270° and 2π, such as between 180° and 2π, such as between 180° and 270°, etc. As shown in FIG. 3, there are two positions at different spectra shown, with 320 at 80 kVp and with 330 at 100 kVp.

Figure 4:
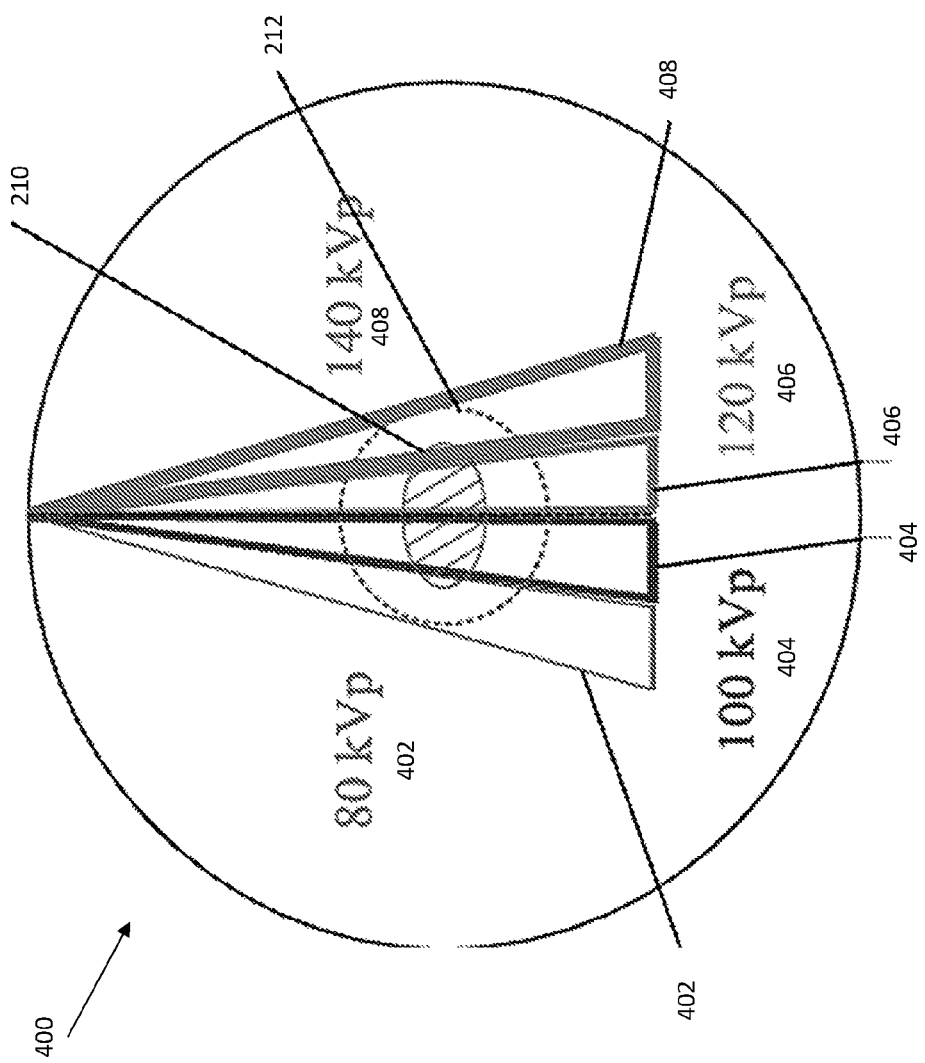
FIG. 4 illustrates a block configuration in which multi-spectral data are collected at multiple sets of detector blocks over an angular range of any value $2\pi$ or less in accordance with an illustrative embodiment.

FIG. 4 illustrates a block configuration in which multi-spectral data are collected at multiple sets of detector blocks over an angular range of any value 2π or less in accordance with an illustrative embodiment. For example, the angular range may be 2π, between 180° to 2π, between 180° to 270°, etc. In this embodiment, a row of detectors may detect different spectra, such as at 80 kVp (402), 100 kVp (404), 120 kVp (406), and 140 kVp (408). FIG. 4 illustrates this at a point in the 2π (circumference. In this regard, FIG. 4 illustrates an example of controlling the detector(s) in generating the limited data scan. As shown, the data at the different spectra are collected at least partly simultaneously with different detectors detecting the different spectra (e.g., at 80 kVp (402), 100 kVp (404), 120 kVp (406), and 140 kVp (408)). In an alternative implementation, all of the detectors may detect at one spectrum, and then sequence through the different spectra during the relative movement of the source(s)/detector(s) to the object (such as over 2π or over less than 2π). As one example, the detectors may be configured to sense one spectrum. Thereafter, relative movement may occur, with the detectors thereafter configured to sense another spectrum. This sequence of relative movement and changing of the configuration of the detectors may be performed iteratively (e.g., stepping through the different spectra).

Figure 5:
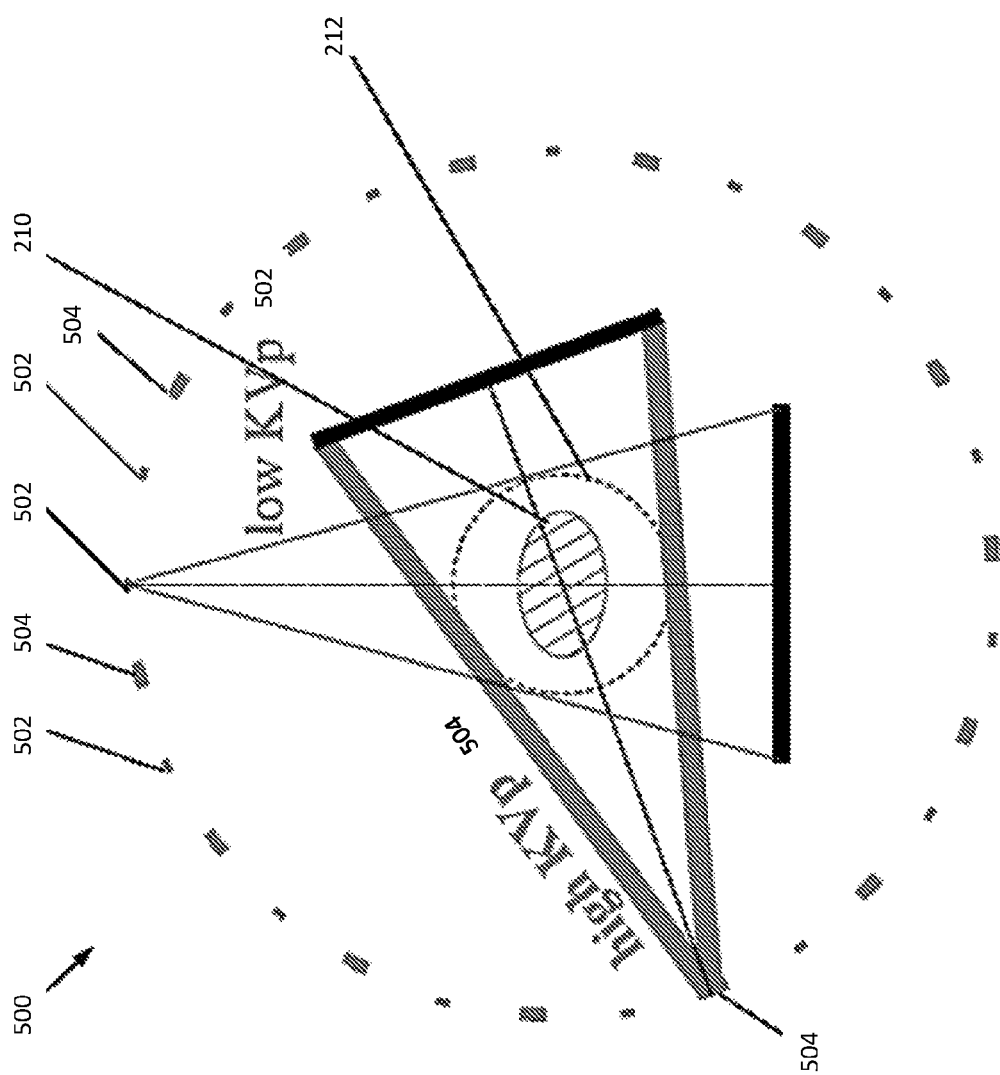
FIG. 5 is a representation of a sparse-view configuration in which low-kVp and high-kVp data are collected at two sets of interlaced sparse views uniformly distributed over $2\pi$ in accordance with an illustrative embodiment.

FIG. 5 is a representation of a sparse-view configuration 500 in which low-kVp and high-kVp data are collected at two sets of interlaced sparse views uniformly distributed over 2π in accordance with an illustrative embodiment. In one implementation, the source outputting low-kVp 502 and outputting high-kVp 504 may alternate, such as over an angular range (e.g., 2π, between 270° and 2π, between 180° and 2n; between 180° and 270°). In particular, a source outputting low-kVp 502 and outputting high-kVp 504 onto object 306 is illustrated. As shown in FIG. 5, there are gaps between the interlaced sparse views. The gaps may be 0.5°, 0.5°-1°, 1°, 1°-5°, 5°, 5°-10°, etc. Further, the degree distance between the different spectra may be the same between each of the different spectra or different as discussed above. Although not shown in FIG. 5, in an alternate implementation, there may be no distance between the interlaced sparse views. In another implementation, some of the interlaced sparse views may have a gap therebetween and other interlaced sparse views may have no gap. Thus, the angular range for each of the low-kVp and high-kVp may be added to result in respective total angular ranges for each of the low-kVp and high-kVp.

Figure 6:
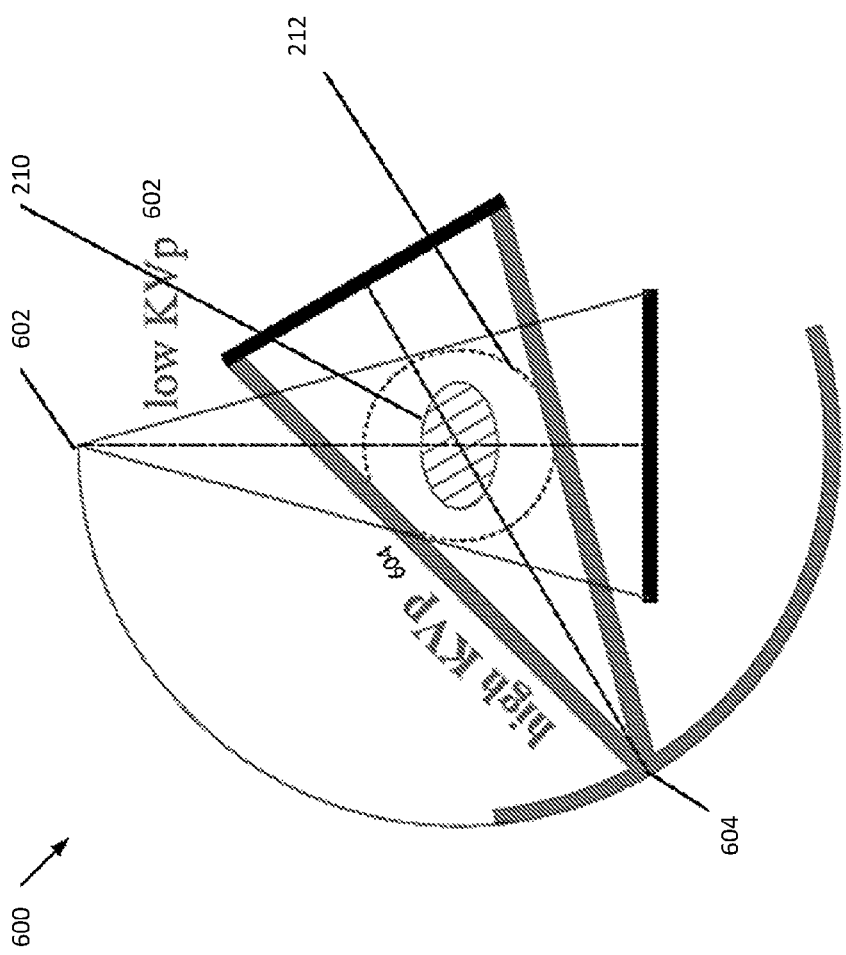
FIG. 6 is a representation of a limited-angular-range configuration 600 in which low-kVp and high-kVp data (from a source outputting low-kVp 602 and outputting high-kVp 604 onto object 306) are collected over the two adjacent limited-angular ranges in accordance with an illustrative embodiment.

FIG. 6 is a representation of a limited-angular-range configuration 600 in which low-kVp and high-kVp data (from a source outputting low-kVp 602 and outputting high-kVp 604 onto object 306) are collected over the two adjacent limited-angular ranges in accordance with an illustrative embodiment. The non-standard configurations illustrated in FIGS. 5-6 involve varying angular coverages, and are referred to as the sparse-view and limited-angular-range configurations, respectively. In FIG. 5, low- and high-kVp data are collected at two sets of interlaced sparse views uniformly distributed over 2π. In particular, the light generated by the source outputting low-kVp 502 is interspersed between the light generated by the source outputting high-kVp 504. Further, the non-contiguous segments where the light generated by the source outputting low-kVp 502 may be summed, as discussed above. This sum is less than 2π. Likewise, the non-contiguous segments where the light generated by the source outputting high-kVp 504 may be summed, with the sum being less than 2π. In FIG. 6, low- and high-kVp data are collected over two adjacent continuous limited angular-ranges. As shown, the angular range for the low-kVp 602 (i.e., the thin line) is approximately 90°, whereas the angular range for the high-kVp 604 (i.e., the thick line) is greater than 90°.

FIG. 6 further illustrates that the angular range for the low-kVp and the angular range for the high-kVp do not overlap. Alternatively, the angular range for the low-kVp may at least partly overlap with the angular range for the high-kVp. For example, the angular range for the low-kVp may be 0° to 225°, and the angular range for the high-kVp may be 225° to 90°. In an alternative implementation, a short+short scan configuration may be used in which each short scan is greater than 180° and less than 360° for the dual-energy data sets collected using the low-kVp and high-kVp X-rays. Specifically, the angular range for the low-kVp may be greater than 180°, whereas the angular range for the high-kVp may be greater than 180°. In another implementation, a half+half scan configuration may be used in which each half scan is equal to 90° for the dual-energy data sets collected using the low-kVp and high-kVp X-rays. As shown, the angular range for the low-kVp is equal to 180°, and the angular range for the high-kVp is equal to 180°. In this regard, the short+short scan configuration and the half+half scan configuration are further specific examples of limited-angular range configurations.

As discussed above, the MSXT imaging system may use a scan configuration that is a partial-angular-scan configuration in which each of the two dual-energy data sets is acquired for an object only over an angular range considerably less than $2\pi$. Because the reduced angular range is less than $2\pi$, a partial-angular-scan configuration can be exploited for possibly reducing imaging time and dose of a full-scan configuration. Further, a partial-angular-scan configuration can readily be realized on standard CT scanners without additional hardware simply by use of the standard single-kVp-switch technique, which is available on many existing CT scanners.

As an example, three parameters, $\alpha_0$, $\alpha_1$, and $\alpha_2$ may be used to specify a partial-angular-scan configuration, where $\alpha_0$ and $\alpha_2$ denote the starting and ending angles of the X-ray tube, and $\alpha_1$ is the angle at which the X-ray tube switches its kVp. The system therefore collects two sets of dual-energy data over angular ranges $\alpha_1$-$\alpha_0$ and $\alpha_2$-$\alpha_1$. In a full-scan configuration, $\alpha_1$-$\alpha_0$=$\alpha_2$-$\alpha_1$=$2\pi$, whereas in a partial-angular-scan configuration, $\alpha_1$-$\alpha_0$<$2\pi$ and $\alpha_2$-$\alpha_1$<$2\pi$. Further, two fast partial-angular-scan configurations may be used for dual-energy CT. In addition, the MSXT can control the tube such that it rotates a short-scan range in one kVp, before switching to another kVp setting to rotate for another short-scan range. Thus, two sets of dual-energy data may be acquired with $\alpha_0$=0, $\alpha_1$=$\pi$+$\gamma_m$, and $\alpha_2$=$2\pi$+$2\gamma_m$, where $\gamma_m$ is the fan angle of the CT scanner. Alternatively, the MSXT may control the tube such that it rotates according to: $\alpha_0$=0, $\alpha_1$=$\pi$, and $\alpha_2$=$2\pi$. The X-ray tube may be switched from one kVp to another kVp at $\alpha_1$=$\pi$, and the angular range of each kVp scan covers one half of a full-rotation scan. As discussed in more detail below, the methodology can use a heuristic algorithm for reconstructing basis and monochromatic images from dual-energy data collected with full-, short- and half-scan configurations through numerically solving the program.

Figure 7:
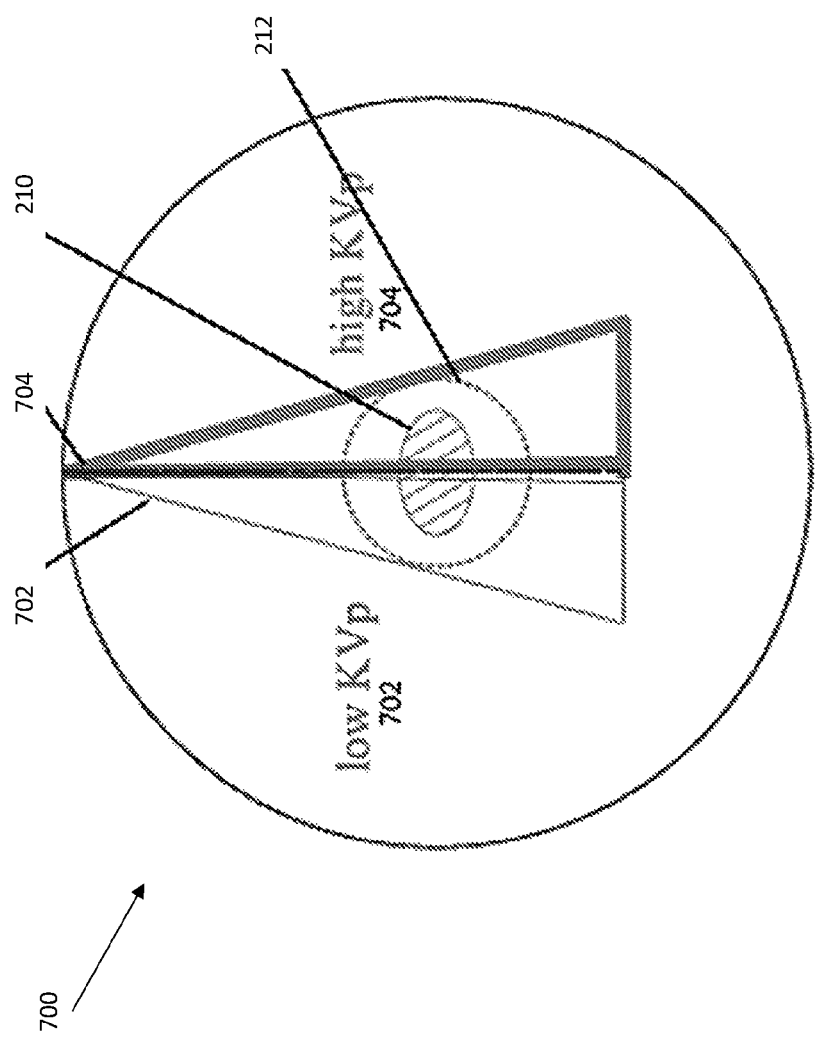
FIG. 7 is a representation of a split-illumination configuration in which low-kVp and high-kVp data are collected with two adjacent illumination coverage of low-kVp and high-kVp at each of 640 views uniformly distributed over $2\pi$ in accordance with an illustrative embodiment.
Figure 8:
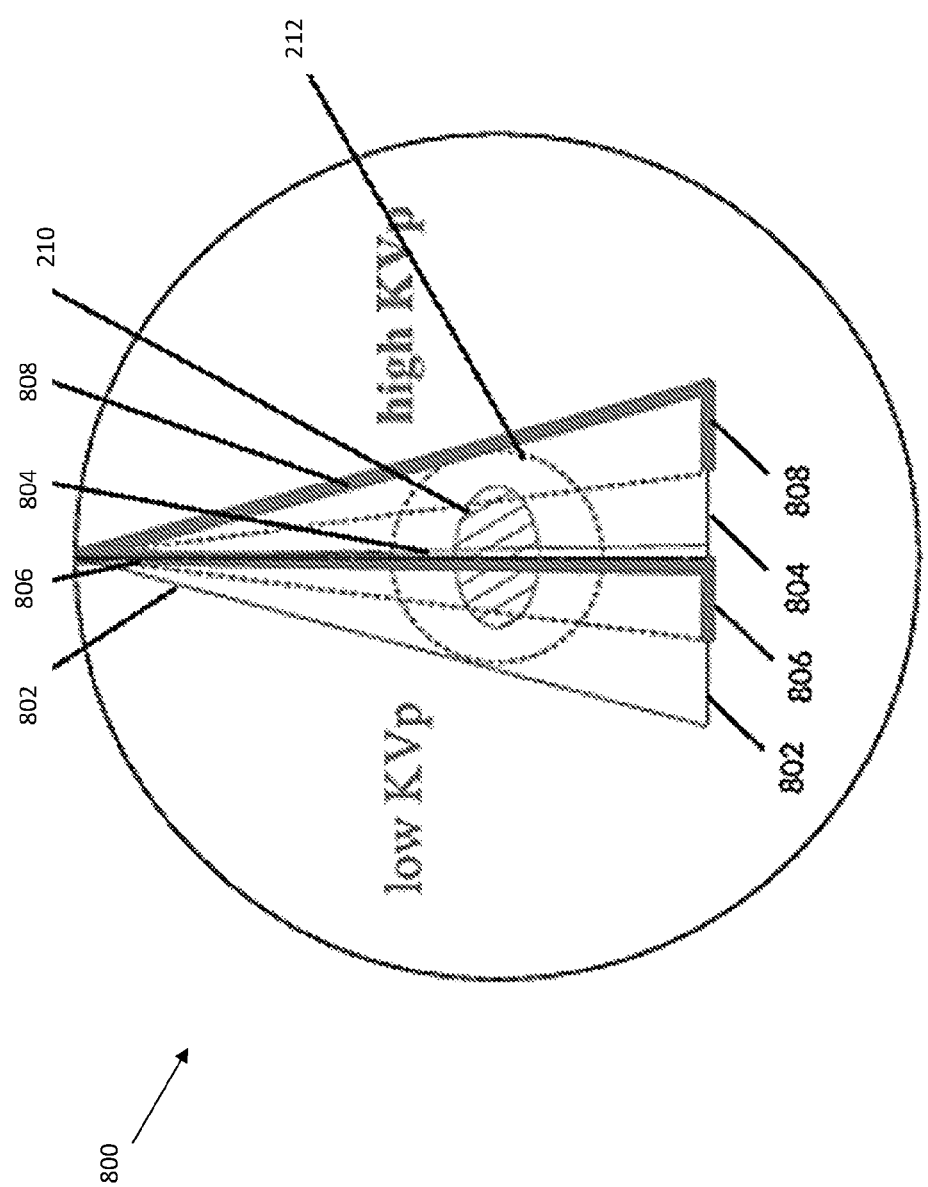
FIG. 8 is a representation of a block-illumination configuration in which low-kVp and high-kVp data are collected with multiple adjacent alternating illumination coverage of low-kVp and high-kVp at each of 640 views uniformly distributed over $2\pi$ in accordance with an illustrative embodiment.

FIG. 7 is a representation of a split-illumination configuration 700 in which low-kVp and high-kVp data are collected with two adjacent illumination coverage of low-kVp 702 and high-kVp 704 at each of 640 views uniformly distributed over $2\pi$ in accordance with an illustrative embodiment. In particular, a low-kVp illumination (702) and a high-kVp illumination (704) are directed onto object 210, at a plurality of views (such as the 640 views uniformly distributed over $2\pi$). FIG. 8 is a representation of a block-illumination configuration 800 in which low-kVp and high-kVp data are collected with multiple adjacent alternating illumination coverage of low-kVp 802, 804 and high-kVp 806, 808 at each of 640 views uniformly distributed over $2\pi$ in accordance with an illustrative embodiment. For example, a first low-kVp illumination (802), a first high-kVp illumination (806), a second low-kVp illumination (804), a second high-kVp illumination (808) are directed onto object 210 at a plurality of views (such as the 640 views uniformly distributed over $2\pi$). Alternatively, a different number of views may be used in the implementations of FIGS. 7 and 8.

Two non-standard configurations are shown in FIGS. 7-8, which involve varying illumination coverage. These configurations are referred to as the split- and block-illumination configurations, respectively. In the configurations, low- and high-kVp data are collected, respectively, with two adjacent and multiple adjacent alternating illumination coverages at each of 640 views uniformly distributed over $2\pi$.

Alternatively, low- and high-kVp data are collected, respectively, with two adjacent and multiple adjacent alternating illumination coverages at views over less than $2\pi$ (such as uniformly distributed over 90°, between 90° to 180°, between 180° to 270°, between 270° to 360°, etc.). The configurations may be achieved through, for example, the use of a beam blocker in front of the X-ray source and/or detector blocks with different energy responses. Thus, these are examples of controlling one or both of the source(s) or the detector(s) in order to achieve the different configurations.

As discussed above, a one-step inversion approach may be used to reconstruct basis and monochromatic images in MSXT for a variety of scan configurations or systems of potential practical significance. In particular, an optimization-based one-step inversion approach may use a methodology to reconstruct basis images through solving numerically a non-convex optimization program based upon the non-linear data model in MSXT. In particular, the methodology may be used with non-standard scanning configurations (such as disclosed in FIGS. 2-8) involving no or minimum hardware modification. In one implementation, the one-step inversion approach may include: accessing one or more non-linear data models; accessing a non-convex optimization program; using an algorithm for numerically for solving the non-convex optimization program; and determining one or more convergence conditions. Discussed below are the study design (including spectra, phantoms, and configurations), verification and characterization studies of one implementation of the methodology, and application of the methodology (including applying the methodology to non-standard scanning configurations of practical implications).

As an initial matter, a data model may be used or accessed by the system. In one implementation, one or more non-linear data models may be accessed. Several non-linear data models are contemplated, with examples of non-linear data models including: continuous-to-discrete (CD)-data models; and discrete-to-discrete (DD)-data models.

In using the CD-data model for MSXT, one seeks to determine X-ray linear attenuation coefficient $f(E, \vec{r})$ from knowledge of multiple transmission measurements. One may decompose $f(E, \vec{r})$, a function of X-ray photon energy E and spatial coordinates $\vec{r}$, into the form:

$$f(E, \vec{r}) = \Sigma_k \mu_k(E) b_k(\vec{r}), \qquad \text{Eq. 1:}$$

where $k \in \mathbb{Z}^+$, and $\mu_k(E)$ and $b_k(\vec{r})$ are referred to as decomposition coefficients and basis images. The decomposition can be e.g., material or interaction based depending upon how $\mu_k(E)$ is selected. Assuming that the decomposition coefficients are known, the problem of image reconstruction in MSXT may be simplified to the determination of the basis images, which are functions only of spatial variable $\vec{r}$. A material decomposition may be considered in which the mass-attenuation coefficient of the kth basis image material is selected as $\mu_k(E)$.

Letting $Q_j^{[s]}(E)$ denote the X-ray spectrum for ray j with spectrum s, and $I_j^{[s]}$ and $I_{0j}^{[s]}$ the transmission measurements for ray j in the presence and absence, respectively, of $f(E, \vec{r})$, one can define a data model as $\tilde{g}_j^{[s]} = -\ln(I_j^{[s]}/I_{0j}^{[s]})$, which can be written further as:

$$\tilde{g}_j^{[s]} = -\ln \int_0^\infty E \tilde{q}_j^{[s]}(E) \exp(-\int_0^\infty t f(E, \vec{r}_\lambda + t \hat{\beta})) \qquad \text{Eq. 2:}$$

$$= -\ln \int_0^\infty E \tilde{q}_j^{[s]}(E) \exp(-\Sigma_k \mu_k(E) \int_0^\infty t b_k(\vec{r}_\lambda + t \hat{\beta})), \qquad \text{Eq. 3:}$$

where $\vec{r}_\lambda$ denotes the source position, $\hat{\beta}$ the direction of ray j, s∈{1, . . . , S}, S the total number of X-ray spectra used, and $$\tilde{q}_j^{[s]}(E)=Q_j^{[s]}(E)(\int_0^\infty E Q_j^{[s]}(E))^{-1}, \qquad \text{Eq. 4:}$$

with the normalized spectral function satisfying $\int dE\ \tilde{q}_j^{[s]}(E)=1$. Spectrum function $\tilde{q}_j^{[s]}(E)$ can be ray-dependent in cases that a bow-tie filter is placed in front of the X-ray source and/or that multiple measurements can be made for a given ray, e.g., using multiple energy bins in a photon-counting detector.

Because $\tilde{q}_j^{[s]}(E)$, $\mu_k(E)$, and $b_k(\vec{r})$ are functions of continuous variable E or $\vec{r}$, and because $\tilde{g}_j^{[s]}$ for ray j is specified by discrete index j, one may refer to equation 2 as a continuous-to-discrete (CD)-data model, which is used for obtaining discrete-to-discrete (DD)-data models below. When $\tilde{q}_j^{[s]}(E)=\delta(E-E_0)$, the CD-data model becomes the conventional X-ray transform for ray j.

In practical CT imaging with spectrum s, measurements made at a discrete source position $j_\lambda^{[s]}$ form a two-dimensional (2D) array that includes rows and columns indexed by $j_u^{[s]}$ and $j_v^{[s]}$. By letting $N_\lambda^{[s]}$ denote the total number of discrete source positions and $N_u^{[s]}$ and $N_v^{[s]}$ the total numbers of rows and columns of the detector-measurement array at the source position, one can align all the measurements into a one-dimensional (1D) array in a concatenated form in the order of $j_u^{[s]}$, $j_v^{[s]}$, and $j_\lambda^{[s]}$, with elements indexed by $j=j_u^{[s]}+j_v^{[s]}\times N_u^{[s]}+j_\lambda^{[s]}\times N_v^{[s]}\times N_u^{[s]}$, $J^{[s]}=N_\lambda^{[s]}\times N_u^{[s]}\times N_v^{[s]}$, and $j\in\{0, \ldots, J^{[s]}-1\}$.

In a DD-data model, the energy space can be discretized uniformly with $E=m\Delta_E$, where $m\in\{1, \ldots, M\}$, and $\Delta_E$ is the energy sampling interval. The discretized form of the normalized spectrum function in equation 4 is defined as $q_{jm}^{[s]}=\Delta_E\ \tilde{q}_j^{[s]}(m\Delta_E)$ satisfying the normalization condition $\Sigma_m q_{jm}^{[s]}=1$. One can also consider a voxel-based representation of three-dimensional (3D) image space by discretizing evenly its x-, y-, and z-axis, with $x=x_0+i_x\Delta_x$, $y=y_0+i_y\Delta_y$, and $z=z_0+i_z\Delta_z$, where $i_x\in\{0, \ldots, N_x-1\}$, $i_y\in\{0, \ldots, N_y-1\}$, and $i_z\in\{0, \ldots, N_z-1\}$. $N_x$, $N_y$, and $N_z$ denote the total numbers of voxels, $\Delta_x$, $\Delta_y$, $\Delta_z$ the voxel sizes, and $x_0, y_0, z_0$ the starting positions along x, y, and z-axis, respectively. The voxels can be aligned into a 1D array of size $I=N_x\times N_y\times N_z$ in a concatenated form in the order of $i_x$, $i_y$, and $i_z$, indexed by $i=i_x+i_y\times N_x+i_z\times N_y\times N_z$.

For spectrum s, using equation 2 and the discrete image array, a DD-data model may be represented as:

$$g_j^{[s]}=-\ln \Sigma_m q_{jm}^{[s]} \exp(-\Sigma_i a_{ji}^{[s]} f_{im}'), \qquad \text{Eq. 5:}$$

where $j\in\{0, \ldots, J^{[s]}-1\}$, $i\in\{0, \ldots, I-1\}$, $a_{ji}^{[s]}$ denotes the intersection length of ray j with voxel i, $f_{im}'$ the discrete linear attenuation coefficient at energy m, and $$f_{im}'=\Sigma_{k\in Z^+} \mu_{km} b_{ki}, \qquad \text{Eq. 6:}$$

where $\mu_{km}=\mu_k(m\Delta_E)$, and $b_{ki}$ discrete basis image k at voxel i. Subscript i indicates that $f_{im}'$ and $b_{ki}$ are in the concatenated form described above.

When K basis images are considered, a discrete form of equation 1 may be:

$$f_{im}=\Sigma_k \mu_{km} b_{ki} \text{ and } f_{im}'=f_{im}+\Delta f_{im}, \qquad \text{Eq. 7:}$$

where $k\in\{1, \ldots, K\}$, and $\Delta f_{im}$ the difference between $f_{im}'$ and $f_{im}$. $f_{im}$ and $\Delta f_{im}$ may be referred to as the monochromatic image, and the image decomposition error within voxel i at energy m. Vector images $f_m'$ and $f_m$ of size I at energy m can be formed with elements $f_{im}$ and $f_{im}'$, respectively. Similarly, basis-image vector $b_k$ of size I can be assembled in which entry i is given by $b_{ki}$.

Ignoring decomposition error $\Delta f_{im}$ in equation 5, another DD-data model may be represented as:

$$g_j^{[s]}(b)=-\ln \Sigma_m q_{jm}^{[s]} \exp(-\Sigma_k \mu_{km} \Sigma_i a_{ji}^{[s]} b_{ki}), \qquad \text{Eq. 8:}$$

where $k\in\{1, \ldots, K\}$, and b denotes an aggregate basis-image vector formed by concatenating individual basis-image vectors $b_k$ in the ascending order of k. For simplicity, b is referred to as the basis image.

The reconstruction algorithm is designed based upon the DD-data model in equation 8 in the results described herein. When the algorithm is applied to data collected in a real experiment or generated by use of a data model (e.g., equation 5) other than equation 8, the data contain inconsistencies such as noise and/or decomposition error with the data model in equation 8.

Variable b in model data $g_j^{[s]}(b)$ indicates explicitly that the reconstruction task is to determine b from knowledge of data measured. Considering all of the measurements with spectrum s, vector $g^{[s]}(b)$ is formed of size $J^{[s]}$, with elements $g_j^{[s]}(b)$. An aggregate vector g(b) of model data can then be assembled by concatenating $g^{[s]}(b)$ in the ascending order of s. Additionally, $q_j^{[s]}$ of size M is used to denote a vector of discretized spectrum in which entry $q_{jm}^{[s]}$ indicates value of spectrum s at energy m for ray j. Let $g_{M\ j}^{[s]}$ denote the measured data for ray j with spectrum s, which can be used to form aggregate vector $g_M$ (i.e., the counterpart of model data g(b) as discussed above).

Further, the methodology may use a non-convex optimization program. Image reconstruction in MSXT is tantamount to the determination of basis image b by inverting the DD-data model in equation 8 from knowledge of measured data $g_M$, which can be formulated as a constrained optimization program in the form of:

$$b^* = \operatorname*{argmin}_b \Psi(b)\ \text{s.t.}\ \Phi(b; g_M) \le \varepsilon\ \&\ b \pm 0, \qquad \text{Eq. 9}$$

where data constraint parameter ε>0, and ± denotes the vector-form inequality, which requires all elements of b to be non-negative. The objective and data-fidelity functions may be designed as:

$$\Psi(b)=\Sigma_k \|b_k\|_{TV} \text{ and } \Phi(b; g_M)=D(g(b), g_M), \qquad \text{Eq. 10:}$$

where $\|\cdot\|_{TV}$ denotes the image total-variation (TV), defined as the $l_1$-norm of the gradient-magnitude image, i.e., $\|b_k\|_{TV}=\|(|\nabla b_k|)\|_1$, with $\nabla$ denoting the finite-differencing approximation to the gradient and $|\cdot|$ a spatial magnitude operator, and D(x,y) the data divergence, often in the form of $l_p$-norm or Kullback-Leibler (KL) divergence, between vectors x and y. One may consider a normalized $l_2$-norm of vector difference between model data g(b) and measured data $g_M$, i.e., $$D(g(b), g_M) = \left[\frac{\sum_s \|g^{[s]}(b)-g_M^{[s]}\|_2^2}{\sum_s \|g_M^{[s]}\|_2^2}\right]^{1/2}. \qquad \text{Eq. 11:}$$

Further, an algorithm may be used to numerically solve the non-convex program. Data divergence $D(g(b), g_M)$ is non-convex (NC) due to the non-linearity of the DD-data model, so is the optimization program in equations 9-11. In the absence of a mathematically exact solver for achieving the globally optimal solution of the non-convex optimization program, a heuristic algorithm may instead be used for numerically solving the program and may demonstrate its potential in enabling MSXT configurations of potential application significance.

As discussed above, various data models may be used. As one example, the DD-data model may be used, with the linear and non-linear contributions to the DD-data model analyzed. First, the mass-attenuation coefficient $\mu_{km}$ in equation 8 may be split into:

$$\mu_{km} = \bar{\mu}_{jk}^{[s]} + \mu_{jkm}^{[s]}, \text{ where} \qquad \text{Eq. 12:}$$

$$\bar{\mu}_{jk}^{[s]} = \Sigma_m q_{jm}^{[s]} \mu_{jm}, \text{ and } \Delta\mu_{jkm}^{[s]} = \mu_{km} - \bar{\mu}_{jk}^{[s]}. \qquad \text{Eq. 13:}$$

While $\bar{\mu}_{jk}^{[s]}$ is independent of energy as it is a spectrum-weighted average of $\mu_{km}$ over energy, $\Delta\mu_{jkm}^{[s]}$ remains energy dependent. Substitution of equation 12 into equation 8 yields:

$$g_j^{[s]}(b) = \bar{g}_j^{[s]}(b) + \Delta g_j^{[s]}(b), \qquad \text{Eq. 14:}$$

where $j \in \{0, \ldots, J^{[s]}-1\}$, $$\bar{g}_j^{[s]}(b) = \Sigma_k \bar{\mu}_{jk}^{[s]} \Sigma_i a_{ji}^{[s]} b_{ki}, \text{ and} \qquad \text{Eq. 15:}$$

$$\Delta g_j^{[s]}(b) = -\ln \Sigma_m q_{jm}^{[s]} \exp(-\Sigma_k \Delta\mu_{jkm}^{[s]} \Sigma_i a_{ji}^{[s]} b_{ki}) \qquad \text{Eq. 16:}$$

denote linear (LI) and non-linear (NL) functions of b, respectively, and can be used to form two aggregate vectors $\bar{g}(b)$ and $\Delta g(b)$ in the same way of forming $g(b)$.

Thus, in one implementation, $\mu$ may be the non-linear component in the data model. Further, equation 14 includes two elements, with $\bar{g}(b)$ being linear and $\Delta g(b)$ being non-linear. In one implementation, the non-linear term $\Delta g(b)$ may be represented by equation 16. In particular, $\bar{g}(b) = \mathcal{H} b$ and matrix $\mathcal{H}$ is given by:

$$\mathcal{H} = \begin{pmatrix} \mathcal{U}_1^{[1]} \mathcal{A}^{[1]} & \mathcal{U}_2^{[1]} \mathcal{A}^{[1]} & \ldots \\ \mathcal{U}_1^{[2]} \mathcal{A}^{[2]} & \mathcal{U}_2^{[2]} \mathcal{A}^{[2]} & \ldots \\ \vdots & \vdots & \ddots \end{pmatrix}, \qquad \text{Eq. 17:}$$

where matrix $\mathcal{A}^{[s]}$, of size $J^{[s]} \times I$ and with element $a_{ji}^{[s]}$, denotes the discrete X-ray transform for all measurements made with spectrum s, and $U_k^{[s]}$ a diagonal matrix of size $J^{[s]}$ with diagonal elements $\bar{\mu}_{jk}^{[s]}$.

The DD-data model in equation 8 for an individual ray can then be re-expressed in a matrix form for all of the rays considered as:

$$g(b) - \Delta g(b) = \mathcal{H} b. \qquad \text{Eq. 18:}$$

While equation 18 is only a different form of the DD-data model in equation 8, it reveals that it is non-linear term $\Delta g(b)$ that results in the non-convexity of the data divergence and thus of the optimization program. Thus, as shown above, equation 14 includes three terms: $g_j^{[s]}(b)$ which is the measurement, $\bar{g}(b)$, which is a linear of b, and $\Delta g(b)$ which is a non-linear function of b. Equation 18 is a rewrite of equation 14 into vector form. Further, from equations 14 and 18, $\bar{g}(b)$ becomes matrix $\mathcal{H} b$.

If one assumes that $\Delta g(b)$ is independent of b (though in actuality it is a non-linear term), the left hand side of equation 18 is a linear function of b. Because of that assumption, one can place this equation into equation 10 or 11. In that regard, one is faced with a convex problem since $\Delta g(b)$ is assumed to be constant (independent of b).

There are various ways for numerically lowering the non-convex data divergence. In one way, it is first assumed that non-linear term $\Delta g(b)$ is known and denoted by $\widetilde{\Delta g}$. Under this condition, the DD-data model in equation 18 becomes a linear equation, i.e., $g(b) - \widetilde{\Delta g} = \mathcal{H} b$, and data divergence $D(\mathcal{H} b, g_M - \widetilde{\Delta g})$ and the optimization program consequently becomes convex, which can then be solved by use of a host of well-established algorithms.

The projection-onto-convex-sets (POCS) procedure can be used to lower convex $D(\mathcal{H} b, g_M - \widetilde{\Delta g})$ with the updating step:

$$b_k^{(n+1)} = b_k^{(n)} + \gamma^{(n)} \mu_{jk}^{[s]} \frac{\left[g_{\mathcal{M}\,j}^{[s]} - \widetilde{\Delta g}_j^{[s]}\right] - a_j^{[s]} \sum_k \mu_{jk}^{[s]} b_k^{(n)}}{\sum_k (\mu_{jk}^{[s]})^2 a_j^{[s]} a_j^{[s]T}} a_j^{[s]T}, \qquad \text{Eq. 19:}$$

where $j \in \{0, \ldots, J^{[s]}-1\}$, $\widetilde{\Delta g}_j^{[s]}$ is the jth element with spectrums of $\widetilde{\Delta g}$, $a_j^{[s]}$ a row vector that is the jth row of matrix $\mathcal{A}^{[s]}$, and $a_j^{[s]T}$ a column vector as the transpose of $a_j^{[s]}$, and $0 < \gamma^{(n)} < 2$. Thus, $\Delta g$ may be transformed into $\widetilde{\Delta g}_j^{[s]}$, with the ~ representing the approximation. The transformation into $\widetilde{\Delta g}_j^{[s]}$ is one example of linearizing the non-linear model. In a specific implementation, $\widetilde{\Delta g}$ may be considered a constant.

Using $b^{(n)}$ in equation 16, one can calculate:

$$\Delta g_j^{[s]}(b^{(n)}) = -\ln \Sigma_m q_{jm}^{[s]} \exp(-\Sigma_k \Delta\mu_{jkm}^{[s]} a_j^{[s]} b_k^{(n)}). \qquad \text{Eq. 20:}$$

Thus, equation 20 is one representation of the actual difference between the approximation $\widetilde{\Delta g}^{[s]}$ and the true non-linear model. As discussed below, one can use equation 20 to replace $\widetilde{\Delta g}^{[s]}$. With this, the methodology may thus compensate for the transformation (e.g., compensate for the linearization) of the non-linear model. In this regard, the compensation may be in addition to the linearization. In one implementation, the compensation may be performed iteratively. Thus, it is then proposed to use $\Delta g_j^{[s]}(b^{(n)})$ as an estimate of $\widetilde{\Delta g}_j^{[s]}$ in equation 19, and thus obtain an NC-POCS update procedure as:

$$b_k^{(n+1)} = b_k^{(n)} + \gamma^{(n)} \mu_{jk}^{[s]} \frac{\left[g_{\mathcal{M}\,j}^{[s]} - \Delta g_j^{[s]}(b_k^{(n)})\right] - a_j^{[s]} \sum_k \mu_{jk}^{[s]} b_k^{(n)}}{\sum_k (\mu_{jk}^{[s]})^2 a_j^{[s]} a_j^{[s]T}} a_j^{[s]T}, \qquad \text{Eq. 21:}$$

which has a form identical to that of the conventional POCS, except for that at iteration n, $\Delta g_j^{[s]}(b^{(n)})$ is calculated to compensate for the non-linear effect. As shown in equation 21, the argument of $\Delta g_j$ is $b_k$. $b_k$ is the current reconstruction at this iteration. In this regard, at each iteration, there is knowledge of $b_k$. This knowledge of $b_k$ may be used to estimate $\Delta g_j$ through equation 20. Thus, in one implementation, the compensation may be iterative. Further, the iterations may result in convergence. In other words, an iterative procedure is used in which the compensation for the approximation of $\Delta g(b)$ is performed. FIG. 25 depicts pseudo code used to implement equation 21 and the non-convex-projection onto convex sets (NC-POCS) in accordance with an illustrative embodiment.

Using this, a projection-onto-convex-sets tailored to a non-convex application may be developed. In particular, combining this NC-POCS procedure for lowering $D(g(b), g_M)$ with the steepest descent (SD) for lowering the total variation (TV) objective function, one may obtain an heuristic ASD-NC-POCS algorithm for numerically solving the non-convex program specified by equations 9-11. Similar to the conventional ASD-POCS algorithm, the ASD-NC-POCS algorithm adaptively lowers the image TV and data divergence by use of the SD and NC-POCS procedures for image reconstruction in MSXT, with the pseudo-code as illustrated in FIG. 25. In a reconstruction, once the practical convergence condition on the data constraint is satisfied, gradient descent steps are applied to further lower data divergence so that other practical convergence conditions can be met rapidly. The ASD-NC-POCS methodology may further be used with one or more convergence conditions.

One or more types of reconstruction parameters may be used in the optimization-based image reconstruction. In one implementation, there are two types of parameters involved in an optimization-based image reconstruction, which are referred to as program and algorithm parameters. Program parameters may specify the optimization program in equation 9, including image voxel, spectra $q_j^{[s]}$, system matrices $\mathcal{A}^{[s]}$, and parameter $\varepsilon$. Different choices of program parameters may lead to different optimization programs and thus different designed solutions. In one implementation, parameter E may be the focus that impacts dominantly the reconstruction, while selecting image voxel, $q_j^{[s]}$, and $\mathcal{A}^{[s]}$ similar to those used in practical applications. The algorithm parameters such as $\gamma^{(n)}$, $N_{TV}$, and $\alpha_k(n)$ in the algorithm illustrated in FIG. 25 may control the algorithm path leading to the designed solution. While the algorithm parameters have no effect on the designed solutions, they can impact the numerical reconstructions especially for a non-convex program. Thus, in one implementation, the same algorithm parameters may be used as those used in the conventional ASD-POCS algorithm.

Three mathematical convergence conditions may be considered for the ASD-NC-POCS algorithm:

$$D(b^{(n)}) = |D(g(b^{(n)}, g_{\mathcal{M}}) - \varepsilon|/\varepsilon \to 0,$$

$$\Delta\Psi(b^{(n)}) = \frac{|\Psi(b^{(n+1)}) - \Psi(b^{(n)})|}{|\Psi(b^{(n+1)}) + \Psi(b^{(n)})|} \to 0, \text{ and}$$

$$c_\alpha(b^{(n)}) = \hat{d}_{data}^T(b^{(n)})\hat{d}_{TV}(b^{(n)}) \to -1,$$

Eqs. 22:

as iteration number $n \to \infty$, where unit vectors $\hat{d}_{data}(b^{(n)})$ and $\hat{d}_{TV}(b^{(n)})$ are defined below. The second condition in Eqs. 22 is for the optimality of the objective function, whereas the other two are the local optimality conditions, i.e., the Karush-Kuhn-Tucker (KKT) conditions, as shown below. While the mathematical convergence conditions may not be met in practical reconstructions, they may be used to devise practical convergence conditions for studies discussed below.

With regard to numerical experiment design, one may consider scan configuration dimensions. Specifically, while the ASD-NC-POCS algorithm developed can reconstruct images from cone-beam data collected over general source trajectories, the ASD-NC-POCS algorithm may also be applied to other types of beams. In particular, ASD-NC-POCS algorithm may be applied to a fan-beam configuration, such as image reconstruction from data collected with a fan-beam configuration over a circular trajectory, with physical dimensions similar to those used in a standard cone-beam CT (CBCT) employed in radiation therapy. In one implementation, the CBCT system may have source-to-detector and source-to-center-of-rotation distances of 1500 mm and 1000 mm, respectively, and a linear detector of 400 mm in length, which form a field-of-view (FOV) of 265 mm in diameter. Imaged subjects are assumed to be completely within the FOV. In alternative embodiments, different dimensions may be used. As discussed above, the configuration shown in FIG. 1A is a standard, full-scan configuration in which each data set is collected for spectrum s at views uniformly distributed over $2\pi$, and which is used for verification and benchmark of the algorithm implementation and performance. In addition, other non-standard configurations, such as illustrated in FIGS. 2-8, may be utilized to demonstrate the application of the methodology.

With regard to spectra, the ASD-NC-POCS algorithm may be applicable to MSXT with multiple ($S \geq 2$) spectral measurements. Discussed herein are applications using only two (i.e., S=2) spectral data sets collected with two, i.e., the low (s=1) and high (s=2) spectra at 80 and 140 kVp. Different specta values may be used in alternative implementations. The incident spectra are generated using the TASMICS worksheet (v1.0), assuming a tungsten anode and 5-mm-Al filter, to simulate spectrum from a X-ray CT tube. The detector-energy response is modeled to be a linear energy-integrating response. The discrete X-ray spectrum, taken as the product of the incident spectrum and detector-energy response with $\Delta_E=1$ (KeV), is normalized and shown in FIG. 1B. As discussed, the ASD-NC-POCS algorithm may also be applied to spectral measurements greater than 2.

With regard to basis images, two (i.e., K=2) basis images are considered, and are referred to as the water and bone images in the reconstruction. It is further assumed that the spectra are the same for all rays within one kVp scan, i.e., the discretized spectrum can be denoted by $q_m^{[s]}$, without the dependence on ray j.

With regard to monochromatic images, using basis images $b_k$ reconstructed, along with knowledge of mass-attenuation coefficients, one can readily obtain monochromatic image $f_m$, by using equation 7. In general, due to the presence of decomposition error, monochromatic image $f_m$, may represent only approximately linear attenuation coefficient image $f_m'$.

Figure 10A:
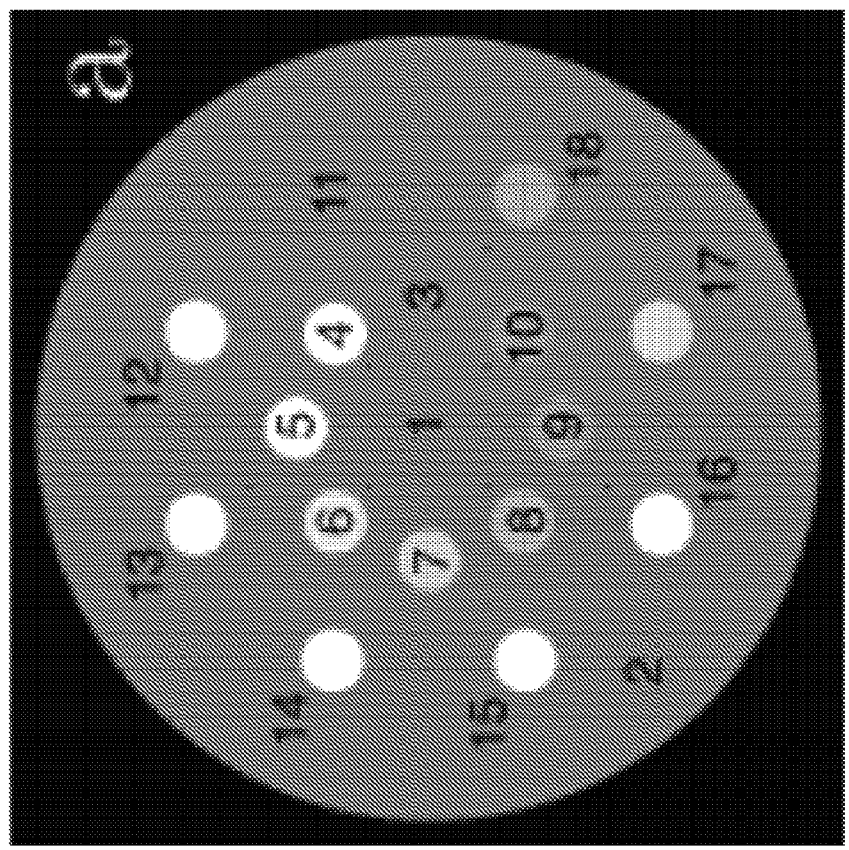
FIG. 10A depicts a DE-472 phantom with 18 regions of interest within 16 circular inserts and 2 background areas highlighted by 1 to 18 in accordance with an illustrative embodiment.
Figure 10B:
FIG. 10B is a lung phantom in accordance with an illustrative embodiment.
Figure 10C:
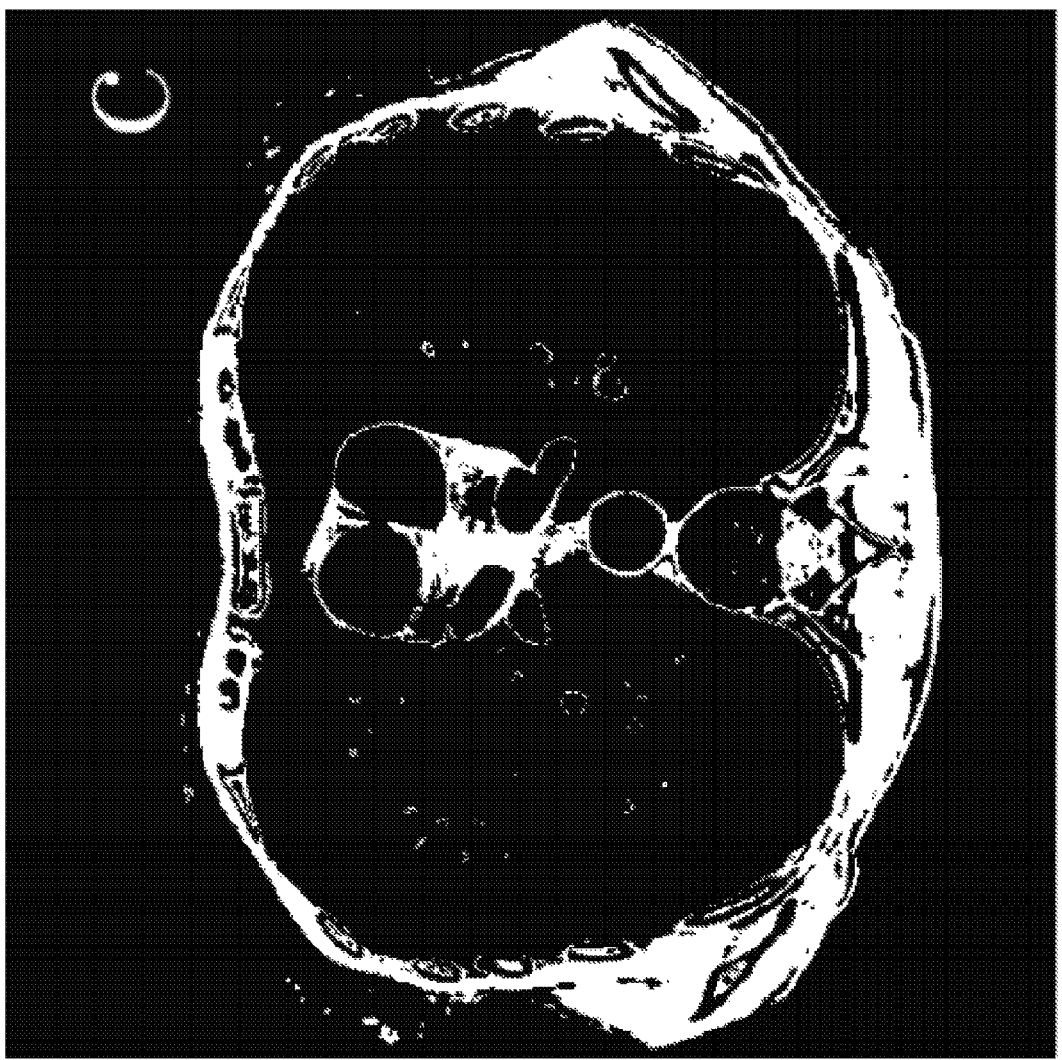
FIG. 10C is a lung phantom with a muscle region of interest in accordance with an illustrative embodiment.
Figure 10D:
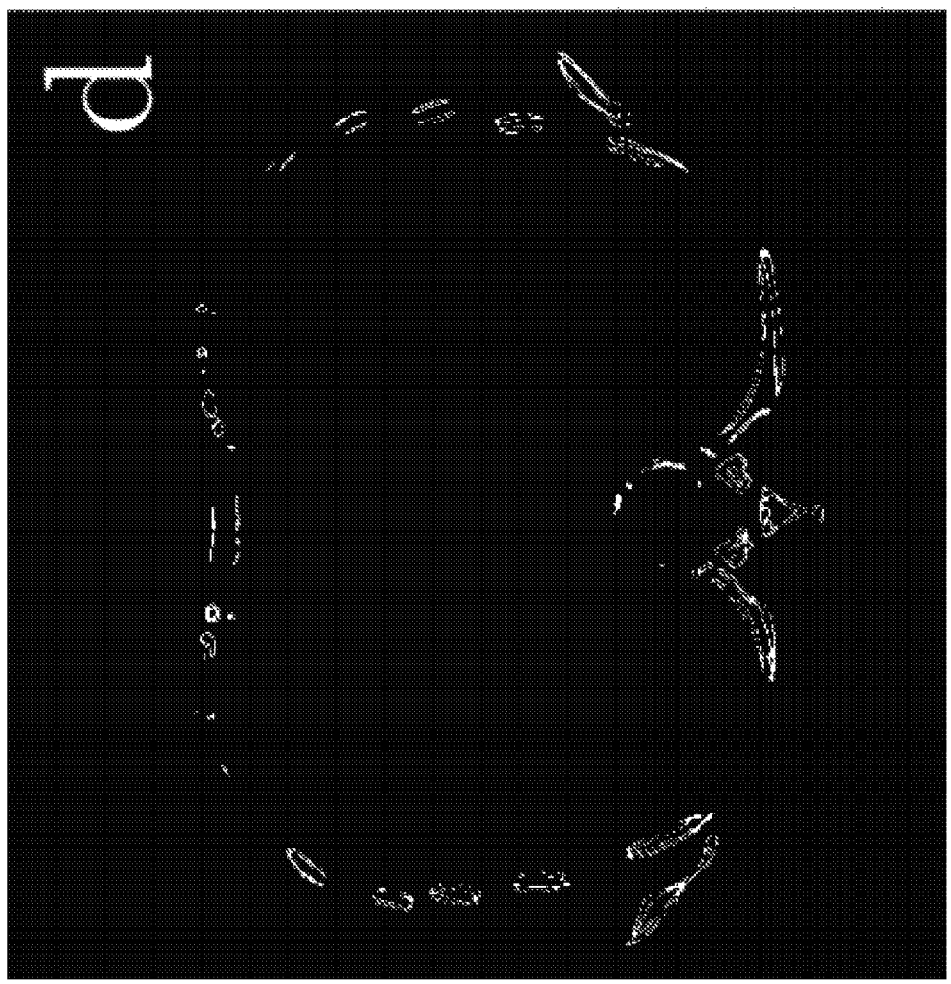
FIG. 10D is a lung phantom with a bone region of interest in accordance with an illustrative embodiment.
Figure 10E:
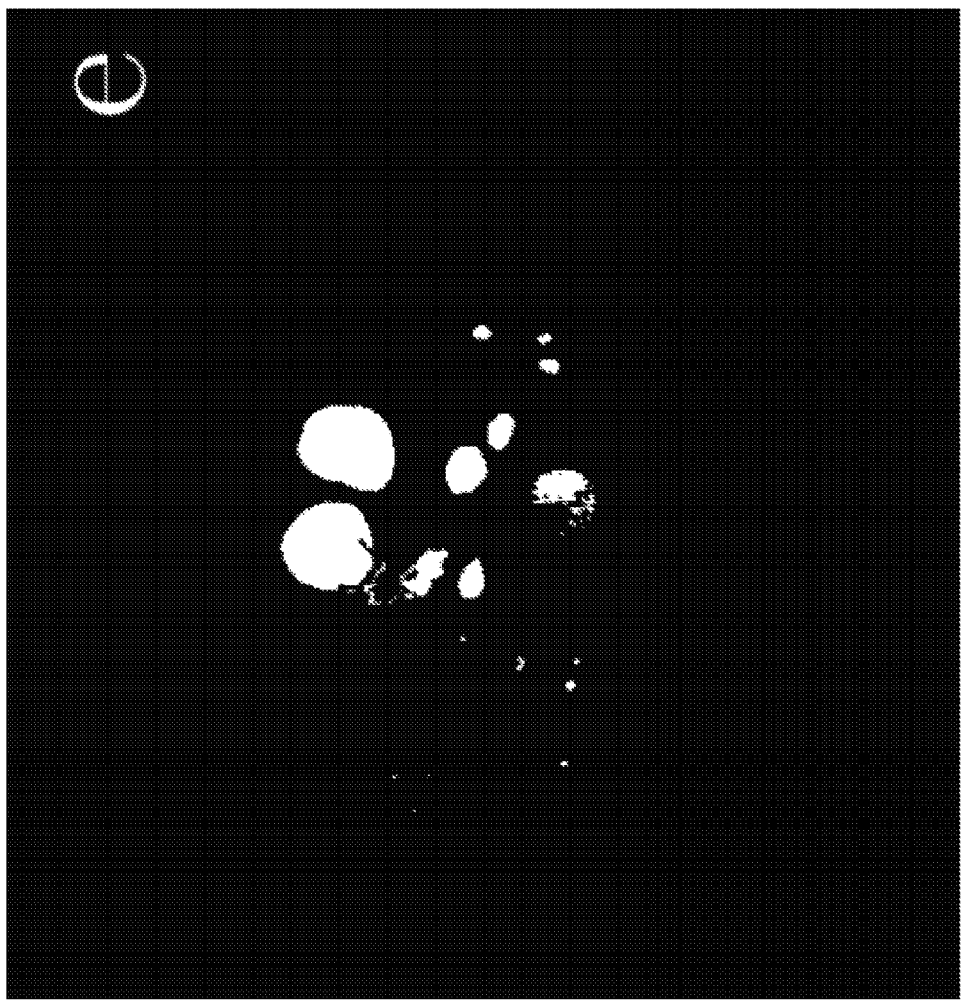
FIG. 10E is a lung phantom with a water region of interest in accordance with an illustrative embodiment.

Illustrated in FIGS. 10A-E are two digital phantoms. The first simulates the standardized dual-energy contrast phantom with iodine and calcium solution inserts, referred to as the DE-472 phantom, and the second mimics human thoracic anatomy, referred to as the lung phantom. Both phantoms are represented on a 512×512 array of square pixels of 0.49 mm. Specifically, FIG. 10A depicts a DE-472 phantom with 18 regions of interest within 16 circular inserts and 2 background areas highlighted by 1 to 18 in accordance with an illustrative embodiment. FIG. 10B is a lung phantom in accordance with an illustrative embodiment. FIG. 10C is a lung phantom with a muscle region of interest in accordance with an illustrative embodiment. FIG. 10D is a lung phantom with a bone region of interest in accordance with an illustrative embodiment. FIG. 10E is a lung phantom with a water region of interest in accordance with an illustrative embodiment.

Figure 18:
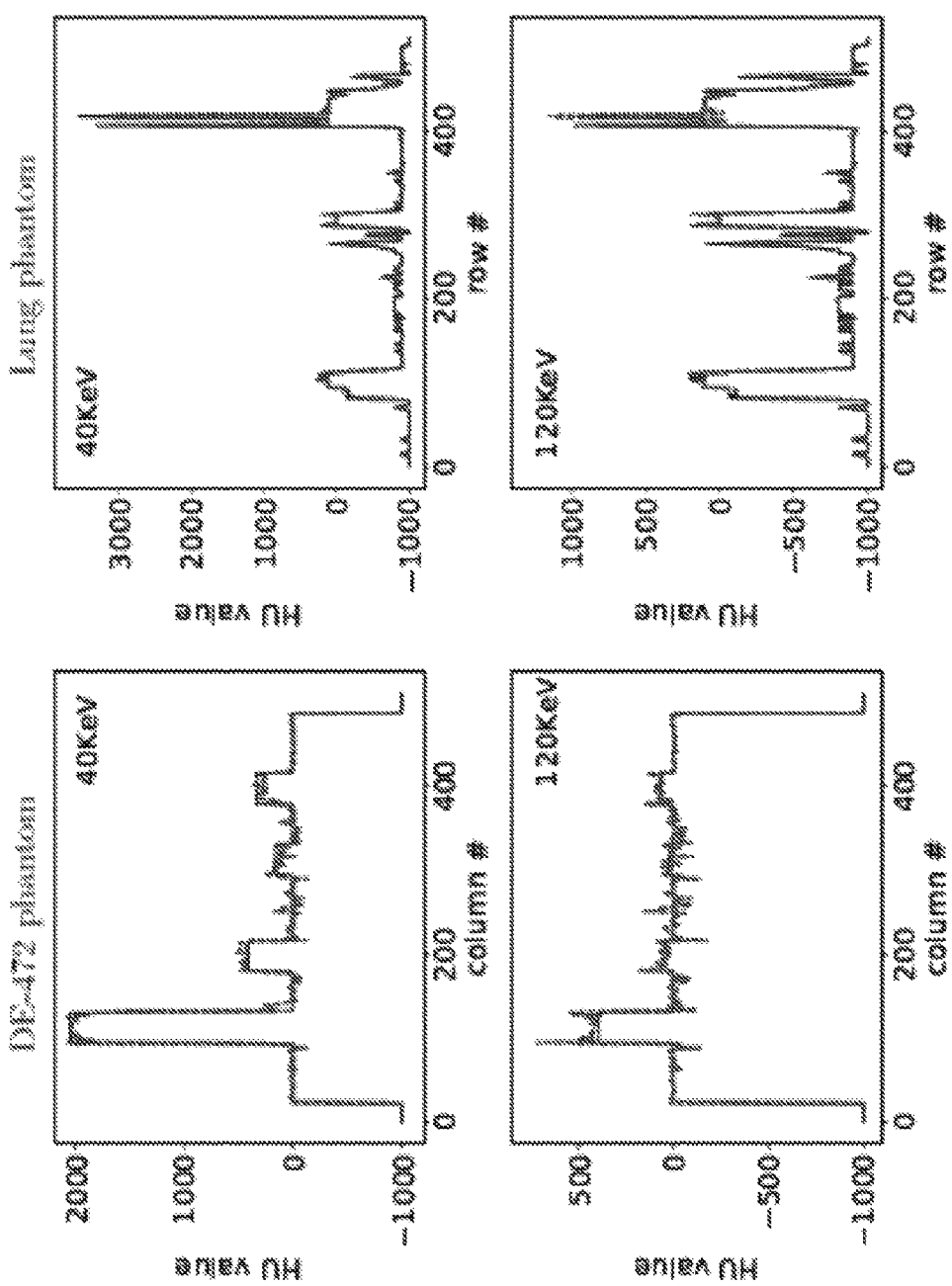
FIG. 18 illustrates profiles of the reconstructed (dashed) and truth (solid) monochromatic images at 40 and 120 KeV along the horizontal and vertical lines indicated in row 2 of FIG. 14 in accordance with an illustrative embodiment.

FIG. 9 is a table summarizing the materials used in the composition of the phantoms of FIG. 10 in accordance with an illustrative embodiment. Not depicted in FIG. 9 is water, which has 1.0 g/ml density. For the lung phantom simulating various human tissues, the ICRU-44 standard was used for its materials, and the mass-attenuation coefficients are readily available as tabulated data. For the DE-472 phantom, the mass-attenuation coefficients of the iodine and calcium solutions are calculated using the XCOM web program, according to the specifications of the physical GAMMEX 472 Dual Energy CT phantom. As shown in FIG. 10A, 18 regions of interest (ROIs) in the DE-472 phantom, defined based on the inserts, and 3 ROIs of the lung phantom, defined based on material masks, are shown for computing metrics for parameter determination in the studies below.

Further, a verification study was performed to verify that under imaging conditions of interest, the ASD-NC-POCS algorithm can numerically solve the non-convex optimization program in equation 9 from ideal data generated by use of the DD-data model in equation 8 without decomposition error and noise.

With regard to the experimental parameters, two truth basis images representing water and cortical bone were used in equation 8 to generate ideal data from the lung phantom by use of the full-scan configuration with the low and high kVp spectra described in FIG. 1A. For computation efficiency, an image array of I=128×128 1.95-mm square pixels is considered, and a linear detector of 256 1.56-mm bins is used to generate projections at 160 views evenly distributed over $2\pi$ for each of the low and high kVp spectra. As such, the X-ray transform matrices $\mathcal{A}^{[1]}=\mathcal{A}^{[2]}$ are of size $J^{[1]}=J^{[2]}=256\times160$ and I=128×128. With parameters, spectra, and $\mathcal{A}^{[s]}$ determined above, parameter $\varepsilon=10^{-8}$ is selected to form a tight solution set, as the study may use ideal data.

Based upon the mathematical convergence conditions in equations 22, practical convergence conditions for the verification study are designed as:

$$\overline{D}(b^{(n)}) < 10^{-4},$$

$$\overline{\Delta\Psi}(b^{(n)})) < 10^{-4}, \text{ and}$$

$$c_\alpha(b^{(n)}) < -0.99. \quad \text{Eqs. 23:}$$

Convergent reconstruction is obtained when all of the convergence conditions above are satisfied. Because the truth basis images are known, a reconstruction-error metric $\overline{\Delta}_b(b^{(n)}) = \|b^{(n)} - b_{true}\|_2 / \|b_{true}\|_2$ may also be devised, e.g., the normalized $l_2$-distance between the truth and reconstructed basis images. This metric provides a quantitative indication as to whether and how the reconstructed basis images approach their truth counterparts.

Figure 11:
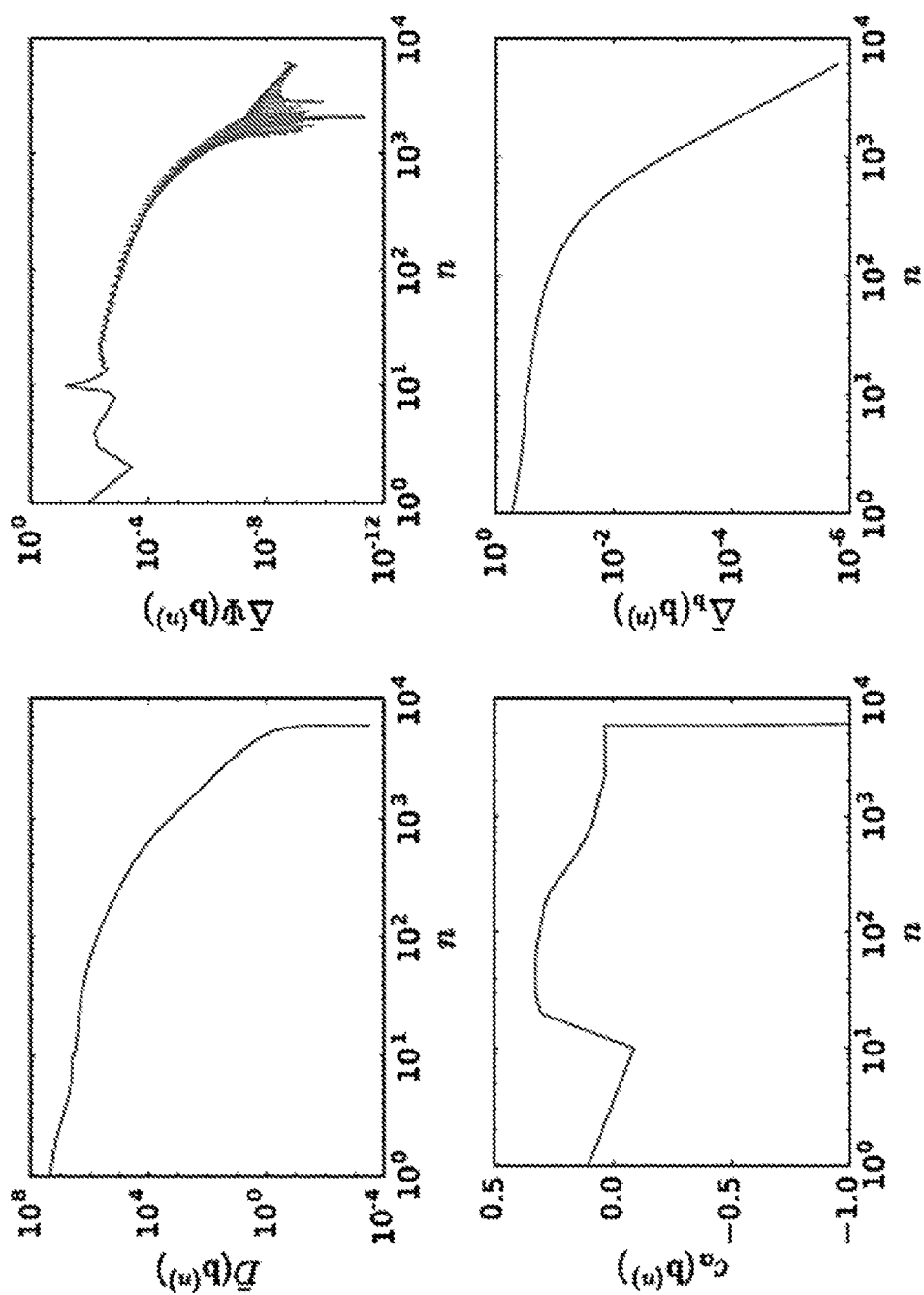
FIG. 11 illustrates convergence metrics $\overline{D}(b^{(n)})$, $\overline{\Delta\Psi}(b^{(n)})$, and $c_\alpha(b^{(n)})$, and reconstruction-error $\overline{\Delta}_b(b^{(n)})$ as functions of iterations n in accordance with an illustrative embodiment.
Figure 12:
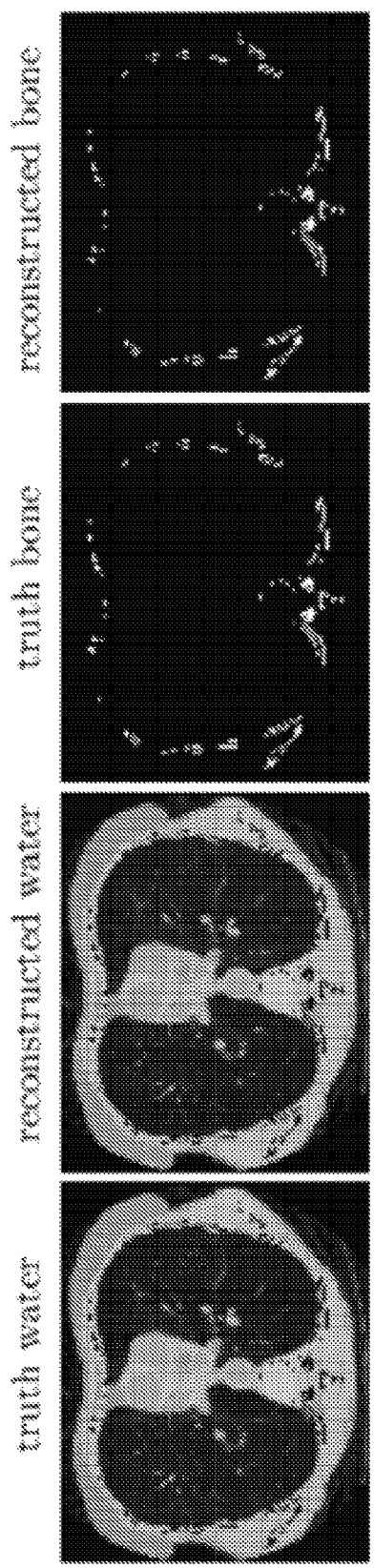
FIG. 12 illustrates truth and reconstructed water- and bone-basis images in accordance with an illustrative embodiment.

FIG. 11 depicts ideal data and display convergence results in accordance with an illustrative embodiment. FIG. 12 depicts convergent reconstructions in accordance with an illustrative embodiment. More specifically, FIG. 11 illustrates convergence metrics $\overline{D}(b^{(n)})$, $\overline{\Delta\Psi}(b^{(n)})$, and $c_\alpha(b^{(n)})$, and reconstruction-error $\overline{\Delta}_b(b^{(n)}))$ as functions of iterations n, and FIG. 12 illustrates truth and reconstructed water- and bone-basis images. With regard to study results, the ASD-NC-POCS algorithm may be applied to reconstructing basis images from the ideal data and display convergence results in FIG. 11 and convergent reconstructions in FIG. 12. It can be observed that the practical convergence conditions in equations 23 are satisfied and that convergent reconstructions are visually identical to their truth counterparts. In particular, the reconstruction-error metric in FIG. 11 reveals quantitatively a small difference of the convergent reconstructions than their truth basis images, thus providing a numerical verification of the ASD-NC-POCS algorithm and its computer implementation.

Following the verification study with ideal data above, a characterization study may be performed on the ASD-NC-POCS algorithm by using data that contain decomposition error and statistical noise, which are inconsistent with the DD-data model in equation 8.

For each phantom illustrated in FIGS. 10A-E, using its truth monochromatic image $f_m'$ and spectra in FIG. 1B, equation 5 is used to generate low- and high-kVp data at 640 overlapping views evenly distributed over $2\pi$, which thus contain decomposition error. Furthermore, Poisson noise is added to data by scaling the spectra to yield $2\times10^4$ photons per ray in the air scan. The image array of the same dimension and pixel size as the digital phantom is used in the reconstruction. At each view, projection samples are collected with a 400-mm linear detector that includes 1024 bins of 0.39-mm size. Alternatively, a different number of bins and/or size may be used. Therefore, the X-ray transform matrices $\mathcal{A}^{[1]}$ and $\mathcal{A}^{[2]}$ are identical and of dimensions $J^{[1]}=J^{[2]}=640\times1024$ and I=512×512. With the determination of program parameters, i.e., image pixel, spectra, and matrices $\mathcal{A}^{[s]}$, the strategy for the selection of parameter E in the characterization experiment is discussed below.

Because data are generated directly from linear attenuation coefficient $f_m'$, there may be no truth basis images in the characterization study. Instead, metrics can be designed based upon monochromatic images $f_m$ for determination of parameter $\varepsilon$. R regions of interest (ROIs) in a monochromatic image may be chosen for calculating the "biases" and "standard deviations" within the ROIs as:

$$\theta_{rm} = \sum_i |f_{im} - f_{im}'|/I_r \text{ and } \sigma_{rm} = \left(\sum_i |f_{im} - \theta_{rm}|^2/(I_r - 1)\right)^{\frac{1}{2}},$$

where $i \in I_r$, and $I_r$ indicates the number of pixels within ROI r. Using $\theta_{rm}$ and $\sigma_{rm}^2$ computed at energies $m_1$ and $m_2$, two metrics are formed for determination of parameter $\varepsilon$:

$$\Theta = \sum_r [\theta_{rm_1}^2 + \theta_{rm_2}^2]^{\frac{1}{2}}/R \text{ and } \Sigma = \sum_r [\sigma_{rm_1}^2 + \sigma_{rm_2}^2]^{\frac{1}{2}}/R.$$

For a given configuration and phantom, monochromatic images $f_m$ are formed at $m_1=80$ KeV and $m_2=140$ KeV from basis images reconstructed for a number of $\varepsilon$ values, $\Theta$ and $\Sigma$ is computed from the images, and E is selected that yields lowest $\Theta$ and $\Sigma$.

Practical convergence conditions for the characterization study may be designed as:

$$\overline{D}(b^{(n)}) < 10^{-3},$$

$$\overline{\Delta\Psi}(b^{(n)}) < 10^{-3}, \text{ and}$$

$$c_\alpha(b^{(n)}) < -0.5, \quad \text{Eqs. 24:}$$

which may be looser than those in the verification study as the decomposition error and data noise are considered. The conventional ASD-POCS algorithm indicates that the third condition can often be relaxed to −0.5, instead of −0.99, with only imperceptible changes to the images. Using reconstructed basis image $b_k^{(n)}$ in equation 7, one can readily obtain monochromatic image $f_m^{(n)}$ at iteration n. Also, in the simulation study, truth monochromatic image $f_m'$ may be known, thus leading to the calculation of the reconstruction-error metric $\overline{\Delta f}(f_m^{(n)}) = \|f_m^{(n)} - f_m'\|_2/\|f_m'\|_2$, which may be the normalized $l_2$-distance between the truth and reconstructed monochromatic images at energy m.

Figure 13:
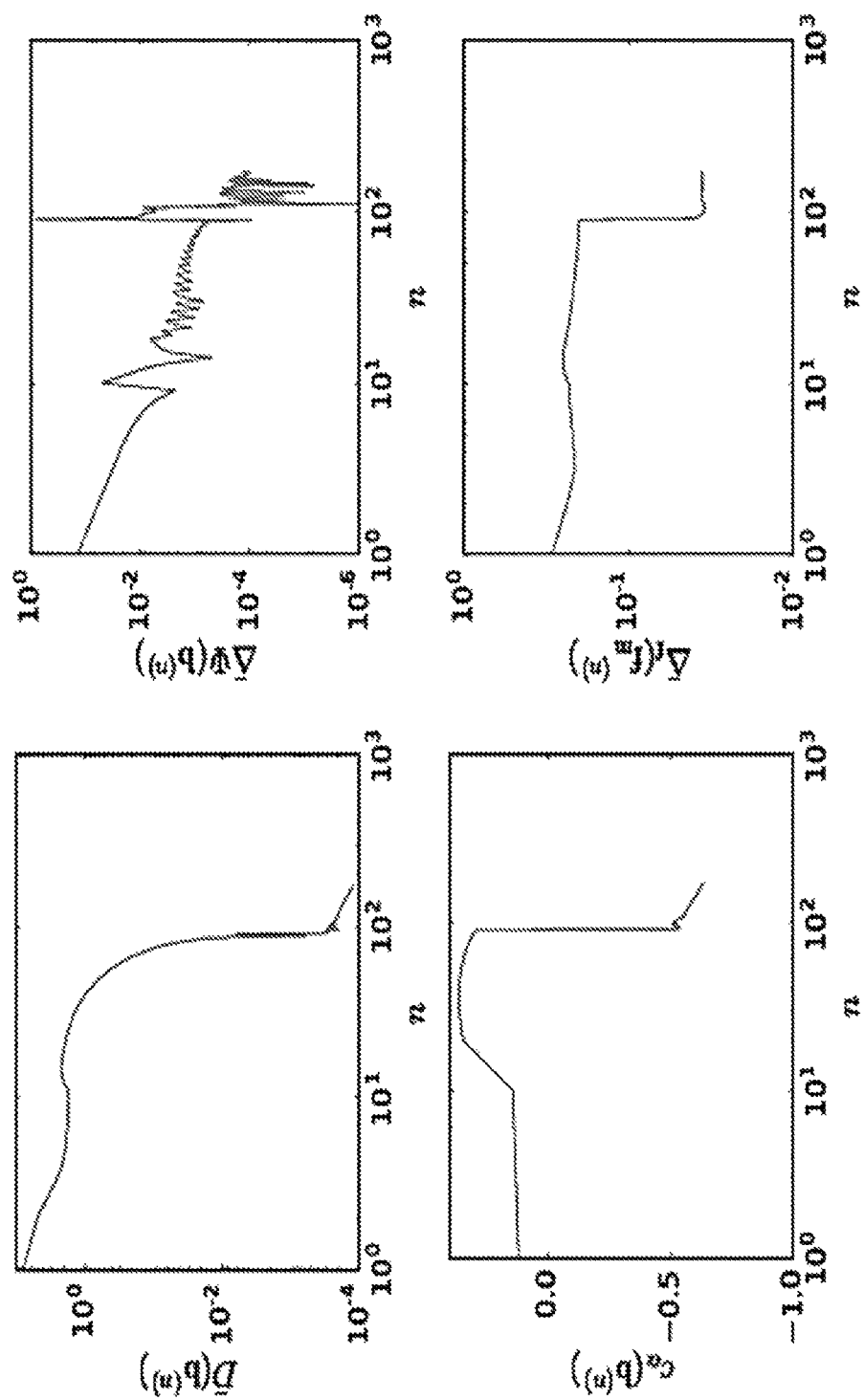
FIG. 13 illustrates convergence metrics $\overline{D}(b^{(n)})$, $\overline{\Delta\Psi}(b^{(n)})$, and $c_\alpha(b^{(n)})$, and reconstruction-error $\overline{\Delta}_f(f_m^{(n)})$ of an 80-KeV monochromatic image obtained with E=0.0170, as functions of iteration number n in accordance with an illustrative embodiment.

One focus of the study results is a demonstration of reconstruction convergence. In particular, a reconstruction is used from data of the full-scan configuration to demonstrate that the practical convergence conditions in equations 24 may be met by the ASD-NC-POCS algorithm. Without loss of generality, the reconstruction may be carried out with $\varepsilon=0.0170$. FIG. 13 illustrates convergence metrics $\overline{D}(b^{(n)})$, $\overline{\Delta\Psi}(b^{(n)})$, and $c_\alpha(b^{(n)})$ as functions of iteration number n in accordance with an illustrative embodiment. More specifically, FIG. 13 illustrates convergence metrics $\overline{D}(b^{(n)})$, $\overline{\Delta\Psi}(b^{(n)})$, and $c_\alpha(b^{(n)})$, and reconstruction-error $\Delta_f(f_m^{(n)})$ of an 80-KeV monochromatic image obtained with $\varepsilon=0.0170$, as functions of iteration number n. It can be observed that the ASD-NC-POCS algorithm converges to meet the practical convergence conditions.

With regard to the selection of the parameter $\varepsilon$, for each of DE-472 and lung phantoms, reconstructions are performed from its data by using the ASD-NC-POCS algorithm for multiple values of $\varepsilon$, metrics $\Theta$ and $\Sigma$ are calculated from the ROIs described with regard to FIGS. 10A-E in monochromatic energy reconstructions at 80 and 120 KeV. The value of $\varepsilon$ may be selected that yields the lowest $\Theta$ and $\Sigma$. Using the strategy, it has been determined that $\varepsilon=0.0170$ and $\varepsilon=0.0111$ in the characterization study using the DE-472 and lung phantoms, respectively.

Figure 14:
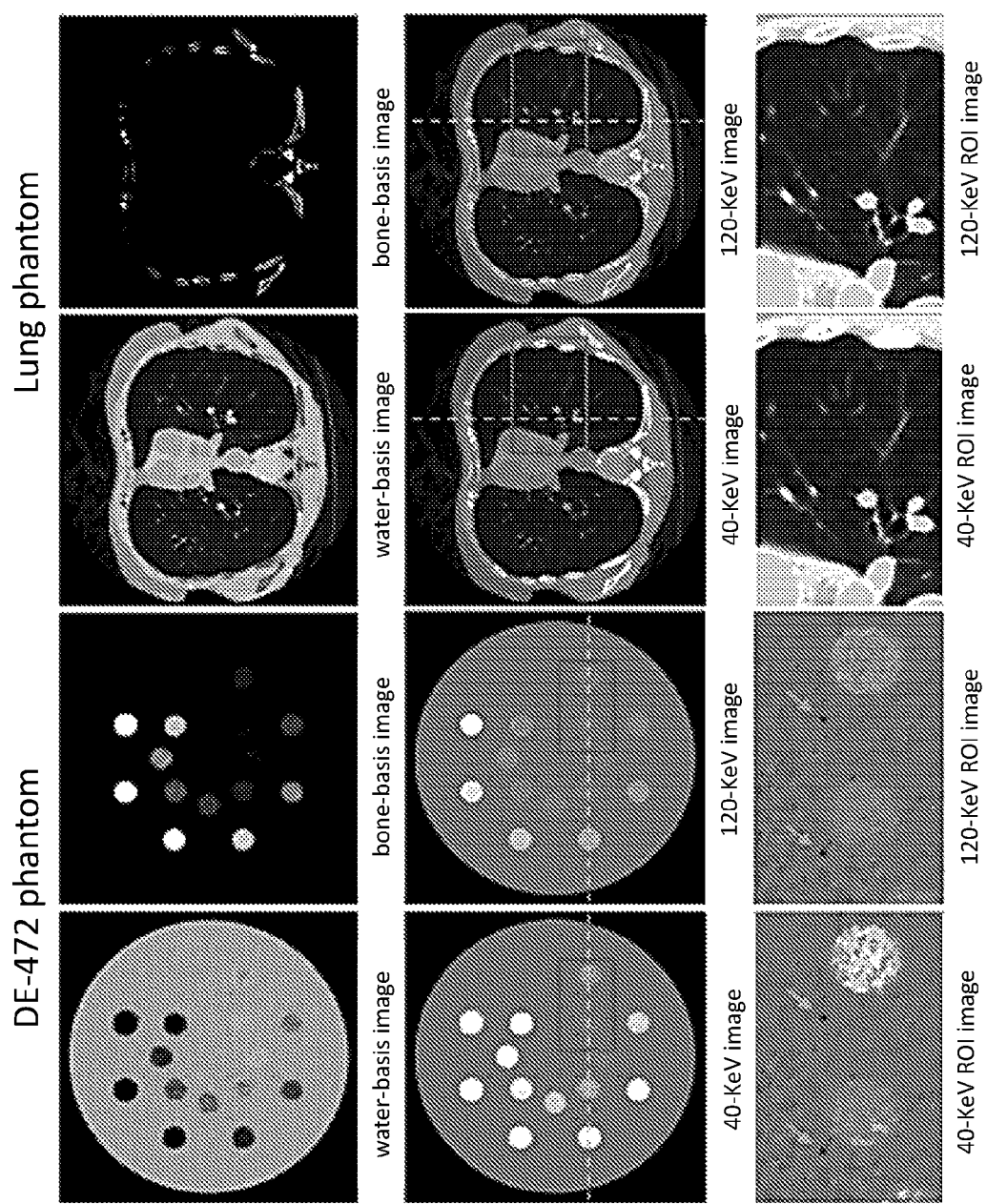
FIG. 14 illustrates water- and bone-basis images in accordance with an illustrative embodiment.

With regard to reconstruction results, using the program parameters (e.g., image pixel, spectra, matrices $\mathcal{A}^{[s]}$, and $\varepsilon$) determined, basis and monochromatic images of the DE-472 and lung phantoms may be reconstructed. FIG. 14 depicts water-basis and bone-basis images (row 1), 40- and 120-KeV monochromatic images (row 2), and zoomed-in views of ROI images (row 3) enclosed by boxes in row 2 from full-scan data of the DE-472 and lung phantoms, respectively. FIG. 14 includes display windows [0, 1.5] (row 1), [−1000, 1000] HU (row 2), and [−500, 500] HU (row 3, DE-472 phantom) and [−1000, 200] HU (row 3, lung phantom). The dashed lines indicate the location of the profile plots in FIG. 15, while the arrows point to the air bubbles in the DE-472 phantom. In FIG. 14, reconstructed basis images, monochromatic images are displayed at 40 and 120 KeV, which is used often for contrast enhancement and artifact reduction, and their zoomed-in views of ROI images are enclosed by the rectangular boxes indicated in row 2.

The water-basis image retains mostly the water and soft-tissue background, while high contrast inserts and bony structures appear largely in the bone-basis image. The seemingly observable "artifacts" in basis images reconstructed are understandable because data may contain decomposition error as they were generated from $f_m$ instead of two basis images. However, no significant cupping or band artifacts are visible in the monochromatic images, especially for the DE-472 phantom that contains high concentration iodine and calcium inserts. ROIs of the DE-472 phantom with a narrow display window show air-bubble contrast (indicated by the arrows) and discernible contrast inserts with the lowest concentration of iodine and calcium in the phantom. Meanwhile, ROIs of the lung phantom show details of the lung nodules in the dark background, with a display window to highlight these features.

Figure 15:
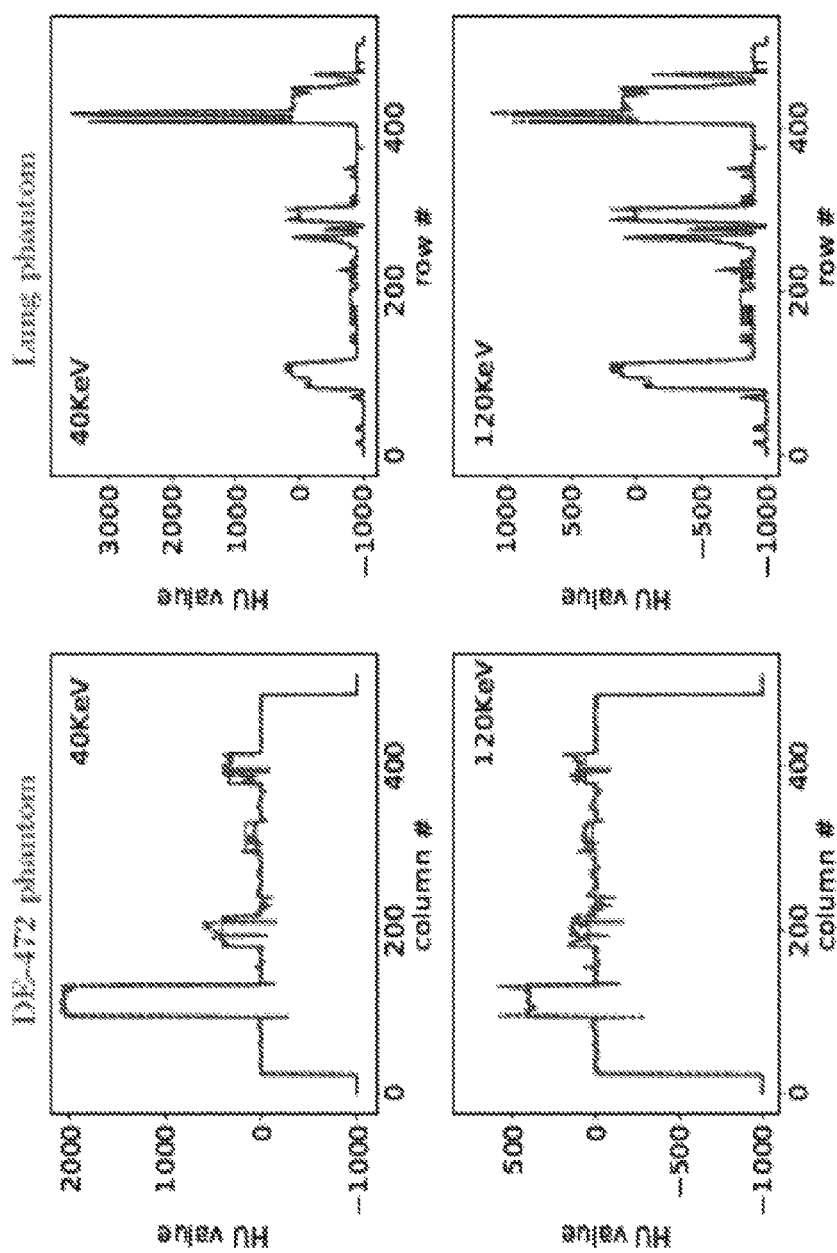
FIG. 15 depicts plots profiles of truth and reconstructed monochromatic images along the horizontal and vertical lines indicated in row 2 of FIG. 14 in accordance with an illustrative embodiment.

For acquiring a quantitative impression of the reconstructions, FIG. 15 depicts plots profiles of truth and reconstructed monochromatic images along the horizontal and vertical lines indicated in row 2 of FIG. 14 in accordance with an illustrative embodiment. Overall, reasonable quantitative agreement in monochromatic images is observed for the lung phantom, while some discrepancy can be observed between the DE-472 phantom and its monochromatic images due to the decomposition error. The profiles also reveal that the 40-KeV monochromatic images are of contrast higher than that of the 120-KeV counterparts.

Figure 16:
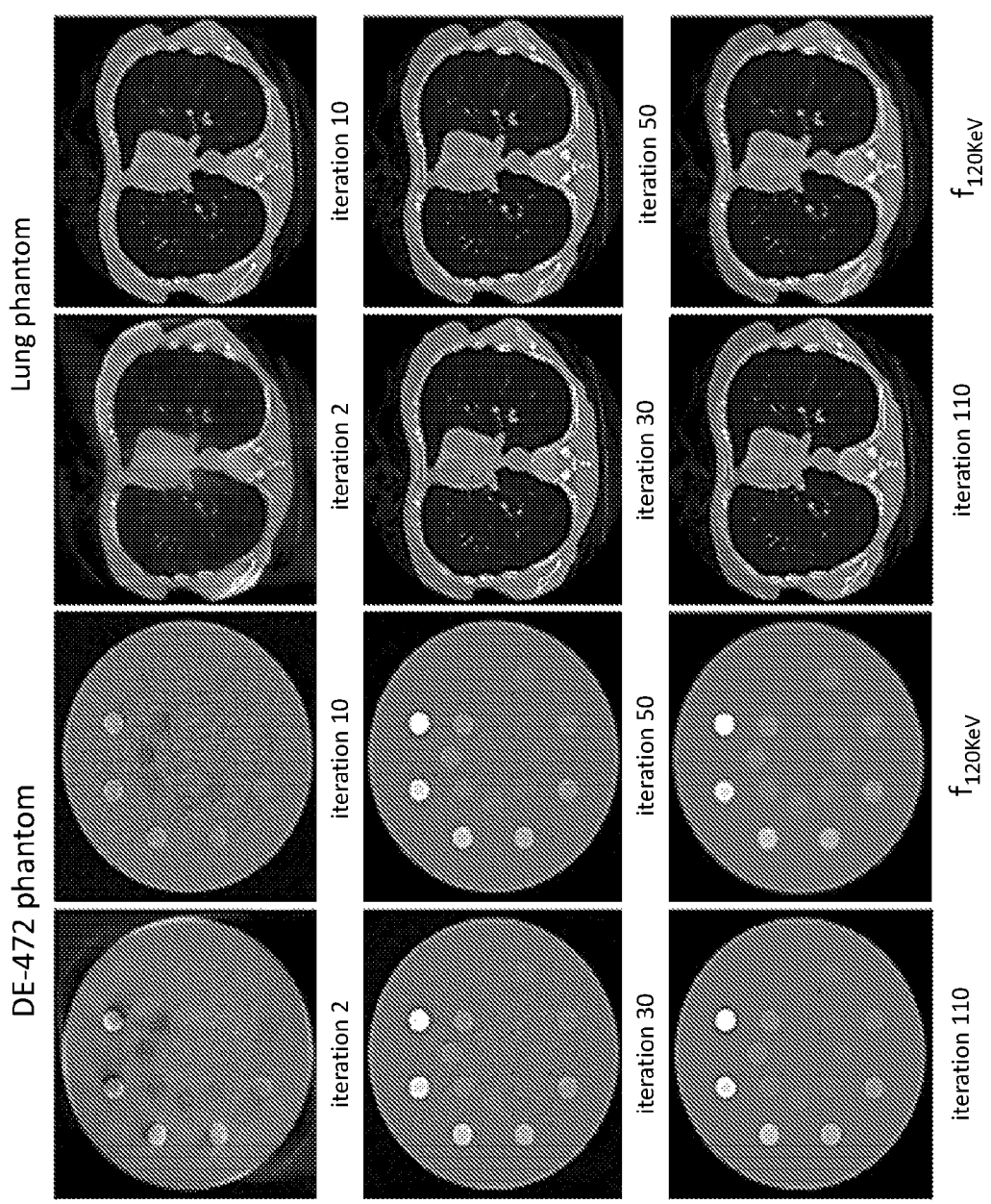
FIG. 16 illustrates reconstructions of 120-KeV monochromatic image at intermediate iterations for both phantoms in accordance with an illustrative embodiment.

It is of practical interest to inspect and understand how the reconstruction of monochromatic image evolves as iterations increase. Without loss of generality, FIG. 16 illustrates reconstructions of 120-KeV monochromatic image at intermediate iterations for both phantoms in accordance with an illustrative embodiment. It appears that reconstructions at as early as iteration 50 can resemble the respective convergent reconstructions. Similar observations can also be made for monochromatic energy images reconstructed at other energies.

Discussed below are investigations of image reconstruction for non-standard configurations of potential application significance enabled by the ASD-NC-POCS algorithm. For each of the non-standard configurations considered, a verification study was performed. However, the verification results are not shown because the results and conclusions are similar to those described above. Instead, characterization studies similar to that described above are the focus in which data may contain decomposition error and statistical noise. For each of the configurations and spectra in FIG. 1B, data is generated from each of the DE-472 and lung phantoms by using equation 5, and Poisson noise is added to the data by considering a total count level identical to that in the full-scan study discussed above. Furthermore, image pixel size and spectra used may also be identical to those in the study discussed above, while matrices $\mathcal{A}^{[s]}$ are illustrated in, and parameter E is determined by, use of the strategy described above for each of the non-standard configurations.

As discussed above, configurations may have varying angular coverages. For example, FIGS. 5-6 involve varying angular coverages. With regard to study parameters, in the sparse-view configuration in FIGS. 5-6, each of the low- and high-kVp data sets contains 320 views, thus forming a total of 640 projection views. Again, at each view, a linear detector comprising 1024 bins of 0.39-mm size is used for data collection. Therefore, matrices $\mathcal{A}^{[1]}$ and $\mathcal{A}^{[2]}$ are of identical dimensions $J^{[1]}=J^{[2]}=320\times1024$ and $I=512\times512$. Furthermore, using the strategy described above, $\varepsilon=0.0116$ and 0.008, respectively, is selected for the DE-472- and lung-phantom studies below.

In the limited-angular-range configuration in FIGS. 5-6, each of the two adjacent angular ranges covers 98°, thus forming a total of 196°-angular range (corresponding to a short-scan angular range) and low- or high-kVp data are generated at 174 views uniformly distributed over each of the two angular ranges, respectively, with a linear detector identical to that in the sparse-view configuration. Therefore, matrices $\mathcal{A}^{[1]}$ and $\mathcal{A}^{[2]}$ are of identical dimensions $J^{[1]}=J^{[2]}=174\times1024$ and $I=512\times512$. Again, using the strategy described above, $\varepsilon=0.0085$ and 0.0064, respectively, is selected for the DE-472- and lung-phantom studies below.

Figure 17:
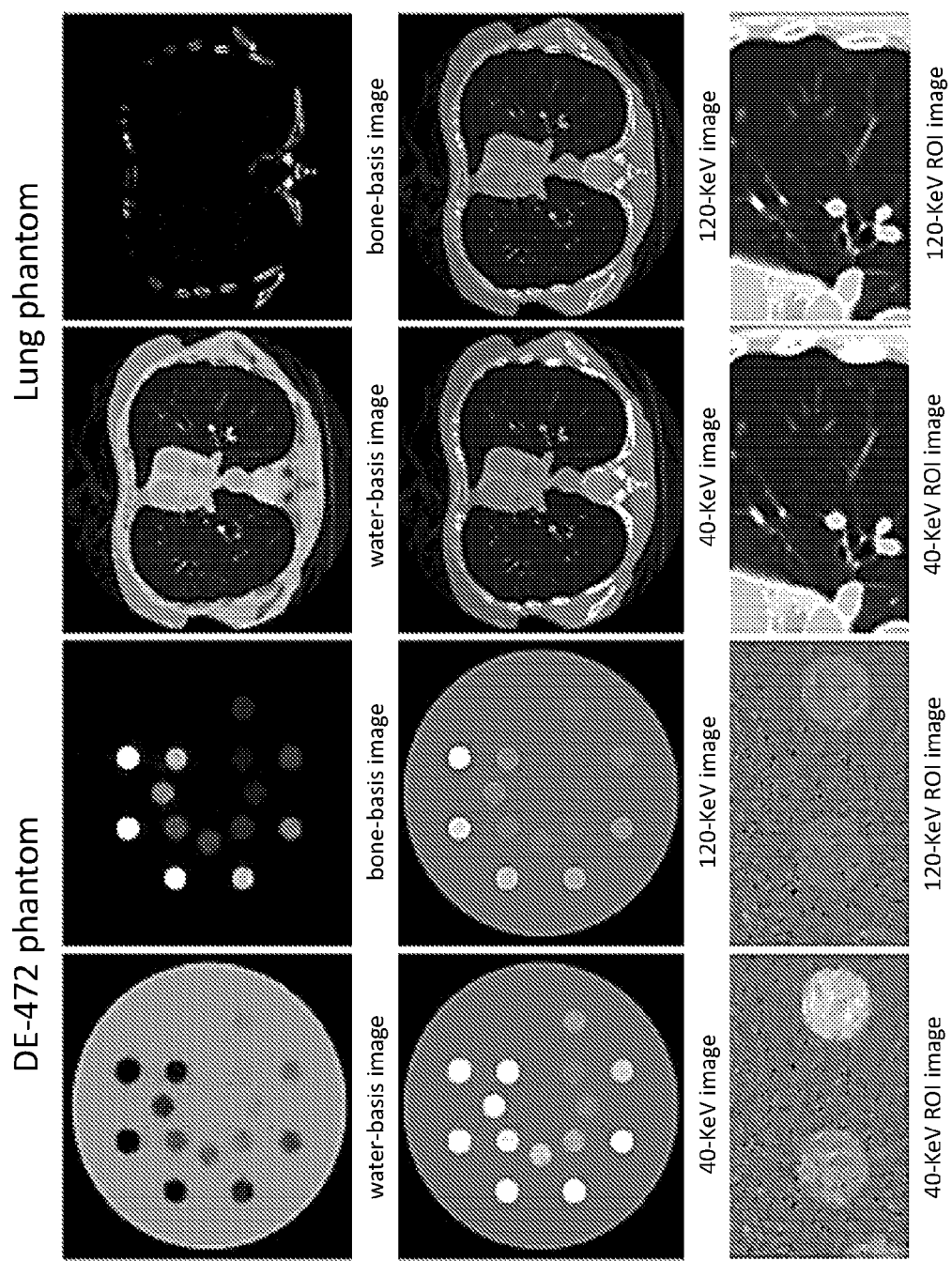
FIG. 17 illustrates reconstruction results for both phantoms from data acquired with the sparse-view configuration in accordance with an illustrative embodiment.

FIG. 17 illustrates reconstruction results for both phantoms from data acquired with the sparse-view configuration in accordance with an illustrative embodiment. Specifically, FIG. 17 illustrates water- and bone-basis images (row 1), 40- and 120-KeV monochromatic images (row 2), and zoomed-in views of ROI images (row 3) similar to those in row 3 of FIG. 14 from sparse-view-scan data of the DE-472 and lung phantoms, respectively, with display windows [0, 1.5] (row 1), [−1000, 1000] HU (row 2), and [−500, 500] HU (row 3, DE-472 phantom) and [−1000, 200] HU (row 3, lung phantom). Reconstructed monochromatic images at 40 and 120 KeV visually resemble their counterparts obtained from the full-scan data. Both basis images of each phantom show clear material separation, and the monochromatic images display an uniform background and no visible artifacts caused by non-linear spectral effect. In addition to reconstruction visualization, FIG. 18 illustrates profiles of the reconstructed and truth monochromatic images along the horizontal and vertical lines indicated in row 2 of FIG. 14 in accordance with an illustrative embodiment. It can be observed that for sparse-view-scan configuration, the agreement of monochromatic images reconstructed with the truth counterparts is comparable to that for the full-scan configuration in FIG. 15.

Figure 19:
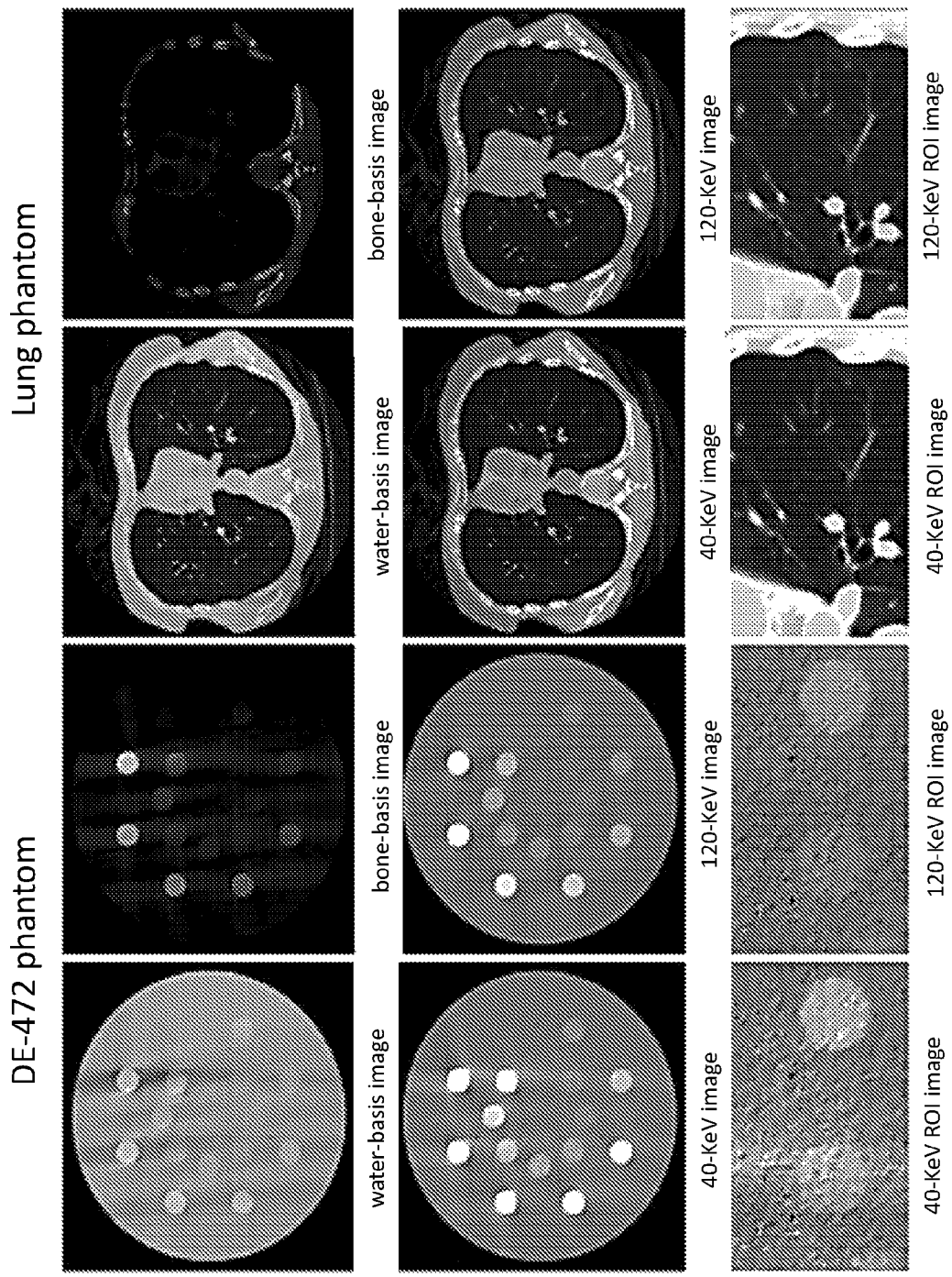
FIG. 19 illustrates reconstruction results for both phantoms from data acquired with the limited-angular-range configurations in accordance with an illustrative embodiment.
Figure 20:
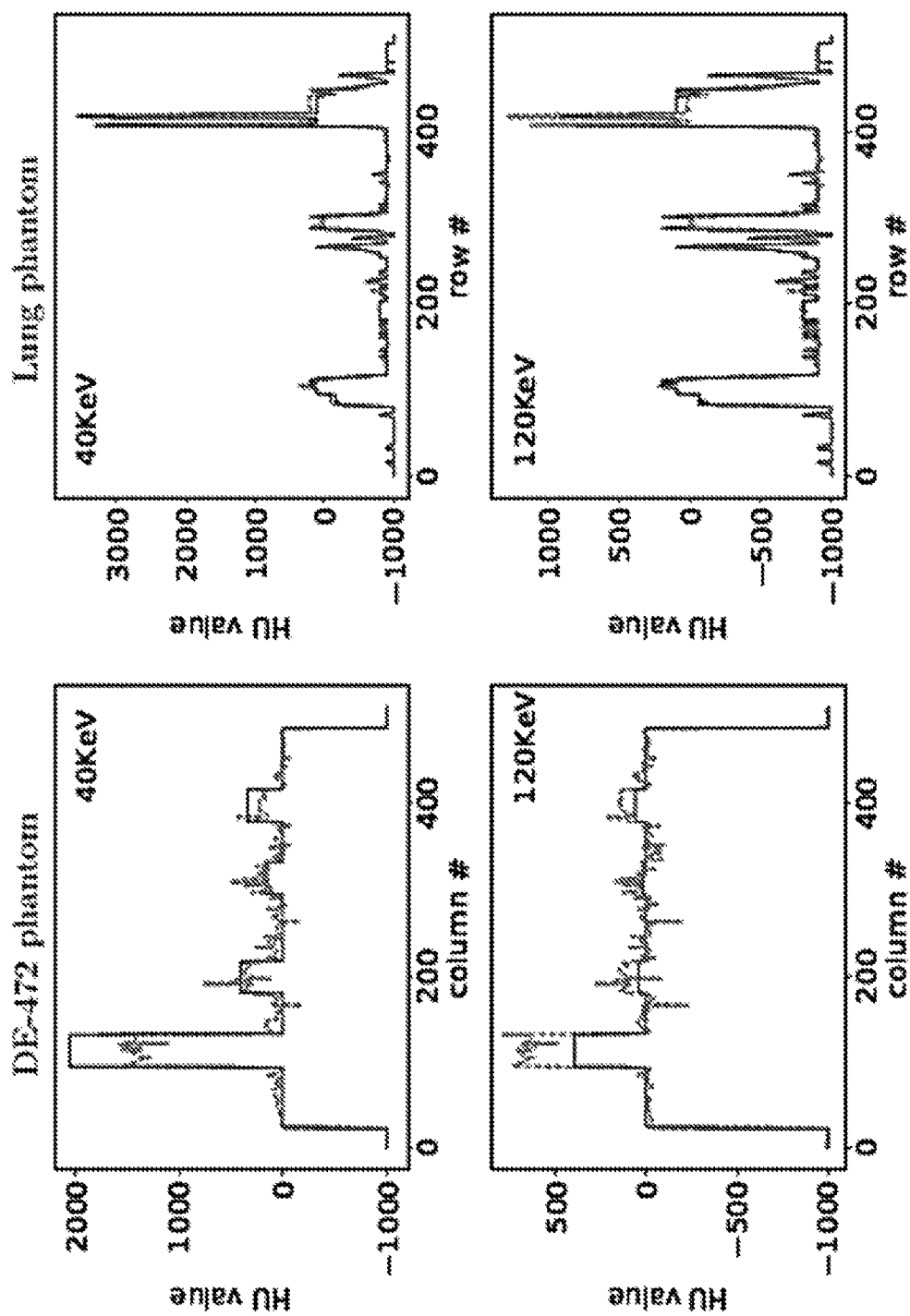
FIG. 20 depicts plots of profiles of the reconstructed and truth monochromatic images along the horizontal and vertical lines indicated in FIG. 14 to reveal quantitative differences in accordance with an illustrative embodiment.

FIG. 19 illustrates reconstruction results for both phantoms from data acquired with the limited-angular-range configurations in accordance with an illustrative embodiment. Specifically, FIG. 19 illustrates water- and bone-basis images (row 1), 40- and 120-KeV monochromatic images (row 2), and zoomed-in views of ROI images (row 3) similar to those in row 3 of FIG. 14 from limited-angular-range-scan data of the DE-472 and lung phantoms, respectively, with display windows [0, 1.5] (row 1), [−1000, 1000] HU (row 2), and [−500, 500] HU (row 3, DE-472 phantom) and [−1000, 200] HU (row 3, lung phantom). Monochromatic image at 40 KeV for the DE-472 phantom shows visible artifacts, due to the poor conditioning of the DD-data model for the limited-angular-range scan considered and the presence of high-concentration calcium and iodine inserts in the phantom, while the monochromatic image at 120 KeV reveals less artifacts. On the other hand, monochromatic images for the lung phantom appear to be with artifacts much less prominent than those for the DE-472 phantom. In addition to reconstruction visualization, FIG. 20 depicts plots of profiles of the reconstructed and truth monochromatic images along the horizontal and vertical lines indicated in FIG. 14 to reveal quantitative differences in accordance with an illustrative embodiment. The lung-phantom reconstructions agree reasonably well with their truths for both energy levels, whereas some differences between the DE-phantom reconstructions and truth counterparts can be observed especially for the limited-angular-range configuration.

With regard to configurations with varying illumination coverages, FIGS. 7-8 illustrate two additional non-standard configurations, which involve varying illumination coverage, and are referred to as the split- and block-illumination configurations, respectively. As discussed above, in the configurations, low- and high-kVp data are collected, respectively, with two adjacent and multiple adjacent alternating illumination coverages at each of 640 views uniformly distributed over $2\pi$. The configurations can be achieved through, e.g., the use of a beam blocker in front of the X-ray source and/or detector blocks with different energy responses.

In the split-illumination configuration, the linear detector with 1024 bins (i.e., 400-mm length) is divided into two adjacent segments of equal length with 512 bins (i.e., 200-mm length), and the low or high kVp beam illuminates one of the two segments, respectively. Therefore, matrices $\mathcal{A}^{[1]}$ and $\mathcal{A}^{[2]}$ are of identical dimensions $J^{[1]}=J^{[2]}=640\times512$ and $I=512\times512$. Using the strategy described herein, $\varepsilon=0.0118$ and 0.008 are selected, respectively, for the DE-472- and lung-phantom studies described herein.

In the block-illumination configuration, the linear detector is divided into two sets of interlaced, adjacent detector blocks of equal length with 32 bins (i.e., 12.5-mm length), as shown in FIGS. 7-8, and the low or high kVp beam illuminates one of the two sets of detector blocks, respectively. Therefore, matrices $\mathcal{A}^{[1]}$ and $\mathcal{A}^{[2]}$ are of identical dimensions $J^{[1]}=J^{[2]}=640\times512$ and $I=512\times512$. Using the strategy described herein, $\varepsilon=0.0121$ and 0.0089 is selected, respectively, for the DE-472- and lung-phantom studies.

Figure 21:
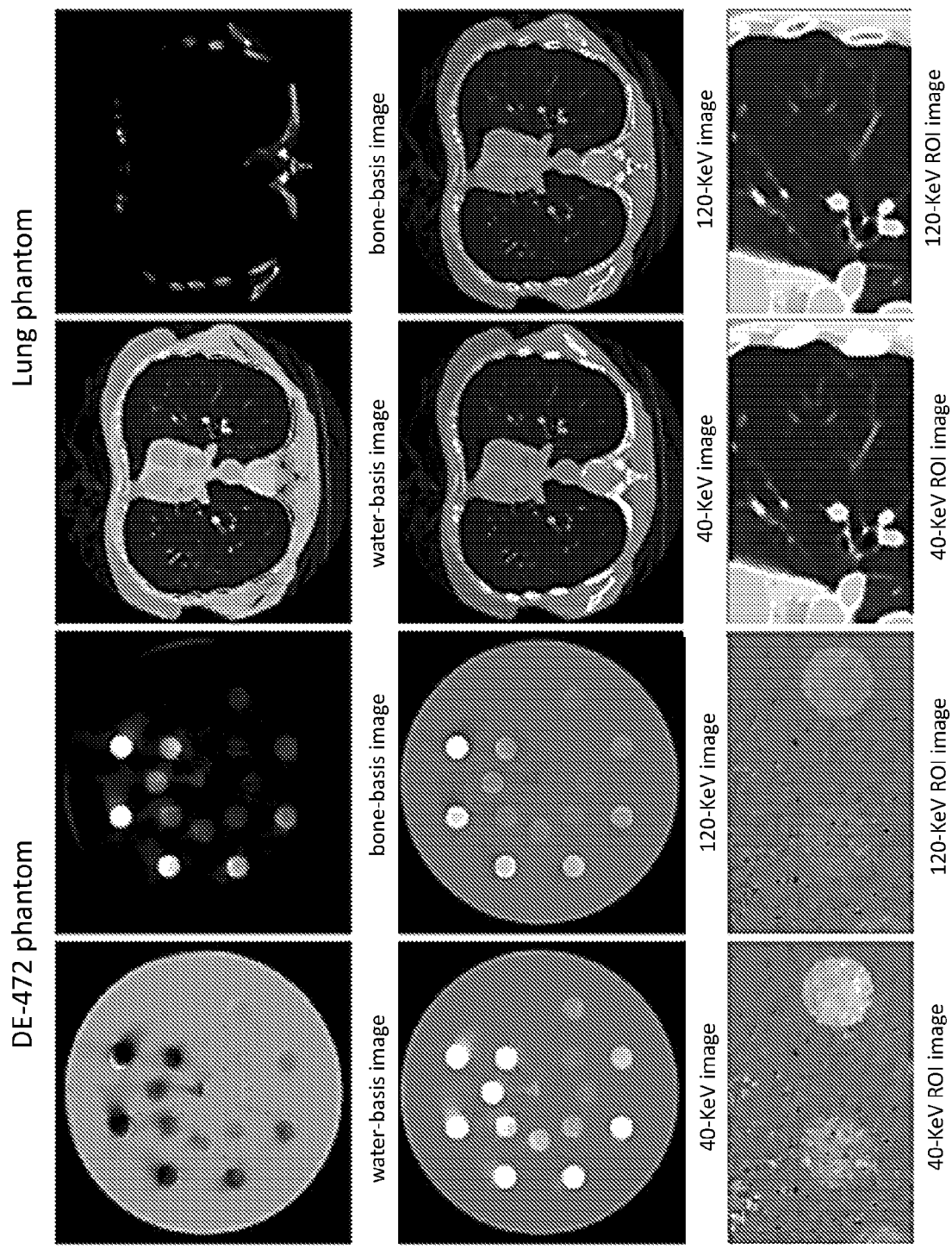
FIG. 21 illustrates illumination reconstruction results for both phantoms from data acquired with the split-illumination configuration in accordance with an illustrative embodiment.
Figure 22:
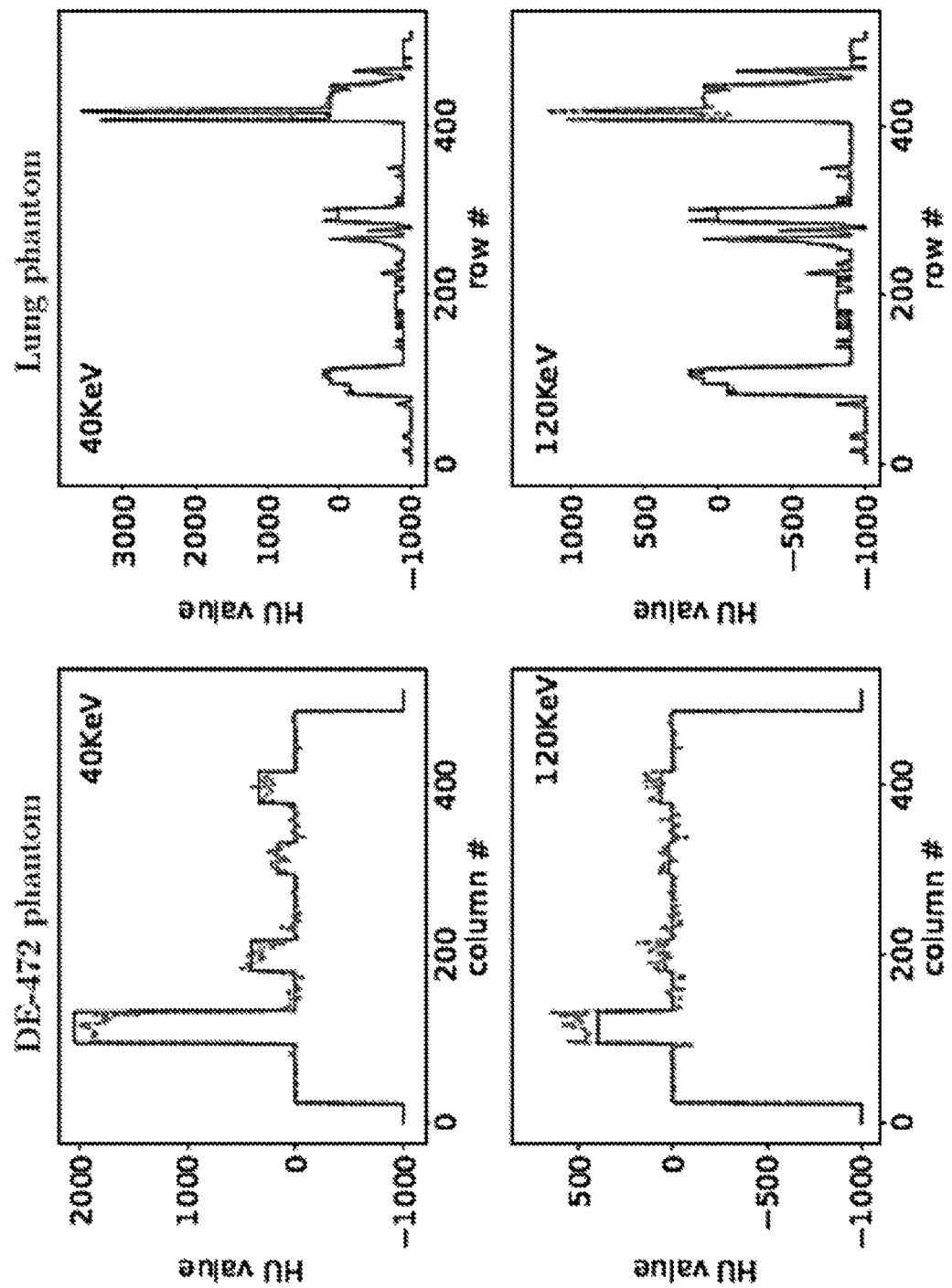
FIG. 22 depicts plots of profiles of the reconstructed and truth monochromatic images along the horizontal and vertical lines indicated in row 2 of FIG. 14 in accordance with an illustrative embodiment.

FIG. 21 illustrates illumination reconstruction results for both phantoms from data acquired with the split-illumination configuration in accordance with an illustrative embodiment. More specifically, FIG. 21 shows water- and bone-basis images (row 1), 40- and 120-KeV monochromatic images (row 2), and zoomed-in views of ROI images (row 3) similar to those in row 3 of FIG. 14 from split-illumination-scan data of the DE-472 and lung phantoms, respectively, with display windows [0, 1.5] (row 1), [−1000, 1000] HU (row 2), and [−500, 500] HU (row 3, DE-472 phantom) and [−1000, 200] HU (row 3, lung phantom). The monochromatic image at 40 KeV for the DE-472 phantom show some visible artifacts, while the monochromatic image at 120 KeV reveals less artifacts. Conversely, monochromatic images for the lung phantom appear to reveal few artifacts. In addition to reconstruction visualization, FIG. 22 depicts plots of profiles of the reconstructed and truth monochromatic images along the horizontal and vertical lines indicated in row 2 of FIG. 14 in accordance with an illustrative embodiment. More specifically, FIG. 22 illustrates profiles of reconstructed (dashed) and truth (solid) monochromatic images at 40 and 120 KeV along the horizontal and vertical lines indicated in row 2 of FIG. 14 from split-illumination-scan data of the DE-472 and lung phantoms, respectively. It can be seen that while some quantitative difference between the reconstructed and truth monochromatic images for the DE-472 phantom can be observed, the truth and reconstructed monochromatic images agree reasonably well quantitatively for the lung phantom.

Figure 23:
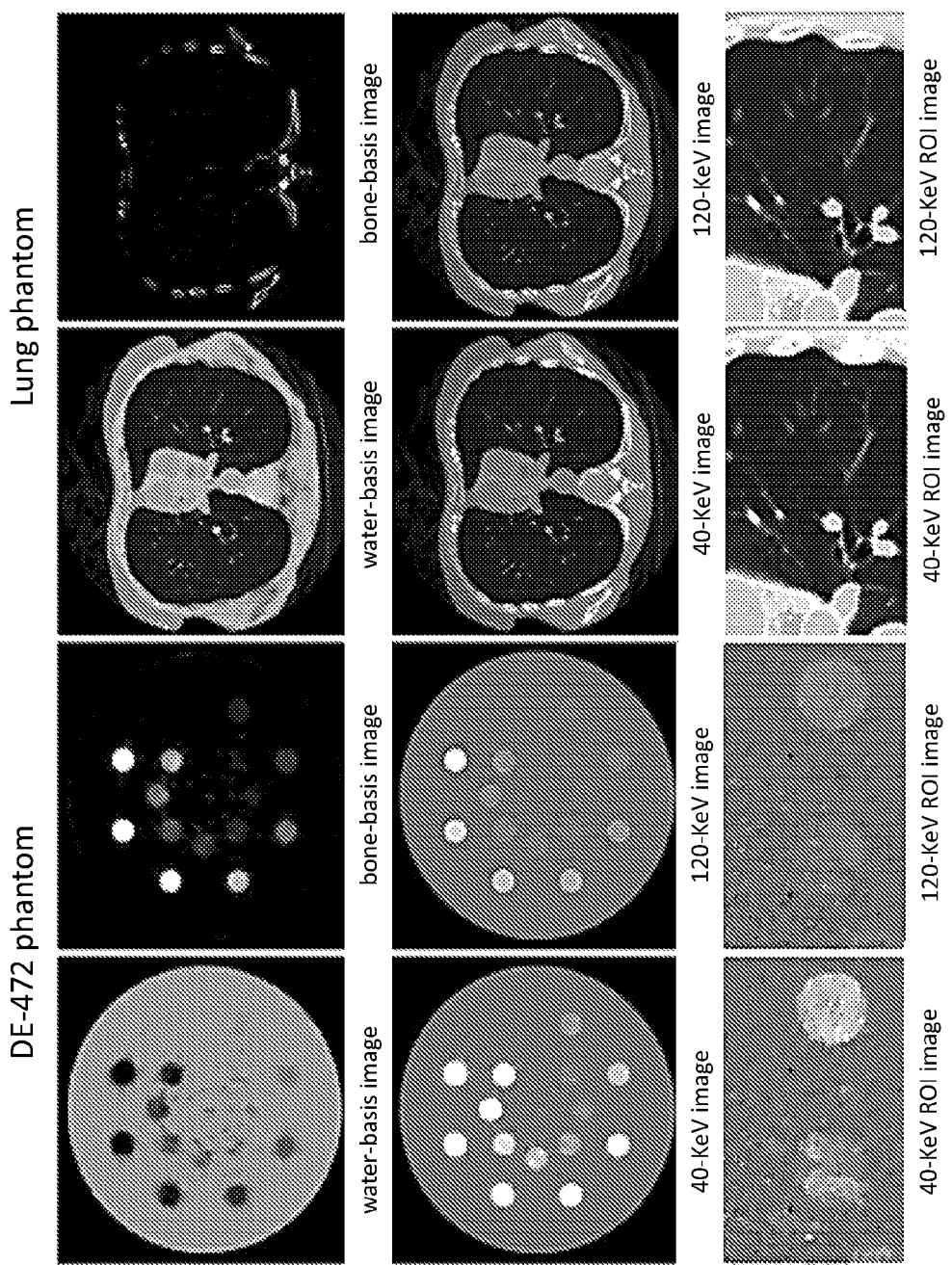
FIG. 23 illustrates water- and bone-basis images (row 1), 40- and 120-KeV monochromatic images (row 2), and zoomed-in views of ROI images (row 3) similar to those in row 3 of FIG. 14 from block-illumination-scan data of the DE-472 and lung phantoms, respectively, in accordance with an illustrative embodiment.
Figure 24:
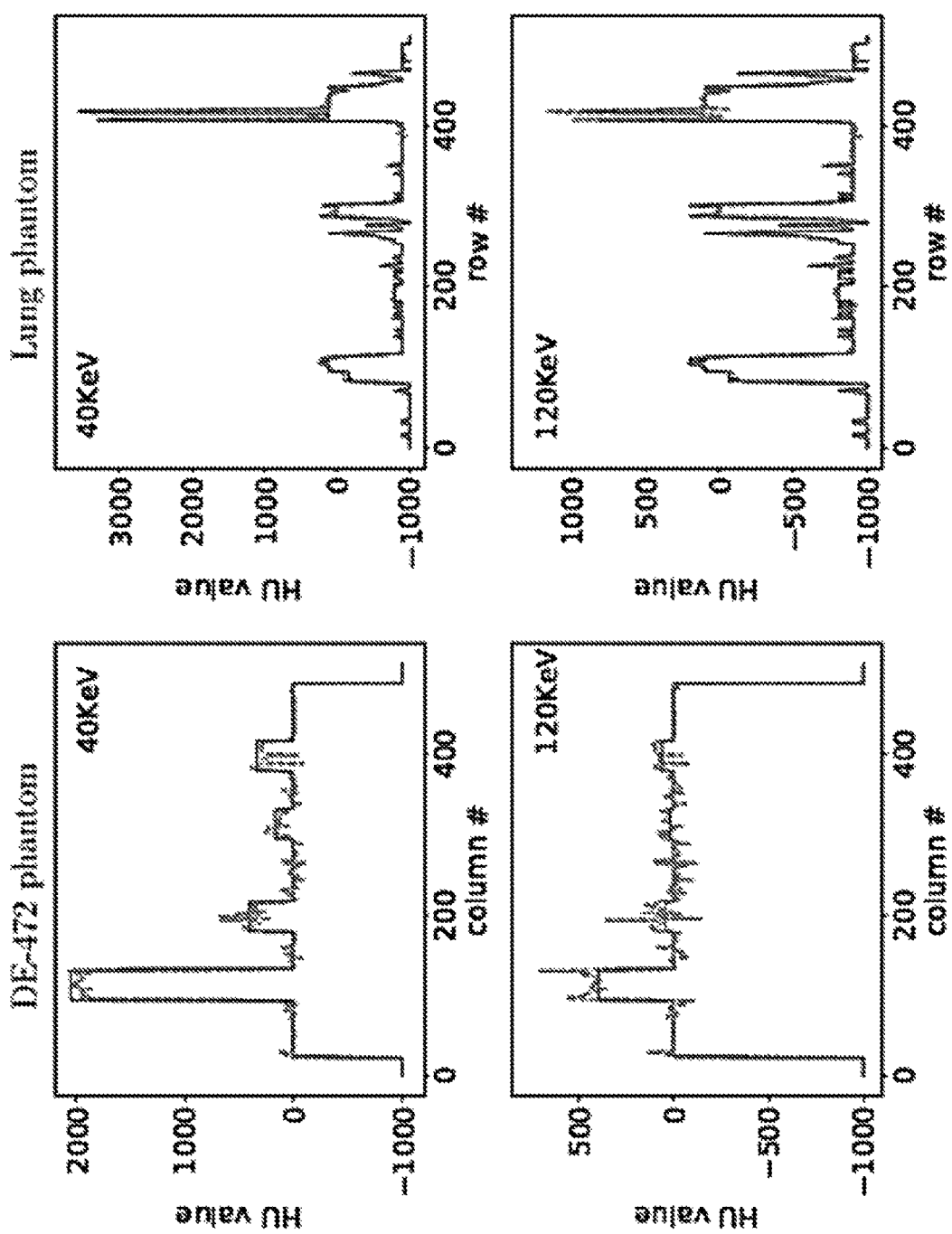
FIG. 24 illustrates profiles of reconstructed (dashed) and truth (solid) monochromatic energy images at 40 and 120 KeV along the horizontal and vertical lines indicated in row 2 of FIG. 14 from block-illumination-scan data of the DE-472 and lung phantoms, respectively, in accordance with an illustrative embodiment.

FIG. 23 illustrates water- and bone-basis images (row 1), 40- and 120-KeV monochromatic images (row 2), and zoomed-in views of ROI images (row 3) similar to those in row 3 of FIG. 14 from block-illumination-scan data of the DE-472 and lung phantoms, respectively, in accordance with an illustrative embodiment. FIG. 23 shows display windows [0, 1.5] (row 1), [−1000, 1000] HU (row 2), and [−500, 500] HU (row 3, DE-472 phantom) and [−1000, 200] HU (row 3, lung phantom). FIG. 24 illustrates profiles of reconstructed (dashed) and truth (solid) monochromatic energy images at 40 and 120 KeV along the horizontal and vertical lines indicated in row 2 of FIG. 14 from block-illumination-scan data of the DE-472 and lung phantoms, respectively, in accordance with an illustrative embodiment. In FIGS. 23-24, reconstruction results are displayed for both phantoms from data acquired with the block-illumination configurations. Based upon the reconstruction results, observations similar to those for the split-illumination configuration can be made.

Thus, a one-step, optimization-based approach for image reconstruction in MSXT has been described, particularly demonstrating application to various different scan configurations of potential practical significance. The challenge of optimization-based image reconstruction in MSXT stems from its non-linear data model that can lead to a non-convex optimization program for which no mathematically exact solver is available for achieving its globally optimal solution. A non-convex optimization program is disclosed, its KKT condition is derived, and a methodology is used numerically to solve the program for image reconstruction in MSXT. A property of the methodology disclosed is that it may reconstruct images in MSXT without the use of multiple spectral measurements for the same ray. Application of this property of the methodology enables scan configurations of practical interest in terms of potentially lowered hardware cost, enhanced scanning flexibility, and reduced imaging dose/time in MSXT.

Further, in addition to the standard, full-scan configuration in MSXT, a plurality of non-standard configurations are disclosed with different designs of scanning angular range and illumination coverage each of which acquires only a portion of data of the full-scan configuration. The non-standard configurations may be considered because they can readily be implemented on a standard CT scanner employing regular X-ray tubes and energy-integrating detectors without invoking hardware additions and/or modifications to the scanner. The study results support that the configurations considered may be enabled by the methodology proposed to yield monochromatic images comparable to those of the full-scan configuration both visually and quantitatively. While scan-configuration have been illustrated that enable dual-energy CT in the work, the methodology may accommodate multiple (>2) spectral scans and/or a variety of configurations with different designs of source trajectory and/or illumination coverage tailored to specific applications.

The enabling effectiveness of the methodology may depend upon one or more factors, such as: sampling conditions and their impact on the data-model conditioning for a specific configuration, appropriateness of spectra used, anatomy complexity of subjects imaged, decomposition error, and data noise. In the presence of data inconsistencies such as decomposition error and statistical noise, some banding artifacts near high contrast structures in DE-472-phantom images are observed to appear stronger understandably for the limited-angular-range configuration than for other configurations, suggesting that the effectiveness of the methodology in enabling, e.g., a configuration with a considerably limited angular-range, decreases relative to that for other configurations. Conversely, the results show that reconstructions of the lung phantom appear to be robust for the configurations considered.

It is known that any optimization-based reconstruction may involve some parameters. In the optimization-based reconstruction disclosed, parameter E plays a role in impacting the image reconstruction. Metrics have been devised quantitatively to select E specific to the simulation-data study performed. However, other methods through which to determine E in realistic, practical applications are contemplated. In particular, metrics specific to the actual tasks may be designed for the determination of parameter E in practical applications.

As discussed above, in one implementation, the methodology derivation relies upon the linearization of the model (such as the non-linear DD-data model). There may be multiple ways in which to transform (e.g., linearize) the model. In particular, discussed below is a specific case representative of multiple linearization methodologies. In this regard, it is contemplated that there are different ways than that disclosed for the linearization. Further, a specific optimization program is disclosed that includes the data divergence in a $l_2$-norm form. Different optimization programs are contemplated that can lead to different reconstructions, particularly in the presence of data inconsistencies such as noise. Thus, optimization programs of different forms are contemplated (e.g., containing the KL or other data divergences) that enable scan configurations and obtain reconstructions of specific application interest. Additional image constraints other than the image-TV constraint may also be incorporated into the programs. For example, appropriate constraints on the basis-image values may be imposed for potentially improving image reconstruction in MSXT, especially for the limited-angular-range scan configuration.

The following is one example of a derivation of the local optimality condition. Using equation 1, one can obtain monochromatic energy images as $f_n = \Sigma_k \mu_{kn} b_k$ at N energies, where n=1, 2, ..., N. Lower- or upper-bound constraints on the images can be written as:

$$\Sigma_k \tilde{\mu}_{kn} b_k + p_n \circ 0 \text{ for } n=1,2,\ldots,N, \qquad \text{Eq. 25:}$$

where $p_n$ is a scalar for specifying the upper or lower bound of the nth monochromatic image, and $\tilde{\mu}_{kn} = \pm \mu_{kn}$ with the negative sign used to impose a lower bound of image values, or simply non-negativity, on the monochromatic images.

Equation 25 can be rewritten in a linear form of b as:

$$\mathcal{Q}_n b + p_n \circ 0 \text{ for } n=1,2,\ldots,N, \text{ where} \qquad \text{Eq. 26:}$$

$$\mathcal{Q}_n = (\tilde{\mu}_{1n} \mathcal{I}, \tilde{\mu}_{2n} \mathcal{I}, \ldots, \tilde{\mu}_{Kn} \mathcal{I}), \qquad \text{Eq. 27:}$$

$$p_n = (p_n, p_n, \ldots)^T, \text{ and} \qquad \text{Eq. 28:}$$

and $\mathcal{I}$ denotes the identity matrix of size I×I.

An optimization program may be considered in the form of:

$$b^* = \min_b \Psi(b), \qquad \text{Eq. 29}$$

$$\text{s.t. } \Phi^2\left(b; g_{\mathcal{M}}\right) \leq \varepsilon^2, \text{ and} \qquad \text{Eq. 30}$$

$$\mathcal{Q}_n b + p_n \circ 0 \text{ for } n = 1, 2, \ldots, N, \qquad \text{Eq. 31}$$

and derive its first-order optimality conditions, e.g., the Karush-Kuhn-Tucker (KKT) conditions. It can readily be shown that the optimization programs in equations 2)-31 and 9 are equivalent when N=K, $p_n$=0, and $\tilde{\mu}_{kn}$=1 for k=n (0 otherwise). Therefore, the derived KKT conditions for the former are applicable to the latter.

The Lagrangian of the optimization program in equation equations 29-31 is given as:

$$L(b, v, \{\lambda_n\}) = \Psi(b) + v(\Phi^2(b) - \varepsilon^2) + \Sigma_n \lambda_n^T (\mathcal{Q}_n b + p_n), \qquad \text{Eq. 32:}$$

where scalar v and vectors $\{\lambda_n\}$ are the Lagrangian multipliers. The KKT conditions can thus be expressed as:

$$\Phi^2(b^*) \leq \varepsilon^2, \qquad \text{Eq. 33:}$$

$$\mathcal{Q}_n b^* + p_n \circ 0, n=1,2,\ldots,N \qquad \text{Eq. 34:}$$

$$v^* \geq 0, \qquad \text{Eq. 35:}$$

$$\lambda_n^* \pm 0, n=1,2,\ldots,N, \qquad \text{Eq. 36:}$$

$$\nabla_b L(b^*, v^*, \{\lambda_n\}) = \nabla_b \Psi(b^*) + v^* \nabla_b \Phi^2(b^*) + \Sigma_n \mathcal{Q}_n^T \lambda_n^* = 0, \qquad \text{Eq. 37:}$$

$$v^*(\Phi^2(b^*) - \varepsilon^2) = 0, \text{ and} \qquad \text{Eq. 38:}$$

$$\lambda_n^{*T} (\mathcal{Q}_n b^* + p_n) = 0, n=1,2,\ldots,N, \qquad \text{Eq. 39:}$$

where $b^*$ and $(v^*, \{\lambda_n^*\})$ are optimal variables and Lagrangian multipliers for the optimization problem. Given the specific form of $\mathcal{Q}_n$ in equation 26, the last part of the gradient of the Lagrangian in equation 37 can be simplified as:

$$\Sigma_n \mathcal{Q}_n^T \lambda_n^* = (\Sigma_n \tilde{\mu}_{1n} \lambda_n^*, \Sigma_n \tilde{\mu}_{2n} \lambda_n^*, \ldots, \Sigma_n \tilde{\mu}_{Kn} \lambda_n^*)^T. \qquad \text{Eq. 40:}$$

In general, for non-zero equation $\tilde{\mu}_{kn}$ has zero entries wherever all $\{\lambda_n^*\}$ have zeros at the same entries. Based on this observation, one may turn to the complementary slackness in equation 39, which follows:

$$\begin{cases} \lambda_{ni}^* = 0 & \text{if } (Q_n b^*)_i + p_n > 0, \\ \lambda_{ni}^* > 0 & \text{if } (Q_n b^*)_i + p_n = 0. \end{cases} \quad \text{Eq. 41}$$

Vector $1_n(b)$ of size I is used to denote an identity function, whose elements are:

$$1_n(b)_i = \begin{cases} 1 & \text{if } (Q_n b)_i + p_n > 0, \\ 0 & \text{if } (Q_n b)_i + p_n = 0, \end{cases} \quad \text{Eq. 42}$$

and diag(x) a function that yields a diagonal matrix with the elements of vector x placed along the diagonal line, as:

$$\text{diag}(x) = \begin{pmatrix} x_0 & & & \\ & \ddots & & \\ & & x_i & \\ & & & \ddots \\ & & & & x_{I-1} \end{pmatrix}. \quad \text{Eq. 43}$$

Subsequently, considering all N constraints, a matrix is constructed as the product of N diagonal matrices:

$$\mathcal{D}(b) = \Pi_{n=1}^N \text{diag}(1_n(b)). \quad \text{Eq. 44:}$$

As a result, $\mathcal{D}(b)$ is also diagonal of size I and it picks out those image pixels at which location the N linear constraints in equation 25 or 26 are strictly satisfied simultaneously. Finally, K identical $\mathcal{D}(b)$ is used and placed in a diagonal line to form a bigger diagonal matrix $\mathcal{D}'(b)$ of size I×K as:

$$\mathcal{D}'(b) = \begin{pmatrix} \mathcal{D}(b) & & \\ & \ddots & \\ & & \mathcal{D}(b) \end{pmatrix}. \quad \text{Eq. 45}$$

Given the meaning of $\mathcal{D}(b)$ as described above, left-multiplying $\mathcal{D}'(b^*)$ to both sides of equations 40 yields:

$$\mathcal{D}'(b^*) \sum_n Q_n^T \lambda_n^* = \left( \mathcal{D}(b^*) \sum_n \tilde{\mu}_{1n} \lambda_n^*, \; \mathcal{D}(b^*) \sum_n \tilde{\mu}_{2n} \lambda_n^*, \ldots, \; \mathcal{D}(b^*) \sum_n \tilde{\mu}_{Kn} \lambda_n^* \right)^T$$

This can simplify the first order optimality condition in equation 37 as:

$d_{TV}(b^*) + d_{data}(b^*) = 0$, where $d_{TV}(b^*) = \mathcal{D}'(b^*) \nabla_b \Psi(b^*)$ and $d_{data}(b^*) = v^* \mathcal{D}(b^*) \nabla_b \Phi^2(b^*)$. Eq. 46:

Equation 35 states that $v^*$ is non-negative (dual feasibility), and the complementary slackness in equation 38 states that $v^*$ can only be zero when the data fidelity constraint is not active. For practical solutions that are non-trivial, e.g., other than non-negative flat images, the data fidelity constraint is always active. Therefore, it is desired that $v^* > 0$ in practical situations, which leads to that $d_{TV}(b^*)$ and $d_{data}(b^*)$ shall be oppositely co-linear, or $$c_\alpha \equiv \hat{d}_{TV}^T(b^*) \hat{d}_{data}(b^*) = -1, \quad \text{Eq. 47}$$

where $\hat{d}_{TV}(b^*) = d_{TV}(b^*)/|d_{TV}(b^*)|$ and $\hat{d}_{data}(b^*) = d_{data}(b^*)/|d_{data}(b^*)|$ are the normalized vectors.

For computing $d_{TV}(b^*)$, using $\Psi(b)$ in equation 10, there is:

$$\nabla_b \Psi(b^*) = \sum_k \nabla_b \|b_k^*\|_{TV}, \quad \text{Eq. 48}$$

where $$\nabla_b \|b_k^*\|_{TV} = \begin{cases} \nabla_{b_i} \|b_k^*\|_{TV} & \text{if } b_i \in b_k, \\ 0 & \text{if } b_i \notin b_k. \end{cases}$$

As the $l_1$-norm function is non-smooth, TV gradients, or $\nabla_{b_k} \|b_k^*\|_{TV}$, are computed based on an approximation of a smoothed version.

On the other hand, for computing $d_{data}(b^*)$, there is:

$$\Phi^2(b) = (g_M{}^T g_M)^{-1}(g(b) - g_M)^T(g(b) - g_M). \quad \text{Eq. 49:}$$

Taking its gradient yields:

$$\nabla_b \Phi^2(b) = 2(g_M{}^T g_M)^{-1} J(g(b),b)(g(b) - g_M), \quad \text{Eq. 50:}$$

where Jacobian matrix $J(y(x), x)$ is given by:

$$J(y(x), x) = \begin{pmatrix} \dfrac{\partial y(x)_1}{\partial x_1} & \dfrac{\partial y(x)_2}{\partial x_1} & \cdots \\ \dfrac{\partial y(x)_1}{\partial x_2} & \dfrac{\partial y(x)_2}{\partial x_2} & \cdots \\ \vdots & \vdots & \ddots \end{pmatrix}, \quad \text{Eq. 51}$$

where $y(x)_j$ and $x_i$ are the j-th and i-th elements of vectors $y(x)$ and $x$, respectively. Given the concatenated form of the aggregate basis image vector as $b = (b_1^T, b_2^T, \ldots b_K^T)^T$ and the dimension of vector $g(b)$ being $J' \equiv \Sigma_s J^{[s]}$, where $J^{[s]}$ is the size of data vector $g^{[s]}(b)$ for spectral set s, the Jacobian in equation 50 can be re-expressed as:

$$J(g(b), b) = \begin{pmatrix} \nabla_{b_1} g(b)_1, & \nabla_{b_1} g(b)_2, & \cdots & \nabla_{b_1} g(b)_{J'} \\ \nabla_{b_2} g(b)_1, & \nabla_{b_2} g(b)_2, & \cdots & \nabla_{b_2} g(b)_{J'} \\ \vdots & \vdots & \ddots & \vdots \\ \nabla_{b_K} g(b)_1, & \nabla_{b_K} g(b)_2, & \cdots & \nabla_{b_K} g(b)_{J'} \end{pmatrix}. \quad \text{Eq. 52}$$

In equation 8, the element of data vector $g(b)$ may depend upon spectral set index s and ray index j. In this derivation, instead, a single index j' is used for the aggregate data vector $g(b)$, as $j' = j + (s-1) \times J^{[s-1]}$ and $$g_{j'}(b) = g_j^{[s]}(b) = -\ln \Sigma_m q_{jm}^{[s]} \exp(-\Sigma_k \mu_{km} a_j^{[s]} b_k) \quad \text{Eq. 53:}$$

As a result, the gradient of $g_{j'}(b)$ with respect to basis image $b_k$ can be written as:

$$\nabla_{b_k} g_{j'}(b) = (\Sigma_m t_{j'm})^{-1} (\Sigma_m \mu_{km} t_{j'm}) a_{j'}^T, \text{ where} \quad \text{Eq. 54:}$$

$$t_{j'm} = q_{jm}^{[s]} \exp(-\Sigma_k \mu_{km} a_j^{[s]} b_k), \text{ and} \quad \text{Eq. 55:}$$

$$a_{j'} = a_j^{[s]}. \quad \text{Eq. 56:}$$

Finally, replacing equations 52 and 54 into equation 50 yields:

$$\nabla_b \Phi^2(b) = 2(g_M{}^T g_M)^{-1} J(g(b),b)(g(b) - g_m) \quad \text{Eq. 57}$$

$$= \frac{2}{g_M^T g_M} \begin{pmatrix} \sum_{j'} (g_{j'} - g_{Mj'}) \nabla_{b_1} g_{j'} \\ \sum_{j'} (g_{j'} - g_{Mj'}) \nabla_{b_2} g_{j'} \\ \vdots \\ \sum_{j'} (g_{j'} - g_{Mj'}) \nabla_{b_K} g_{j'} \end{pmatrix} \quad \text{Eq. 58}$$

$$= \frac{2}{g_M^T g_M} \begin{pmatrix} \sum_{j'} \frac{(g_{j'} - g_{Mj'}) \sum_m \mu'_{1m} t_{j'm}}{\sum_m t_{j'm}} a_{j'}^T \\ \sum_{j'} \frac{(g_{j'} - g_{Mj'}) \sum_m \mu'_{2m} t_{j'm}}{\sum_m t_{j'm}} a_{j'}^T \\ \vdots \text{ 5 pt} \\ \sum_{j'} \frac{(g_{j'} - g_{Mj'}) \sum_m \mu'_{Km} t_{j'm}}{\sum_m t_{j'm}} a_{j'}^T \end{pmatrix} \quad \text{Eq. 59}$$

As an alternative to the basis and monochromatic images discussed above, discrete image arrays may be considered, with a discrete image being denoted in a vector form of size I, where I is the total number of voxels of the image array, and entry i in an image vector is the image value within voxel i, where $i \in \{0,1, \ldots, I-1\}$. Also, one may refer to the product of the incident X-ray beam spectrum and the detector energy response as the X-ray spectrum, and express it as a vector of size M in which each entry denotes the spectrum value with energy bin m, where $m \in \{1, 2, \ldots, M\}$. In dual-energy CT imaging, one seeks to determine the X-ray linear-attenuation coefficient distribution, which is a two-variable function of X-ray energy and spatial coordinates. For a given energy m, the linear-attenuation coefficient distribution can be expressed as vector $f_m$ of size I in which each entry $f_{im}$ indicates the value of the linear-attenuation coefficient at voxel i for energy m. In an attempt to avoid solving directly for a two-variable function, $f_m'$ may be re-expressed as:

$$f_m' = f_m + \Delta f_m, \text{ where} \quad \text{Eq. 60:}$$

$$f_m = \mu_{1m} b_1 + \mu_{2m} b_2. \quad \text{Eq. 61:}$$

Vectors $b_1$ and $b_2$ denote basis images of size I, $\mu_{1m}$ and $\mu_{2m}$ the decomposition coefficients, and $\Delta f_m$, the decomposition error. When different sets of decomposition coefficients are considered, one obtains different decompositions of the linear attenuation coefficients, thus different basis images and decomposition errors. The variable $f_m$ is referred to as the monochromatic image at energy m. The water and bone mass-attenuation coefficients may be used as the decomposition coefficients, and thus may refer to the decomposition in equation 61 as a material-based decomposition. Not considering the decomposition error from insufficient bases, the determination of $f_m'$ is simplified to determinating basis images $b_1$ and $b_2$, which are independent of energy m. Once the basis images are determined, one can use equation 2 to obtain the monochromatic image $f_m$, at energy m, which is used then as an approximation of the linear-attenuation coefficients $f_m'$ f interest.

Further, the data model for dual-energy imaging may be expressed in multiple ways. Specifically, in dual-energy CT imaging, measurement may be made with spectrum s, for each ray connecting a detector bin and the X-ray source at a given source position. The total number of rays measured is denoted as $J^{[s]}$, which is the product of the number of rays measured at a source position and the number of source positions for a given X-ray spectrum s. Considering a two-basis decomposition model in equation 61, one can readily express the data model for a ray measurement with spectrum s as:

$$g_j^{[s]}(b_1, b_2) = -\ln \Sigma_m q_{jm}^{[s]} \exp(-\Sigma_i a_{ji}^{[s]} f_{im}) = -\ln \Sigma_m q_{jm}^{[s]} \exp(-\Sigma_i a_{ji}^{[s]} (\mu_{1m} b_{1i} + \mu_{2m} b_{2i})), \quad \text{Eq. 62:}$$

where $j \in \{0, \ldots, J^{[s]}-1\}$ is a ray index for either low (s=1) or high (s=2) kVp scan, $g_j^{[s]}(b_1, b_2)$ denotes the model data for the jth ray in scan s, $q_{jm}^{[s]}$ the ray-dependent, normalized X-ray spectrum, satisfying $\Sigma_m q_{jm}^{[s]}=1$, at energy m for the jth ray in scan s, and $\alpha_{ji}^{[s]}$ the intersection length of the jth ray in scan s with the ith voxel. The data model is a non-linear function of basis images $b_1$ and $b_2$.

The data model in equation 62 can be re-written as:

$$g_j^{[s]}(b_1, b_2) = \bar{g}_j^{[s]}(b_1, b_2) + \Delta g_j^{[s]}(b_1, b_2), \text{ where} \quad \text{Eq. 63:}$$

$$\bar{g}_j^{[s]}(b_1, b_2) = \Sigma_i a_{ji}^{[s]} (\bar{\mu}_{j1}^{[s]} b_{1i} + \bar{\mu}_{j2}^{[s]} b_{2i}), \text{ and} \quad \text{Eq. 64:}$$

$$\Delta g_j^{[s]}(b_1, b_2) = -\ln \Sigma_m q_{jm}^{[s]} \exp(-\Sigma_i a_{ji}^{[s]} (\Delta \mu_{j1m}^{[s]} b_{1i} + \Delta \mu_{j2m}^{[s]} b_{2i})). \quad \text{Eq. 65:}$$

The term $\bar{\mu}_{jk}^{[s]} = \Sigma_m q_{jm}^{[s]} \mu_{km}$ is an energy-independent term, taken as the spectrum-weighted average of $\mu_{km}$ over energy m, $\Delta \mu_{jkm}^{[s]} = \mu_{km} - \bar{\mu}_{jk}^{[s]}$ remains energy dependent, and k=1 and 2 indexes the basis material. It is noted that $\bar{g}_j^{[s]}(b_1, b_2)$ is a linear function of basis images $b_1$ and $b_2$, while $\Delta g_j^{[s]}(b_1, b_2)$ contributes to the non-linearity of the data model.

For spectrum s, data vector $g^{[s]}(b_1, b_2)$ is formed of size $J^{[s]}$, with elements $g_j^{[s]}(b_1, b_2)$, where $j \in \{0, 1, \ldots, J^{[s]}-1\}$. Similarly, one can form additional data vectors $\bar{g}^{[s]}(b_1, b_2)$ and $\Delta g^{[s]}(b_1, b_2)$, for s=1 and 2, in the same fashion as $g^{[s]}(b_1, b_2)$, with elements $\bar{g}_j^{[s]}(b_1, b_2)$ and $\Delta g_j^{[s]}(b_1, b_2)$ given in equations 64 and 65, respectively. Also, let $\mathcal{A}^{[s]}$ denote the discrete X-ray transform matrix of dimension $J^{[s]} \times I$ with $\alpha_{ji}^{[s]}$ as its element for spectrum s, and $U_k^{[s]}$ a diagonal matrix of size $J^{[s]}$ with $\bar{\mu}_{jk}^{[s]}$ as its diagonal element. Subsequently, the data model in equation 63 for an individual ray can be grouped into a matrix form for all of the rays from the low (s=1) and high (s=2) kVp scans as:

$$\begin{pmatrix} g^{[1]}(b_1, b_2) - \Delta g^{[1]}(b_1, b_2) \\ g^{[2]}(b_1, b_2) - \Delta g^{[2]}(b_1, b_2) \end{pmatrix} = \begin{pmatrix} \bar{g}^{[1]}(b_1, b_2) \\ \bar{g}^{[2]}(b_1, b_2) \end{pmatrix}, \text{ where} \quad \text{Eq. 66}$$

$$\begin{pmatrix} \bar{g}^{[1]}(b_1, b_2) \\ \bar{g}^{[2]}(b_1, b_2) \end{pmatrix} = \begin{pmatrix} \mathcal{U}_1^{[1]} \mathcal{A}^{[1]}, \mathcal{U}_2^{[1]} \mathcal{A}^{[1]} \\ \mathcal{U}_1^{[2]} \mathcal{A}^{[2]}, \mathcal{U}_2^{[2]} \mathcal{A}^{[2]} \end{pmatrix} \begin{pmatrix} b_1 \\ b_2 \end{pmatrix}. \quad \text{Eq. 67}$$

Similarly, the non-convex optimization program may be expressed in one of several ways. For discussion convenience, aggregated vectors $\bar{g}(b_1, b_2) = (\bar{g}^{[1]T}(b_1, b_2), \bar{g}^{[2]T}(b_1, b_2))^T$ and $\Delta g(b_1, b_2) = (\Delta g^{[1]T}(b_1, b_2), \Delta g^{[2]T}(b_1, b_2))^T$ are formed, where symbol T indicates a transpose operation. Letting vectors $g_M^{[1]T}$ and $g_M^{[2]T}$ of sizes $J^{[1]}$ and $J^{[2]}$ denote data actually measured with spectra s=1 and 2, a measured data vector, $g_M = (g_M^{[1]T}, g_M^{[2]T})^T$, is formed in an aggregate form. Using the aggregated data vectors, one may then formulate the basis images as a solution to the constrained optimization program designed as:

$$(b_1^*, b_2^*) = \arg\min_{b_1, b_2}(\|b_1\|_{TV} + \|b_2\|_{TV})$$
$$\text{s.t. } D(g(b_1, b_2), g_M - \Delta g(b_1, b_2)) \le \varepsilon,$$
$$\mu_{1m}b_1 + \mu_{2m}b_2 \pm 0,$$

where $\|\cdot\|_{TV}$ denotes the image total-variation (TV), the $l_2$-norm-data-fidelity function is given by:

$$(\overline{g}(b_1,b_2),g_M - \Delta g(b_1,b_2)) = [\|g^{[1]}(b_1,b_2) - g_M^{[1]} + \Delta g^{[1]}(b_1,b_2)\|_2^2 + \|g^{[2]}(b_1,b_2) - g_M^{[2]} + \Delta g^{[2]}(b_1,b_2)\|_2^2]^{1/2},$$

Eq. 68:

Here, $\varepsilon > 0$ is the data constraint parameter. In addition, a non-negativity constraint is imposed on the monochromatic image at energy m. It can be observed that the optimization program in equation 9 is non-convex, because $D(\overline{g}(b_1, b_2), g_M - \Delta g(b_1, b_2))$ is a non-convex function of $(b_1, b_2)$ and thus the data fidelity constraint forms a non-convex set. The non-convexity stems from the non-linear term $\Delta g(b_1, b_2)$, as in its absence the data model becomes linear and so the data fidelity constraint convex.

With regard to the reconstruction methodology, in order to solve the optimization program in equation 68, the steepest descent (SD) procedure is first used to reduce the convex term of the basis-image TV. On the other hand, there is no mathematically exact solver for achieving the global minimum of the NC-data divergence $D(\overline{g}(b_1, b_2), g_M - \Delta g(b_1, b_2))$. Instead, a procedure for lowering the NC-data divergence is considered. It can be observed that, if $\Delta g(b_1, b_2)$ can be estimated, the data divergence becomes convex and can thus be lowered by use of a procedure based upon the projection-onto-convex-sets (POCS). This observation motivates the design of a procedure based upon the POCS updates for potentially lowering the non-convex data divergence as:

$$b_k^{(n+1)} = b_k^{(n)} + \gamma^{(n)}\overline{\mu}_{jk}^{[s]}\frac{g_{Mj}^{[s]} - \Delta g_j^{[s]}(b_1^{(n)}, b_2^{(n)}) - \overline{g}_j^{[s]}(b_1^{(n)}, b_2^{(n)})}{[(\overline{\mu}_{j1}^{[s]})^2 + (\overline{\mu}_{j2}^{[s]})^2]a_j^{[s]}a_j^{[s]T}}a_j^{[s]T}, \text{ and}$$ Eq. 69

$$\Delta g_j^{[s]}(b_1^{(n)}, b_2^{(n)}) = -\ln\sum_m q_{jm}^{[s]}\exp(-a_j^{[s]}(\Delta\mu_{j1m}^{[s]}b_1^{(n)} + \Delta\mu_{j2m}^{[s]}b_2^{(n)})),$$ Eq. 70 where $j \in \{0, 1, \ldots, J^{[s]-1}\}$ for spectrums, the summation over m is from 1 to M, and $a_j^{[s]}$ is the jth row of matrix $\mathcal{A}^{[s]}$.

Unlike the conventional POCS procedure, the update in equation 69 attempts to address the non-convexity of the data divergence by including the estimated NC term $\Delta g_j^{[s]}(b_1^{(n)}, b_2^{(n)})$, and is thus referred to as the NC-POCS procedure. Subsequently, an algorithm may be devised by combining SD and NC-POCS procedures that adaptively lower image TV and data divergence, which may be one example of the ASD-NC-POCS methodology. Parameter $\gamma^{[n]}$ may be identical to that in the conventional ASD-POCS algorithm. Using the reconstructed basis image $b_k^{(n)}$ in equation 61, one can obtain monochromatic image $f_m^{(n)}$ at iteration n.

With regard to necessary convergence conditions, whether or not it can be mathematically shown whether the ASD-NC-POCS algorithm can globally optimally solve the NC program in equation 68, one or more necessary convergence conditions, such as two necessary convergence conditions, can be obtained for the algorithm, with the metrics defined as:

$$\overline{D}(b_1^{(n)}, b_2^{(n)}) = |D(g(b_1^{(n)}, b_2^{(n)}), g_M) - \varepsilon|/\varepsilon$$ Eq. 71

$$\Delta_{TV}(b_1^{(n)}, b_2^{(n)}) = \frac{|(\|b_1^{(n+1)}\|_{TV} + \|b_2^{(n+1)}\|_{TV}) - (\|b_1^{(n)}\|_{TV} + \|b_2^{(n)}\|_{TV})|}{|(\|b_1^{(n+1)}\|_{TV} + \|b_2^{(n+1)}\|_{TV}) + (\|b_1^{(n)}\|_{TV} + \|b_2^{(n)}\|_{TV})|}.$$

The mathematical convergence conditions for the ASD-NC-POCS algorithm can be obtained as:

$$\overline{D}(b_1^{(n)}, b_2^{(n)}) \to 0$$

$$\Delta_{TV}(b_1^{(n)}, b_2^{(n)}) \to 0$$ Eq. 72:

The iteration number $n \to \infty$. Because the mathematical convergence conditions may not be met in practical reconstructions, they are used for devising the practical convergence conditions below:

$$\overline{D}(b_1^{(n)}, b_2^{(n)}) < 10^{-3},$$

$$\Delta^{TV}(b_1^{(n)}, b_2^{(n)}) < 10^{-3}.$$ Eq. 73:

The practical convergence conditions appear to yield reconstructions visually and quantitatively resembling those obtained with tighter convergence conditions.

Thus, in one implementation, fast, low-dose dual-energy scanning configurations are disclosed, enabled by an optimization-based methodology by using real data collected with a clinical diagnostic CT. The scanning configurations considered may readily be realized by use of the standard single-kVp-switch scheme available on existing CT systems without invoking any hardware addition. The configurations may be enabled by use of the ASD-NC-POCS methodology for image reconstruction through numerically solving an NC optimization program. As discussed above, two specific scan configurations (i.e., short+short and half+half) of practical implications, in terms of reduced imaging time and dose, are disclosed for demonstrating the enabling potential of the algorithm. Other scan configurations are contemplated. Monochromatic images may be reconstructed from data collected with the short- and half-scan configurations that may visually and quantitatively resemble those reconstructed from the corresponding full-scan data collected with current dual-energy imaging techniques. In this regard, short- and half-scan configurations (and other scan configurations) may be enabled by the disclosed methodology for achieving dual-energy CT imaging with reduced hardware cost and complexity, imaging dose, and/or time, thus potentially allowing for wide-spread application of dual-energy CT imaging using existing CT scanners.

As discussed above, the performance of the ASD-NC-POCS methodology may depend upon a number of parameters and performance metrics used. For example, the methodology performance may be impacted by the anatomic complexity of the imaged subject, data noise and artifacts, and reconstruction parameters. The metrics considered in the work are visualization and the scatter plots for iodine and calcium differentiation. For demonstration purposes, parameters such as voxel size and data/image dimensions are selected as those in typical clinical applications, whereas constraint parameter E is selected through visual comparison of reconstructions with the corresponding reference images. While the focus is largely on showing the convergent reconstructions for avoiding the need to treat the iteration number as a parameter, other reconstructions are investigated at intermediate iterations (e.g., n=30). One can observe that reconstructions at earlier iterations can visually and quantitatively resemble the convergent reconstructions.

While various scan configurations, including the two methodology-enabled short- and half-scan configurations are disclosed, additional configurations of scanning-time/dose efficiency and low-hardware cost are contemplated, including helical source trajectory and/or off-set detector configurations. Furthermore, the approach and methodology may be extended to CT scanning configurations involving multiple spectra (e.g., greater than 2 spectra), as discussed above.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A multi-spectral tomography imaging system comprising:
   one or more source devices configured to direct beams of radiation in multiple spectra to a region of interest (ROI);
   one or more detectors configured to receive at least a portion of the beams of radiation; and
   a processor in communication with the one or more source devices and the one or more detectors, wherein the processor is configured to:
   cause a first relative movement in at least one of the one or more source devices, the one or more detectors, and the ROI such that a first beam of radiation with a first spectrum is directed to the ROI for less than 360 degrees of movement of the ROI relative to the one or more source devices and the one or more detectors;
   process data detected by the one or more detectors, wherein the data results at least in part from the first beam of radiation with the first spectrum that is directed to the ROI for less than the 360 degrees of movement of the ROI; and
   generate an image of the ROI based on the processed data.

2. The multi-spectral tomography imaging system of claim 1, wherein the beams of radiation in multiple spectra comprise the first beam of radiation at the first spectrum and a second beam of radiation at a second spectrum such that the system performs dual-energy X-ray tomography or dual-energy computed tomography, and wherein the processor is configured to control the one or more source devices such that the one or more source devices direct the first beam of radiation and the second beam of radiation at the ROI each for less than $2\pi$ of the movement of the ROI relative to the one or more source devices and the one or more detectors.

3. The multi-spectral tomography imaging system of claim 1, wherein the one or more source devices comprise a single source device, and wherein the single source device comprises a radiation source and a switch configured to switch a spectrum of radiation output by the radiation source between at least two different spectra, and wherein the processor is configured to control the radiation source and the switch such that the single source device outputs the beams of radiation at each of the at least two different spectra during a respective relative movement of the ROI relative to the single source device and the one or more detectors.

4. The multi-spectral tomography imaging system of claim 3, wherein the respective relative movement of the ROI is 180° or less.

5. The multi-spectral tomography imaging system of claim 1, wherein the one or more source devices comprise a single source device, wherein the single source device comprises a radiation source and a switch configured to switch the radiation source between the first spectrum and a second spectrum, wherein the processor is configured to control the radiation source and the switch so that the single source device outputs radiation in the first spectrum during the first relative movement, and outputs radiation in the second spectrum during a second relative movement of the ROI with respect to the single source device and the one or more detectors, and wherein the first relative movement and the second relative movement are less than 360 degrees.

6. The multi-spectral tomography imaging system of claim 5, wherein the first relative movement is less than 90°, and wherein the second relative movement is less than 180°.

7. The multi-spectral tomography imaging system of claim 5, wherein the processor is configured to control the radiation source and the switch such that the single source device outputs radiation continuously at the first spectrum during the first relative movement of the ROI, and wherein the processor is configured to control the radiation source and the switch such that the single source device outputs radiation continuously at the second spectrum during the second relative movement of the ROI.

8. The multi-spectral tomography imaging system of claim 5, wherein the first relative movement of the ROI with respect to the single source device and the one or more detectors is at a first angle, and wherein the second relative movement of the ROI with respect to the single source device and the one or more detectors is at a second angle, and wherein a sum of the first angle and the second angle is 360 degrees or less.

9. The multi-spectral tomography imaging system of claim 8, wherein the single source device is configured to:
   output at the first spectrum continuously for the first angle; and
   output at the second spectrum discontinuously for the second angle.

10. The multi-spectral tomography imaging system of claim 8, wherein the single source device is configured to output at the first spectrum discontinuously for the first angle and output at the second spectrum discontinuously for the second angle.

11. The multi-spectral tomography imaging system of claim 10, wherein the first angle is a sum of rotation segments of relative movement during which the single source device outputs at the first spectrum.

12. The multi-spectral tomography imaging system of claim 1, wherein the one or more sources comprise a single source device that directs a first beam of radiation through a filter to form a first spectrum and that directs a second beam of radiation that does not go through the filter to form a second spectrum.

13. The multi-spectral tomography imaging system of claim 1, wherein the processor is configured to numerically solve an optimization program to process the data.

* * * * *